(12) United States Patent
Washburn, II et al.

(10) Patent No.: US 10,945,588 B2
(45) Date of Patent: *Mar. 16, 2021

(54) FULLY INTEGRATED, DISPOSABLE TISSUE VISUALIZATION DEVICE

(71) Applicant: Trice Medical, Inc., Malvern, PA (US)

(72) Inventors: Richard H. Washburn, II, Wayne, PA (US); Alfred J. Intintoli, West Chester, PA (US); Andrew C. Davison, Downingtown, PA (US)

(73) Assignee: Trice Medical, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,095

(22) Filed: Sep. 9, 2019

(65) Prior Publication Data
US 2020/0000491 A1 Jan. 2, 2020

Related U.S. Application Data

(63) Continuation of application No. 16/125,549, filed on Sep. 7, 2018, now Pat. No. 10,405,886, which is a
(Continued)

(51) Int. Cl.
*A61B 17/34* (2006.01)
*A61B 1/12* (2006.01)
(Continued)

(52) U.S. Cl.
CPC ...... *A61B 1/00071* (2013.01); *A61B 1/00066* (2013.01); *A61B 1/00096* (2013.01);
(Continued)

(58) Field of Classification Search
CPC ..... A61B 1/313; A61B 1/3132; A61B 1/3135; A61B 1/3137; A61B 1/317;
(Continued)

(56) References Cited

U.S. PATENT DOCUMENTS 3,797,505 A 3/1974 Gilhaus
3,835,842 A 9/1974 Iglesias
(Continued)

FOREIGN PATENT DOCUMENTS

AU 2015204444 1/2018
CN 2557085 Y 6/2003
(Continued)

OTHER PUBLICATIONS

U.S. Appl. No. 15/187,583, filed Jun. 20, 2016, Kienzle et al.
(Continued)

*Primary Examiner* — Ryan N Henderson
(74) *Attorney, Agent, or Firm* — Knobbe, Martens, Olson & Bear, LLP

(57) ABSTRACT

The present invention relates to a fully integrated sterilizable one time use disposable tissue visualization device and methods for using such devices. Preferred embodiments of the invention facilitate the visualization of an internal tissue site while causing a minimum of damage to the surrounding tissue. Further preferred embodiments may allow for the delivery of fluids and other treatment to an internal tissue site.

9 Claims, 32 Drawing Sheets

US 10,945,588 B2

Page 2

Related U.S. Application Data continuation of application No. 15/234,999, filed on Aug. 11, 2016, now abandoned.

(60) Provisional application No. 62/203,898, filed on Aug. 11, 2015.

(51) Int. Cl.

| | | |
|---|---|---|
| *A61B 1/317* | (2006.01) | |
| *A61B 1/05* | (2006.01) | |
| *A61B 1/313* | (2006.01) | |
| *A61B 1/00* | (2006.01) | |
| *A61B 1/015* | (2006.01) | |
| *A61B 1/045* | (2006.01) | |
| *A61B 1/07* | (2006.01) | |
| *A61B 90/30* | (2016.01) | |
| *A61B 90/00* | (2016.01) | |

(52) U.S. Cl.
CPC .......... *A61B 1/00108* (2013.01); *A61B 1/015* (2013.01); *A61B 1/045* (2013.01); *A61B 1/05* (2013.01); *A61B 1/07* (2013.01); *A61B 1/12* (2013.01); *A61B 1/313* (2013.01); *A61B 1/317* (2013.01); *A61B 17/3478* (2013.01); *A61B 1/00103* (2013.01); *A61B 1/00188* (2013.01); *A61B 90/361* (2016.02); *A61B 2090/306* (2016.02); *A61B 2217/007* (2013.01)

(58) Field of Classification Search
CPC ............ A61B 1/00064; A61B 1/00066; A61B 1/00096; A61B 1/00133; A61B 1/00163; A61B 1/00165; A61B 1/00167; A61B 1/0017; A61B 1/00174; A61B 1/00177; A61B 1/00179; A61B 1/00181; A61B 1/00183; A61B 1/002; A61B 1/0058; A61B 1/01; A61B 1/012; A61B 1/015; A61B 1/018; A61B 1/04; A61B 1/042; A61B 1/045; A61B 1/05; A61B 1/051; A61B 1/053; A61B 1/055; A61B 17/34; A61B 2017/34; A61B 1/00071; A61B 17/3478; A61B 17/3474; A61B 90/361; A61B 2090/306

See application file for complete search history.

(56) References Cited

U.S. PATENT DOCUMENTS

| | | |
|---|---|---|
| 3,871,358 A | 3/1975 | Fukuda et al. |
| 4,069,823 A | 1/1978 | Isakov et al. |
| 4,254,762 A | 3/1981 | Yoon |
| 4,519,391 A | 5/1985 | Murakoshi |
| 4,624,243 A | 11/1986 | Lowery et al. |
| 4,646,738 A | 3/1987 | Trott |
| 4,651,201 A | 3/1987 | Schoolman |
| 4,678,459 A | 7/1987 | Onik et al. |
| 4,697,210 A | 9/1987 | Toyota et al. |
| 4,700,702 A | 10/1987 | Nilsson |
| 4,750,902 A | 6/1988 | Wuchinich et al. |
| 4,845,555 A | 7/1989 | Yabe et al. |
| 4,919,112 A | 4/1990 | Siegmund |
| 5,088,676 A | 2/1992 | Orchard et al. |
| 5,131,382 A | 7/1992 | Meyer |
| 5,170,775 A | 12/1992 | Tagami |
| 5,178,130 A | 1/1993 | Kaiya |
| 5,188,093 A | 2/1993 | Lafferty et al. |
| 5,190,028 A | 3/1993 | Lafferty et al. |
| 5,195,541 A | 3/1993 | Obenchain |
| 5,228,430 A | 7/1993 | Sakamoto |
| 5,242,441 A | 9/1993 | Avitall |
| 5,244,459 A | 9/1993 | Hill |
| 5,269,785 A | 12/1993 | Bonutti |
| 5,291,010 A | 3/1994 | Tsuji |
| 5,312,407 A | 5/1994 | Carter |
| 5,313,962 A | 5/1994 | Obenchain |
| 5,318,589 A | 6/1994 | Lichtman |
| 5,373,312 A | 6/1994 | Bala |
| 5,334,183 A | 8/1994 | Wuchinich |
| 5,351,678 A | 10/1994 | Clayton et al. |
| 5,354,302 A | 10/1994 | Ko |
| 5,365,267 A | 11/1994 | Edwards |
| 5,368,015 A | 11/1994 | Wilk |
| 5,369,525 A | 11/1994 | Bala et al. |
| 5,373,317 A | 12/1994 | Salavi et al. |
| 5,373,392 A | 12/1994 | Bala |
| 5,383,888 A | 1/1995 | Zvenyatsky et al. |
| 5,395,312 A | 3/1995 | Desai |
| 5,395,313 A | 3/1995 | Naves et al. |
| 5,398,685 A | 3/1995 | Wilk et al. |
| 5,403,276 A | 4/1995 | Schechter et al. |
| 5,403,342 A | 4/1995 | Tovey et al. |
| 5,406,940 A | 4/1995 | Melzer et al. |
| 5,417,203 A | 5/1995 | Tovey et al. |
| 5,423,312 A | 6/1995 | Siegmund et al. |
| 5,425,355 A | 6/1995 | Kulick |
| 5,476,473 A | 12/1995 | Heckele |
| 5,478,328 A | 12/1995 | Silverman et al. |
| 5,484,433 A | 1/1996 | Taylor et al. |
| 5,494,483 A | 2/1996 | Adair |
| 5,500,012 A | 3/1996 | Brucker et al. |
| 5,512,036 A | 4/1996 | Tamburrino et al. |
| 5,518,502 A | 5/1996 | Kaplan et al. |
| 5,547,455 A | 8/1996 | McKenna et al. |
| 5,569,158 A | 10/1996 | Suzuki et al. |
| 5,577,992 A | 11/1996 | Chiba et al. |
| 5,582,575 A | 12/1996 | Heckele et al. |
| 5,591,192 A | 1/1997 | Privitera et al. |
| 5,601,525 A | 2/1997 | Okada |
| 5,621,830 A | 4/1997 | Paul et al. |
| 5,630,784 A | 5/1997 | Siegmund et al. |
| 5,630,837 A | 5/1997 | Crowley |
| 5,643,294 A | 7/1997 | Tovey et al. |
| 5,647,840 A | 7/1997 | D'Amelio et al. |
| 5,674,191 A | 10/1997 | Edwards et al. |
| 5,695,513 A | 12/1997 | Johnson et al. |
| 5,704,534 A | 1/1998 | Huitema et al. |
| 5,707,382 A | 1/1998 | Sierocuk et al. |
| 5,766,194 A | 1/1998 | Smith |
| 5,713,505 A | 2/1998 | Huitema |
| 5,722,403 A | 3/1998 | McGee et al. |
| 5,735,792 A | 4/1998 | Vanden Hoeck et al. |
| 5,757,458 A | 5/1998 | Miller et al. |
| 5,766,199 A | 6/1998 | Heisler et al. |
| 5,766,200 A | 6/1998 | Mazurek et al. |
| 5,785,647 A | 7/1998 | Tompkins et al. |
| 5,788,636 A | 8/1998 | Curley |
| 5,807,240 A | 9/1998 | Muller et al. |
| 5,818,527 A | 10/1998 | Yamaguchi et al. |
| 5,836,943 A | 11/1998 | Miller, III |
| 5,857,961 A | 1/1999 | Vanden Hoeck et al. |
| 5,864,359 A | 1/1999 | Kazakevich |
| 5,868,664 A | 2/1999 | Speier et al. |
| 5,873,814 A | 2/1999 | Adair |
| 5,873,816 A | 2/1999 | Ishii |
| 5,873,817 A | 2/1999 | Adair |
| 5,879,285 A | 3/1999 | Ishii |
| 5,888,193 A | 3/1999 | Breidental et al. |
| 5,902,272 A | 5/1999 | Eggers et al. |
| 5,916,146 A | 6/1999 | Allotta et al. |
| 5,928,137 A | 7/1999 | Crawford |
| 5,929,901 A | 7/1999 | Adair et al. |
| 5,941,817 A | 8/1999 | Crawford |
| 5,976,075 A | 11/1999 | Beane et al. |
| 5,976,076 A | 11/1999 | Kolff et al. |
| 5,976,077 A | 11/1999 | Wittens et al. |
| 5,986,693 A | 11/1999 | Adair et al. |
| 6,001,084 A | 12/1999 | Riek et al. |
| 6,007,554 A | 12/1999 | Van Ess |
| 6,043,839 A | 3/2000 | Adair et al. |
| 6,045,549 A | 4/2000 | Smethers et al. |
| 6,068,603 A | 5/2000 | Suzuki |

(56) References Cited

U.S. PATENT DOCUMENTS

| | | |
|---|---|---|
| 6,080,101 A | 6/2000 | Tatsuno et al. |
| 6,086,528 A | 7/2000 | Adair |
| 6,053,923 A | 8/2000 | Veca et al. |
| 6,099,465 A | 8/2000 | Inoue |
| 6,112,123 A | 8/2000 | Kelleher et al. |
| 6,110,127 A | 9/2000 | Suzuki |
| 6,113,614 A | 9/2000 | Mears |
| 6,126,592 A | 10/2000 | Proch et al. |
| 6,129,662 A | 10/2000 | Li et al. |
| 6,142,957 A | 11/2000 | Diamond et al. |
| 6,149,646 A | 11/2000 | West, Jr. et al. |
| 6,156,033 A | 12/2000 | Tu et al. |
| 6,193,692 B1 | 2/2001 | Harris et al. |
| 6,211,904 B1 | 4/2001 | Adair et al. |
| 6,234,955 B1 | 5/2001 | Silverman et al. |
| 6,241,727 B1 | 6/2001 | Tu et al. |
| 6,251,120 B1 | 6/2001 | Dorn |
| 6,261,226 B1 | 7/2001 | McKenna et al. |
| 6,264,670 B1 | 7/2001 | Chin |
| 6,275,255 B1 | 8/2001 | Adair et al. |
| 6,277,137 B1 | 8/2001 | Chin |
| 6,310,642 B1 | 10/2001 | Adair et al. |
| 6,315,712 B1 | 11/2001 | Rovegno |
| 6,316,215 B1 | 11/2001 | Adair et al. |
| 6,322,494 B1 | 11/2001 | Bullicant et al. |
| 6,331,165 B1 | 12/2001 | Turturro et al. |
| 6,332,881 B1 | 12/2001 | Carner et al. |
| 6,371,909 B1 | 4/2002 | Hoeg et al. |
| 6,387,043 B1 | 5/2002 | Yoon |
| 6,390,972 B1 | 5/2002 | Speier et al. |
| 6,419,626 B1 | 7/2002 | Yoon |
| 6,419,627 B1 | 7/2002 | Ben Nun |
| 6,419,654 B1 | 7/2002 | Kadan |
| 6,424,369 B1 | 7/2002 | Adair et al. |
| 6,447,445 B1 | 9/2002 | Hirano |
| 6,452,626 B1 | 9/2002 | Adair et al. |
| 6,458,140 B2 | 10/2002 | Akin et al. |
| 6,459,481 B1 | 10/2002 | Schaack |
| 6,464,633 B1 | 10/2002 | Hosoda et al. |
| 6,464,711 B1 | 10/2002 | Emans et al. |
| 6,468,274 B1 | 10/2002 | Alleynne et al. |
| 6,478,730 B1 | 11/2002 | Bala et al. |
| 6,491,690 B1 | 12/2002 | Goble et al. |
| 6,572,578 B1 | 2/2003 | Blanchard |
| 6,527,753 B2 | 3/2003 | Sekine et al. |
| 6,533,749 B1 | 3/2003 | Mitusina et al. |
| 6,544,194 B1 | 4/2003 | Kortenbach et al. |
| 6,561,973 B1 | 5/2003 | Bala |
| 6,569,085 B2 | 5/2003 | Kortenbach et al. |
| 6,583,240 B2 | 6/2003 | Wang et al. |
| 6,585,734 B2 | 7/2003 | Levinson |
| 6,602,247 B2 | 8/2003 | Lalonde |
| 6,602,248 B1 | 8/2003 | Sharps et al. |
| 6,605,087 B2 | 8/2003 | Swartz et al. |
| 6,607,529 B1 | 8/2003 | Jones et al. |
| 6,623,437 B2 | 9/2003 | Hinchliffe et al. |
| 6,632,227 B2 | 10/2003 | Adams |
| 6,652,522 B2 | 11/2003 | Cucin |
| 6,656,132 B1 | 12/2003 | Ouchi |
| 6,656,195 B2 | 12/2003 | Peters et al. |
| 6,660,011 B2 | 12/2003 | Levinson |
| 6,675,033 B1 | 1/2004 | Lardo et al. |
| 6,679,838 B2 | 1/2004 | Bala |
| 6,682,535 B2 | 1/2004 | Hoogland |
| 6,689,130 B2 | 2/2004 | Arai et al. |
| 6,692,432 B1 | 2/2004 | Yarush et al. |
| 6,695,772 B1 | 2/2004 | Bon et al. |
| 6,726,684 B1 | 4/2004 | Woloszko et al. |
| 6,750,037 B2 | 6/2004 | Adair et al. |
| 6,764,439 B2 | 7/2004 | Schaaf et al. |
| 6,805,715 B2 | 10/2004 | Reuter et al. |
| 6,820,791 B2 | 11/2004 | Adams |
| 6,832,984 B2 | 12/2004 | Stelzer et al. |
| 6,833,000 B2 | 12/2004 | Levinson |
| 6,835,198 B2 | 12/2004 | Bonutti |
| 6,837,887 B2 | 1/2005 | Woloszko et al. |
| 6,862,036 B2 | 3/2005 | Adair et al. |
| 6,863,651 B2 | 3/2005 | Remijan et al. |
| 6,885,801 B1 | 3/2005 | Shankar et al. |
| 6,893,436 B2 | 5/2005 | Woodard et al. |
| 6,899,672 B2 | 5/2005 | Chin et al. |
| 6,902,526 B2 | 6/2005 | Katzman |
| 6,982,740 B2 | 1/2006 | Adair et al. |
| 6,982,742 B2 | 1/2006 | Adair et al. |
| 6,997,941 B2 | 2/2006 | Sharkey et al. |
| 7,002,621 B2 | 2/2006 | Adair et al. |
| 7,004,938 B2 | 2/2006 | Ormsby et al. |
| 7,030,904 B2 | 4/2006 | Adair et al. |
| 7,060,028 B2 | 6/2006 | Luloh et al. |
| 7,094,200 B2 | 8/2006 | Katzman |
| 7,108,657 B2 | 9/2006 | Irion et al. |
| 7,137,981 B2 | 11/2006 | Long |
| 7,156,559 B2 | 1/2007 | Gauthier, Jr. et al. |
| 7,160,247 B2 | 1/2007 | Deppmeier et al. |
| 7,160,295 B1 | 1/2007 | Garito et al. |
| 7,169,147 B2 | 1/2007 | Nosel |
| 7,179,255 B2 | 2/2007 | Lettice et al. |
| 7,198,635 B2 | 4/2007 | Danek et al. |
| 7,214,183 B2 | 5/2007 | Miyake |
| 7,258,663 B2 | 8/2007 | Doguchi et al. |
| 7,269,344 B2 | 9/2007 | Nishioka et al. |
| 7,270,658 B2 | 9/2007 | Woloszko et al. |
| 7,318,823 B2 | 1/2008 | Sharps et al. |
| 7,320,688 B2 | 1/2008 | Foley et al. |
| RE40,156 E | 3/2008 | Sharps et al. |
| 7,435,010 B2 | 10/2008 | Gauthier, Jr. et al. |
| 7,453,984 B2 | 11/2008 | Chen et al. |
| 7,491,168 B2 | 2/2009 | Raymond et al. |
| 7,572,578 B2 | 2/2009 | Blanchard |
| 7,689,268 B2 | 3/2010 | Marshik-Geurts et al. |
| 7,699,773 B2 | 4/2010 | Forkey et al. |
| 7,708,689 B2 | 5/2010 | Deppmeier et al. |
| 7,857,755 B2 | 12/2010 | Kupferschmid et al. |
| 7,918,787 B2 | 4/2011 | Saadat |
| 7,942,814 B2 | 5/2011 | Remijan et al. |
| 8,016,839 B2 | 9/2011 | Wilk |
| 8,038,602 B2 | 10/2011 | Gill et al. |
| 8,046,057 B2 | 10/2011 | Clarke |
| 8,052,609 B2 | 11/2011 | Harhen |
| 8,142,346 B2 | 3/2012 | Shoroji et al. |
| 8,170,319 B2 | 5/2012 | Shukla |
| 8,277,411 B2 | 10/2012 | Gellman |
| 8,317,689 B1 | 11/2012 | Remijan et al. |
| 8,475,361 B2 | 7/2013 | Barlow et al. |
| 8,885,034 B2 | 11/2014 | Adair et al. |
| 8,951,274 B2 | 2/2015 | Adams et al. |
| 10,045,686 B2 | 8/2018 | OuYang et al. |
| 2001/0036015 A1 | 11/2001 | Eguchi |
| 2001/0053873 A1 | 12/2001 | Schaaf et al. |
| 2002/0007110 A1 | 1/2002 | Irion |
| 2002/0080248 A1 | 6/2002 | Adair et al. |
| 2002/0087047 A1 | 7/2002 | Remijan et al. |
| 2002/0177847 A1 | 11/2002 | Long |
| 2003/0040668 A1 | 2/2003 | Kaneko et al. |
| 2003/0120156 A1 | 6/2003 | Forrester et al. |
| 2003/0144594 A1 | 7/2003 | Gellman |
| 2003/0181905 A1 | 9/2003 | Long |
| 2003/0220574 A1 | 11/2003 | Markus et al. |
| 2003/0233024 A1 | 12/2003 | Ando |
| 2004/0102772 A1 | 5/2004 | Baxter et al. |
| 2004/0162554 A1 | 8/2004 | Lee et al. |
| 2004/0162572 A1 | 8/2004 | Sauer |
| 2004/0215061 A1 | 10/2004 | Kimmel et al. |
| 2005/0038317 A1 | 2/2005 | Ratnakar |
| 2005/0090762 A1 | 4/2005 | Burbank et al. |
| 2005/0096504 A1 | 5/2005 | Akiba |
| 2005/0113641 A1 | 5/2005 | Bala |
| 2005/0154262 A1 | 7/2005 | Banik et al. |
| 2005/0192532 A1 | 9/2005 | Kucklick et al. |
| 2005/0197536 A1 | 9/2005 | Banik et al. |
| 2005/0197658 A1 | 9/2005 | Platt |
| 2005/0213267 A1 | 9/2005 | Azrai et al. |
| 2005/0228228 A1 | 10/2005 | Boulais |
| 2005/0234296 A1 | 10/2005 | Saadat et al. |

(56) References Cited

U.S. PATENT DOCUMENTS

| | | |
|---|---|---|
| 2005/0277808 A1 | 12/2005 | Sonnenschein et al. |
| 2006/0004258 A1 | 1/2006 | Sun et al. |
| 2006/0004354 A1 | 1/2006 | Suslov |
| 2006/0030861 A1 | 2/2006 | Simonson et al. |
| 2006/0063973 A1 | 3/2006 | Makower et al. |
| 2006/0069303 A1 | 3/2006 | Couvillon, Jr. |
| 2006/0069313 A1 | 3/2006 | Couvillon, Jr. |
| 2006/0084839 A1 | 4/2006 | Mourlas et al. |
| 2006/0089633 A1 | 4/2006 | Bleich et al. |
| 2006/0106282 A1 | 5/2006 | Bala |
| 2006/0111613 A1 | 5/2006 | Boutillette et al. |
| 2006/0149129 A1 | 7/2006 | Watts et al. |
| 2006/0167340 A1 | 7/2006 | Pease et al. |
| 2006/0173244 A1 | 8/2006 | Boulas et al. |
| 2006/0178560 A1 | 8/2006 | Saadat et al. |
| 2006/0183975 A1 | 8/2006 | Saadat et al. |
| 2006/0190063 A1 | 8/2006 | Kanzius |
| 2006/0206007 A1 | 9/2006 | Bala |
| 2006/0206118 A1 | 9/2006 | Kim et al. |
| 2006/0241648 A1 | 10/2006 | Bleich et al. |
| 2006/0241665 A1 | 10/2006 | Bosley et al. |
| 2006/0258951 A1 | 11/2006 | Bleich et al. |
| 2006/0270904 A1 | 11/2006 | Kepferschmid et al. |
| 2006/0276690 A1 | 12/2006 | Farris, III et al. |
| 2006/0281972 A1 | 12/2006 | Pease et al. |
| 2006/0287576 A1 | 12/2006 | Tsuji et al. |
| 2006/0293562 A1 | 12/2006 | Uchimura et al. |
| 2007/0038117 A1 | 2/2007 | Bala |
| 2007/0049794 A1 | 3/2007 | Glassenberg et al. |
| 2007/0060798 A1 | 3/2007 | Krupnik et al. |
| 2007/0071311 A1 | 3/2007 | Rovira-Mas et al. |
| 2007/0073109 A1 | 3/2007 | Irion |
| 2007/0075654 A1 | 4/2007 | Kishinevsky |
| 2007/0093689 A1 | 4/2007 | Steinberg |
| 2007/0115376 A1 | 5/2007 | Igarashi |
| 2007/0123888 A1 | 5/2007 | Bleich et al. |
| 2007/0129604 A1 | 6/2007 | Hatcher et al. |
| 2007/0129719 A1 | 6/2007 | Kendale et al. |
| 2007/0135874 A1 | 6/2007 | Bala |
| 2007/0161855 A1 | 7/2007 | Mikkaichi et al. |
| 2007/0167678 A1 | 7/2007 | Moskowitz et al. |
| 2007/0167681 A1 | 7/2007 | Gill et al. |
| 2007/0179340 A1 | 8/2007 | Jorgensen |
| 2007/0213733 A1 | 9/2007 | Bleich et al. |
| 2007/0213734 A1 | 9/2007 | Bleich et al. |
| 2007/0213735 A1 | 9/2007 | Bleich et al. |
| 2007/0219412 A1 | 9/2007 | DiGiovanni et al. |
| 2007/0225556 A1 | 9/2007 | Oritz et al. |
| 2007/0232850 A1 | 10/2007 | Stokes et al. |
| 2007/0249904 A1 | 10/2007 | Amano et al. |
| 2007/0276183 A1 | 11/2007 | Melder |
| 2007/0287886 A1 | 12/2007 | Saadat |
| 2007/0293853 A1 | 12/2007 | Truckai et al. |
| 2008/0009747 A1 | 1/2008 | Saadat et al. |
| 2008/0033465 A1 | 2/2008 | Schmitz et al. |
| 2008/0045924 A1 | 2/2008 | Cox et al. |
| 2008/0051629 A1 | 2/2008 | Sugiyama et al. |
| 2008/0062429 A1 | 3/2008 | Liang et al. |
| 2008/0064925 A1 | 3/2008 | Gill et al. |
| 2008/0091064 A1 | 4/2008 | Laser |
| 2008/0103504 A1 | 5/2008 | Schmitz et al. |
| 2008/0108869 A1 | 5/2008 | Sanders et al. |
| 2008/0147018 A1 | 6/2008 | Squilla et al. |
| 2008/0161809 A1 | 7/2008 | Schmitz et al. |
| 2008/0051812 A1 | 8/2008 | Schmitz et al. |
| 2008/0200758 A1 | 8/2008 | Orbay et al. |
| 2008/0207992 A1 | 8/2008 | Scheller et al. |
| 2008/0207996 A1 | 8/2008 | Tsai |
| 2008/0214896 A1 | 9/2008 | Krupa et al. |
| 2008/0262302 A1 | 10/2008 | Azarbarzin et al. |
| 2008/0287961 A1 | 11/2008 | Miyamoto et al. |
| 2008/0300456 A1 | 12/2008 | Irion et al. |
| 2008/0300462 A1 | 12/2008 | Intoccia et al. |
| 2009/0043165 A1 | 2/2009 | Kucklick et al. |
| 2009/0043167 A1 | 2/2009 | Leiner |
| 2009/0076329 A1 | 3/2009 | Su et al. |
| 2009/0225159 A1 | 9/2009 | Schneider |
| 2009/0253967 A1 | 10/2009 | Gill et al. |
| 2009/0264706 A1 | 10/2009 | Bala |
| 2010/0016855 A1 | 1/2010 | Ramstein et al. |
| 2010/0022824 A1 | 1/2010 | Cybulski et al. |
| 2010/0056862 A1 | 3/2010 | Bakos |
| 2010/0063352 A1 | 3/2010 | Matsuura |
| 2010/0063356 A1 | 3/2010 | Smith |
| 2010/0087798 A1 | 4/2010 | Adams et al. |
| 2010/0094231 A1 | 4/2010 | Bleich et al. |
| 2010/0121139 A1 | 5/2010 | OuYang et al. |
| 2010/0121155 A1 | 5/2010 | OuYang et al. |
| 2010/0165335 A1 | 7/2010 | Tearney |
| 2010/0165336 A1 | 7/2010 | Terney |
| 2010/0217080 A1 | 8/2010 | Cheung et al. |
| 2010/0256446 A1 | 10/2010 | Raju |
| 2010/0274081 A1 | 10/2010 | Okoniewski |
| 2010/0284580 A1 | 11/2010 | OuYang et al. |
| 2010/0286477 A1 | 11/2010 | OuYang et al. |
| 2011/0009694 A1 | 1/2011 | Schultz et al. |
| 2011/0034769 A1 | 2/2011 | Adair et al. |
| 2011/0046652 A1 | 2/2011 | Rehnke et al. |
| 2011/0227509 A1 | 9/2011 | Saleh |
| 2011/0263933 A1 | 10/2011 | Schaaf |
| 2011/0263983 A1 | 10/2011 | Peszynski |
| 2011/0276113 A1 | 11/2011 | Cybulski |
| 2012/0016397 A1 | 1/2012 | Briganti et al. |
| 2012/0071721 A1 | 3/2012 | Remijan et al. |
| 2012/0088968 A1 | 4/2012 | Gambhir et al. |
| 2012/0095458 A1 | 4/2012 | Cybulski et al. |
| 2012/0206591 A1 | 8/2012 | Selby et al. |
| 2012/0220827 A1 | 8/2012 | Sargeant |
| 2012/0241188 A1 | 9/2012 | Power et al. |
| 2012/0265009 A1 | 10/2012 | OuYang et al. |
| 2013/0046142 A1 | 2/2013 | Remijan et al. |
| 2013/0144122 A1 | 6/2013 | Adair et al. |
| 2013/0296648 A1 | 11/2013 | OuYang et al. |
| 2013/0303846 A1 | 11/2013 | Cybulski et al. |
| 2014/0276472 A1 | 9/2014 | VanderStek et al. |
| 2015/0112324 A1 | 4/2015 | Cybulski |
| 2015/0157387 A1 | 6/2015 | OuYang et al. |
| 2015/0196193 A1 | 7/2015 | Kienzle et al. |
| 2015/0196197 A1 | 7/2015 | Kienzle et al. |
| 2015/0313634 A1 | 11/2015 | Gross et al. |
| 2016/0045224 A1 | 2/2016 | Hendershot, III |
| 2016/0296108 A1 | 10/2016 | Kienzle et al. |
| 2017/0042573 A1 | 2/2017 | Savvouras et al. |
| 2017/0086666 A1 | 3/2017 | Kienzle et al. |
| 2017/0265879 A1 | 9/2017 | Washburn, II et al. |
| 2018/0271581 A1 | 9/2018 | OuYang et al. |
| 2019/0321077 A1 | 10/2019 | Kienzle et al. |

FOREIGN PATENT DOCUMENTS

| | | |
|---|---|---|
| CN | 1612708 A | 5/2005 |
| CN | 1779836 A | 5/2006 |
| CN | 101040775 A | 9/2007 |
| CN | 13961177 A | 8/2014 |
| CN | 104367296 A | 2/2015 |
| CN | 106455907 | 2/2017 |
| EP | 1252859 A2 | 10/2002 |
| EP | 2317931 A2 | 5/2011 |
| EP | 2335550 | 6/2011 |
| EP | 2451338 A2 | 5/2012 |
| EP | 3094231 | 11/2016 |
| GB | 2431539 A | 4/2007 |
| JP | S63281620 | 11/1988 |
| JP | H10 33462 A | 2/1998 |
| JP | 2001-161630 | 6/2001 |
| WO | WO 00/09001 | 2/2000 |
| WO | WO 2006/107877 | 10/2006 |
| WO | WO 2007/106740 | 9/2007 |
| WO | WO 2008/016927 | 2/2008 |
| WO | WO 2008/094436 | 8/2008 |
| WO | WO 2008/094439 | 8/2008 |
| WO | WO 2008/094444 | 8/2008 |
| WO | WO 2008/098251 | 8/2008 |
| WO | WO 2009/062179 | 5/2009 |

(56) References Cited

FOREIGN PATENT DOCUMENTS

| WO | WO 2010/011781 | 1/2010 |
| WO | WO 2011/006052 | 1/2011 |
| WO | WO 2014/137530 | 9/2014 |
| WO | WO 2015/106288 | 7/2015 |
| WO | WO 2016/130844 | 8/2016 |
| WO | WO 2017/027749 | 2/2017 |
| WO | WO 2017/161177 | 9/2017 |
| WO | WO 2019/191705 | 10/2019 |

OTHER PUBLICATIONS

U.S. Appl. No. 15/234,999, filed Aug. 11, 2016, Washburn et al.
International Search Report and Written Opinion of International Application No. PCT/US2016/046630 dated Nov. 15, 2016 in 16 pages.
Keller C.A., Hinerman, R., Singh, A., Alvarez, F., "The Use of Endoscopic Argon Plasma Coagulation in Airway Complications After Solid Organ Transplantation," Chest, 2001, vol. 119, No. 6, pp. 1968-1975.
Communication Pursuant to Article 94(3) EPC, Application No. 16 757 416.9-1008, dated Jun. 17, 2019, 3 pages.
European Extended Search Report, Application No. 19171390.8-1008, dated Sep. 24, 2019, 6 pages.

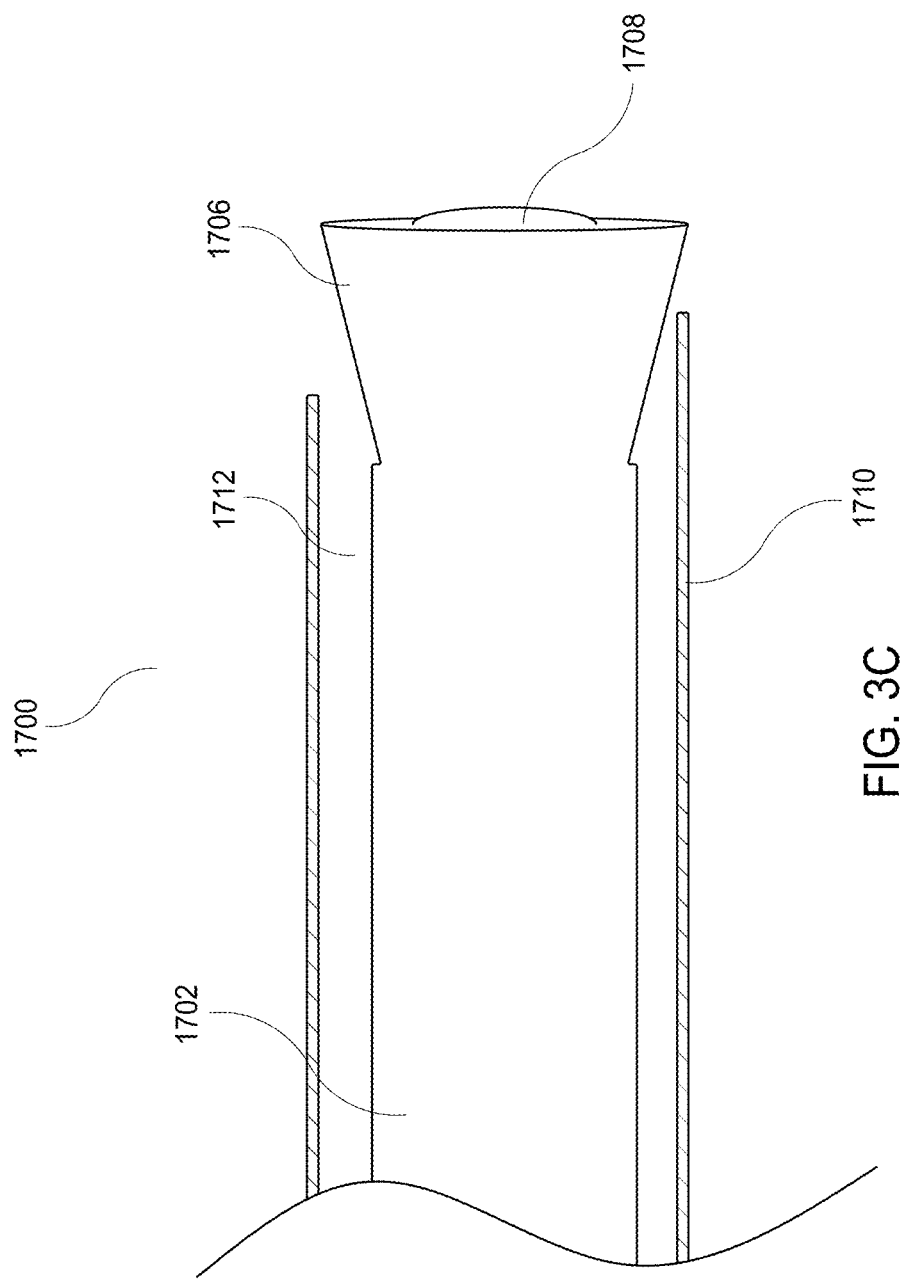

Without Anti-rotation view

User rotates portion of scope where camera is housed

↓

Rotating camera causes image on monitor to rotate

↓

User can lose rotational orientation

Camera orientation          Display orientation

With Anti-rotation view

User rotates portion of scope where camera sensor is housed

↓

Sensor determines angular rotation of camera

↓

Sensor/software maintains image on screen relative to patient orientation

↓

User maintains rotational orientation

Camera orientation      Display orientation

- 3 or 4 buttons around circumference of handle spaced 90° apart
- located at top, left, right (and bottom)
- would also have LED to denote the active button and "up" orientation reference

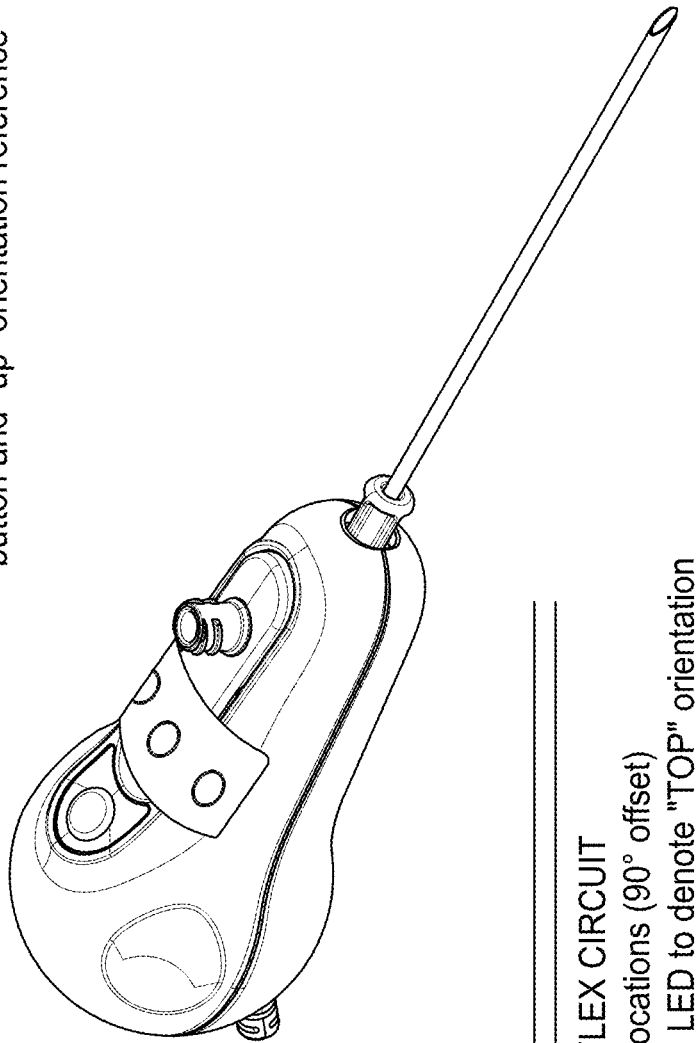

3402

WHEN USER ROTATES HANDLE, THEY CAN RE-ORIENT THE IMAGE ON SCREEN VIA BUTTON AROUND THE CIRCUMFERENCE OF THE HANDLE

MEMBRANE/FLEX CIRCUIT
- 3 button locations (90° offset)
- each with LED to denote "TOP" orientation → SOFTWARE: built-in function for 90° rotation if 45° then more buttons!

FIG. 17

FULLY INTEGRATED, DISPOSABLE TISSUE VISUALIZATION DEVICE

CROSS-REFERENCE TO RELATED APPLICATIONS

This application is a continuation of U.S. application Ser. No. 16/125,549, filed Sep. 7, 2018, entitled FULLY INTEGRATED, DISPOSABLE TISSUE VISUALIZATION DEVICE and is a continuation of U.S. application Ser. No. 15/234,999, filed Aug. 11, 2016, entitled FULLY INTEGRATED, DISPOSABLE TISSUE VISUALIZATION which claims the benefit of U.S. Provisional Application No. 62/203,898, filed Aug. 11, 2015, entitled FULLY INTEGRATED, DISPOSABLE TISSUE VISUALIZATION DEVICE. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

BACKGROUND OF THE INVENTION

Field of the Invention

This application describes embodiments of apparatuses, methods, and systems for the visualization of tissues.

Description of the Related Art

Traditional surgical procedures, both therapeutic and diagnostic, for pathologies located within the body can cause significant trauma to the intervening tissues. These procedures often require a long incision, extensive muscle stripping, prolonged retraction of tissues, denervation and devascularization of tissue. Such procedures can require operating room time of several hours followed by several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

Treatment of internal tissue sites, such as the treatment of an orthopedic joint, often requires visualization of the target internal tissues. However, proper visualization of an internal tissue site can be expensive and time-consuming to schedule, such as when magnetic resonance imaging (MRI) is required. Further, other modes of imaging can potentially damage the tissue site, leading to poor diagnosis and extended recovery time. Consequently, there is need for improved devices and methods for visualization of an internal tissue site.

SUMMARY OF THE INVENTION

Embodiments of the present invention relate to tissue visualization devices, methods, and systems. In some embodiments, tissue visualization devices comprise a visualization sensor and an elongated body having a proximal end and a distal end. The distal end of the elongated body may be dimensioned to pass through a minimally invasive body opening. In certain embodiments, the devices further comprise an integrated articulation mechanism that imparts steerability to at least one of the visualization sensor and the distal end of the elongated body. Further embodiments provide for methods of modifying the internal target tissues of a subject using tissue modification devices.

One preferred implementation of the invention is a fully integrated sterilizable disposable tissue visualization device. The device comprises a handle, and an rigid elongated body extending along a longitudinal axis between a proximal end affixed to the handle and a distal end having a sharpened tip. An image sensor is provided in the handle, and an elongate optical element extends through the probe, the optical element having a proximal end in optical communication with the sensor, and having a distal end.

A control is provided on the handle, for axially moving the elongated body between a proximal position in which the sharpened tip is proximal to the distal end of the optical element, and a distal position in which the sharpened tip is distal to the distal end of the optical element.

An electrical cord may be integrally connected to the handle, having a free end with a connector for releasable electrical connection to an external viewing device.

The integral assembly of the handle, probe and cord may be sterilized and packaged in a single sterile container. This enables opening of the sterile container within a sterile field in a clinical environment, plugging the cord into a compatible external viewing device, and commencing a procedure on a patient without any additional assembly steps.

The distal end of the elongated body may be provided with a lateral deflection. The deflection may be in a first direction relative to the longitudinal axis, and the cord is attached to the handle at a second direction relative to the longitudinal axis, and approximately 180° offset from the first direction. This provides visual and/or tactile feedback of the direction of the distal lateral deflection. Proximal retraction of the elongated body deflects the distal end of the optical element laterally by at least about 1°, in some embodiments at least about 2 or 3 or 5° or more to enhance the field of view. In certain embodiments, rather than a lateral deflection at the distal end of the elongated body, the entire elongated body may be physically bent, providing a curve in the elongated body. Such a curve may have a degree of curvature of approximately at least 0-5°, 5-10°, 10-20°, 20-40°, 40-60°, 60-90°, or greater than 90°.

The optical element may comprise at least 1 and typically a plurality of optical visualization fibers and a distal lens. The optical element may additionally comprise at least one and typically a plurality of illumination optical fibers. The optical visualization fibers, optical illumination fibers and lens may be contained within a tubular body such as a hypotube.

The optical element may have an outside diameter that is spaced radially inwardly from an inside surface of the elongated body to define an annular lumen extending the length of the elongated body. The lumen may be in communication with an injection or an aspiration port on the handle such as for infusion of a media such as an irrigant or active agent, or for aspiration.

In one implementation of the invention, the device comprises an elongated body comprising a 14 gauge needle (2.1 mm Outer Diameter) or outer tubular body having a sharpened distal tip. An optical hypotube is axially moveably positioned within the outer tubular body, such that it may be moved from a distal position in which it extends beyond the sharpened tip and a proximal position in which the sharpened tip is distally exposed. In certain embodiments, the optical hypotube may comprise a distal lens, image guide comprising a multi-element fiber, and additional illumination fibers all contained within a hypotube. The image guide may contain any number of suitable elements, such as 10,000 elements (e.g. fibers), while the hypotube may be of any suitable gauge, such as an 18 gauge hypotube. In some embodiments, the image guide may contain about at least 1,000 elements, at least 3,000 elements, at least 8,000 elements, at least 10,000 elements, at least 12,000 elements, at least 15,000 elements, at least 20,000 elements, at least 30,000 elements, or more than 30,000 elements. The elongated body may comprise an infusion lumen, such as an annular space between the optical hypotube and the inside diameter of the outer tubular body. The lumen may be utilized for infusion of a therapeutic medium such as saline, liquid containing biological components such as stem cells, synthetic lubricant or other flowable media. In some embodiments, the lumen may be used to deliver saline to a tissue site or other therapeutic agents, such as growth factors, anti-bacterial molecules, or anti-inflammatory molecules. In certain embodiments, and as described elsewhere in the specification, the optical hypotube may be located non-concentrically within the elongated body. For example, the central axis of the optical hypotube may be biased towards one side or another of the elongated body. The optical hypotube may be aligned along the bottom of the elongated body to aid in blunting of the sharpened distal tip of the elongated body. Further, in certain embodiments and as described elsewhere in the specification, the distal end of the optical hypotube may be bent to provide an enhanced field of view. A difference in axes between the optical hypotube and the elongated body would also advantageously allow for more vertical clearance of the optical hypotube when the optical hypotube comprises a bent/deflected distal tip.

In some embodiments, the visualization devices described herein this section or elsewhere in the specification may be used for various image guided injections beyond joint injections. For example, drugs sometimes need to be injected into the pericardium around the heart. Currently, such injections are completed blindly or with expensive visualization. As an alternative application, the visualization devices can be used when pericardial effusion occurs, a condition that occurs when too much fluid builds up around the heart. The physician can use a needle to enter the pericardial space and then drain fluid from the pericardium via a procedure known as pericardiocentesis. However, such a task could also be completed using certain embodiments of the tissue visualization devices, via penetration of the pericardium with the elongated body, followed by fluid drainage. Currently, physicians use imaging devices such as echocardiography or fluoroscopy (X ray) to guide this type of work.

The elongated body is carried by a proximal hand piece, which may be connected via cable or wireless connection to a monitor such as an iPad or other display. Output video and/or image data may be transmitted by the cable or wireless connection. The proximal hand piece includes a CCD or CMOS optical sensor, for capturing still and/or video images. The imaging device of the present invention enables accurate positioning of the distal end of the elongated body such as within a joint capsule under direct visualization. The imaging device provides a diagnostic function, allowing a clinician or others to effectively diagnose an injury and/or condition. In embodiments, the device can also allow for reliable delivery of therapeutic media into a joint while in a physician's office under local anesthetic, thereby avoiding the need for other diagnostic procedures that may be less accurate and/or require a longer wait period.

In some embodiments, a tissue visualization device comprises:
    a handpiece comprising a visualization sensor configured to collect an image of an internal tissue site;
    at least one lens;
    an elongated body comprising a proximal end and a distal end, the elongated body comprising a lumen configured to deliver a fluid to a tissue site and an optical hypotube;
    an algorithm stored in the handpiece, the algorithm configured to correct optical aberrations in the image of the internal tissue site;
    a distal end comprising a sharpened, deflected tip.

In certain embodiments, the optical correction may be generated by comparing a captured image to a known definition pattern and generating an algorithm that corrects chromatic aberrations and image distortion specific to each individual tissue visualization device. In some embodiments, the optical correction may be unique to an individual tissue visualization device. In particular embodiments, additional information regarding the tissue visualization device may be stored, such as the X,Y position of the center of the lens, the image circle size, and unique characterisitic of the LED so as to provide a consistent initial light level. The aforementioned characteristics of the tissue visualization device and additional characteristics described elsewhere in the specification may be determined during manufacturing and stored in computer memory such as electrically erasable programmable read-only memory (EEPROM). In embodiments, the entirety of the handpiece and the elongated body may be an integrated unit. In certain embodiments, the handpiece further comprises a retraction control, configured to retract the elongated body so as to expose the distal lens of the optical hypotube. In some embodiments, the handpiece may further comprise a luer, configured to conduct fluid to the internal tissue site via the lumen.

In particular embodiments, a method of optical correction comprises:
    focusing a tissue visualization device on a known definition pattern;
    capturing an image of the known definition pattern;
    comparing the image of the known definition pattern to a reference data set corresponding to the known definition pattern;
    generating an algorithm based on the differences between the image of the known definition pattern and the known definition pattern, the algorithm configured to restore the image of the known definition pattern to the parameters of the known definition pattern;
    storing the optical correction within the tissue visualization device; and
    utilizing the optical correction to correct images collected by the tissue visualization device.

In some embodiments, the method may further comprise inserting the tissue visualization device into a tissue site and collecting an image. In certain embodiments, a system for the visualization of a tissue site may comprise: a fully integrated tissue visualization device including a hand piece, image sensor in the hand piece and integrated probe with fiber optics and an infusion lumen; a displayer configured to display images collected by the tissue visualization device; and a cable the provides for electrical communication between the displayer and the tissue visualization device.

In certain embodiments, a sterilized, integrated, one time use disposable tissue visualization device, may comprise:

a handle comprising a visualization sensor;

a monitor configured to display an image;

an elongated body, extending along a longitudinal axis between a proximal end affixed to the handle, and a distal end comprising a laterally deflected, sharpened tip;

an elongate optical element extending through the elongated body, the optical element having a proximal end in optical communication with the visualization sensor and a distal end;

a control on the handle, for axially moving the elongated body between a proximal position in which the sharpened tip is proximal to the distal end of the optical element, and a distal position in which the sharpened tip is distal to the distal end of the optical element;

wherein the distal end of the elongated body is configured to pierce through tissue along the longitudinal axis; and wherein the distal end of the elongate optical element comprises a viewing axis deflected laterally from the longitudinal axis.

In embodiments, the lateral displacement of the sharpened tip is 50% of an outside diameter of the elongated body. The viewing axis may be at a 15 degree angle from the longitudinal axis. The elongate optical element may further comprise a field of view, the field of view comprising a frontward view along the longitudinal axis. In embodiments, the visualization sensor communicates with the monitor wirelessly. The handle may comprise a clamshell shape. The distal end may be laterally deflected via an axially movable control wire. The elongated body may comprise a lumen configured to deliver an anti-inflammatory agent to the internal tissue site. In embodiments, a tissue visualization device may further comprise a rotational sensor, the rotational sensor configured to determine the rotational orientation of the visualization device. The rotational sensor may communicate with the monitor to rotate the image such that a patient reference direction will always appear on the top of the screen. In embodiments, the elongated body may comprise an outer tubular body, wherein the outer tubular body is constructed from a heat-sensitive material.

In certain embodiments, a method of manufacturing a tissue visualization device may comprise:

slicing a tubular reflective material at a desired angle to expose an angled surface;

milling the angled surface until the angled surface is configured to reflect an image;

inserting the tubular reflective material into a tubular body, the tubular body comprising a gap; and positioning the tubular reflective material such that the angled surface reflects light passing through the gap.

In embodiments, an integrated, one time use disposable tissue visualization device may comprise:

a handle;

an elongate rigid tubular probe, extending along a longitudinal axis between a proximal end affixed to the handle, and a distal end having a sharpened tip;

an image sensor in the handle;

an elongate imaging fiber extending through the probe, the imaging fiber having a proximal end in optical communication with the sensor and a distal end;

a control on the handle, for axially moving the tubular probe between a proximal position in which the sharpened tip is proximal to the distal end of the optical element, and a distal position in which the sharpened tip is distal to the distal end of the optical element;

a lens in optical communication with the distal end of the imaging fiber, and a mask on the lens, the mask comprising an annular barrier for blocking visible light, surrounding an optically transparent window for increasing a depth of field perceived by the image sensor.

In embodiments, the distal end of the tubular probe is provided with a lateral deflection. The handle may further comprise an image capture control on the handle. The deflection may be in a first direction relative to the longitudinal axis, and the cord may be attached to the handle at a second direction relative to the longitudinal axis, approximately 180 degrees offset from the first direction. The axial proximal movement of the tubular probe may deflect the distal end of the optical element laterally by at least about 1 degree. In certain embodiments, wherein the lens has an outside diameter of no more than about 0.75 mm and/or 1, no more than about 0.5 mm. In certain embodiments, the window has a diameter within the range of from about 50 microns to about 300 microns. The window may have a diameter within the range of from about 100 microns to about 200 microns.

In embodiments, the lens may comprise a gradient-index optics lens with a flat distal surface. The tissue visualization device may further comprise a plurality of axially extending illumination fibers spaced circumferentially apart around the lens. In some embodiments, the the mask comprises a thin film coating. The mask may comprises a low reflectance chrome coating.e visualization device of claim 1, comprising an annular lumen extending the length of the tubular probe, and positioned in between the imaging fiber and an inside surface of the elongate probe. In certain embodiments, the lumen is in communication with an injection or aspiration port on the handle. The mask may have a transmission of light in the visible range of no more than about 10%. The mask may further have a transmission of light in the visible range of no more than about 5%.

In particular embodiments, a distal end assembly for an elongate viewing instrument, comprises:

an imaging fiber bundle, having a fiber bundle distal end;

a lens, optically coupled to the distal end of the fiber bundle, the lens having a lens distal end;

a non-powered plate, optically coupled to the lens distal end; and a mask in between the lens and the plate, the mask comprising an annular barrier for blocking visible light, surrounding an optically transparent window through the plate for increasing a depth of field perceived by the viewing instrument.

In certain embodiments, the mask is carried by the plate. The mask may comprise a coating applied to the plate. The lens may have an outside diameter of no more than about 0.75 mm or no more than about 0.5 mm. In certain embodiments, the window has a diameter within the range of from about 50 microns to about 300 microns. The window may have a diameter within the range of from about 100 microns to about 200 microns. In certain embodiments, the lens comprises a gradient-index optics lens with a flat distal surface. The distal end of the assembly may further compris a plurality of axially extending illumination fibers spaced circumferentially apart around the lens.

In certain embodiments, a tissue visualization device, comprises:

a handle;

an elongate tubular probe, extending along a longitudinal axis between a proximal end affixed to the handle, and a distal end having a sharpened tip;

an image sensor in the handle;

an elongate imaging fiber extending through the probe, the imaging fiber having a proximal end in optical communication with the sensor and a distal end;

a lens in optical communication with the distal end of the imaging fiber, and a mask in optical communication with the lens, the mask comprising an annular barrier for blocking visible light, surrounding an optically transparent window for increasing a depth of field perceived by the image sensor;

wherein the mask resides in a plane which is spaced apart along an optical path from a focus point for the lens.

The tissue visualization device may further comprise a non-powered optically transmissive plate, and the mask is positioned in between the lens and the plate. The mask may comprises a coating on the plate. The coating may comprise a low transmission and low reflection in the visible range. In certain embodiments, a diameter of the active area of the imaging fiber is at least two times a diameter of the window.

In embodiments, a depth of field enhanced optical assembly for the distal end of an imaging probe may comprise:

a powered lens, having a distal end and an optical path extending therethrough;

a nonpowered plate in the optical path and adjacent the lens distal end; and a mask in between the lens and the plate, the mask comprising an annular barrier for blocking visible light, surrounding an optically transparent window aligned with the optical path.

In embodiments, the lens may comprise a graded index lens. The mask may comprise a low reflective coating on the plate. In certain embodiments, the coating comprises chrome.

BRIEF DESCRIPTION OF THE DRAWINGS

Other features and advantages of the present invention will be apparent from the following detailed description of the invention, taken in conjunction with the accompanying drawings of which:

FIGS. 3A-C illustrate close-up cross-sectional side views of embodiments of the distal end of the tissue visualization device illustrated in FIG. 2A.

FIG. 17 depicts an embodiment of a tissue visualization device.

DETAILED DESCRIPTION OF THE PREFERRED EMBODIMENTS

Figure 1:
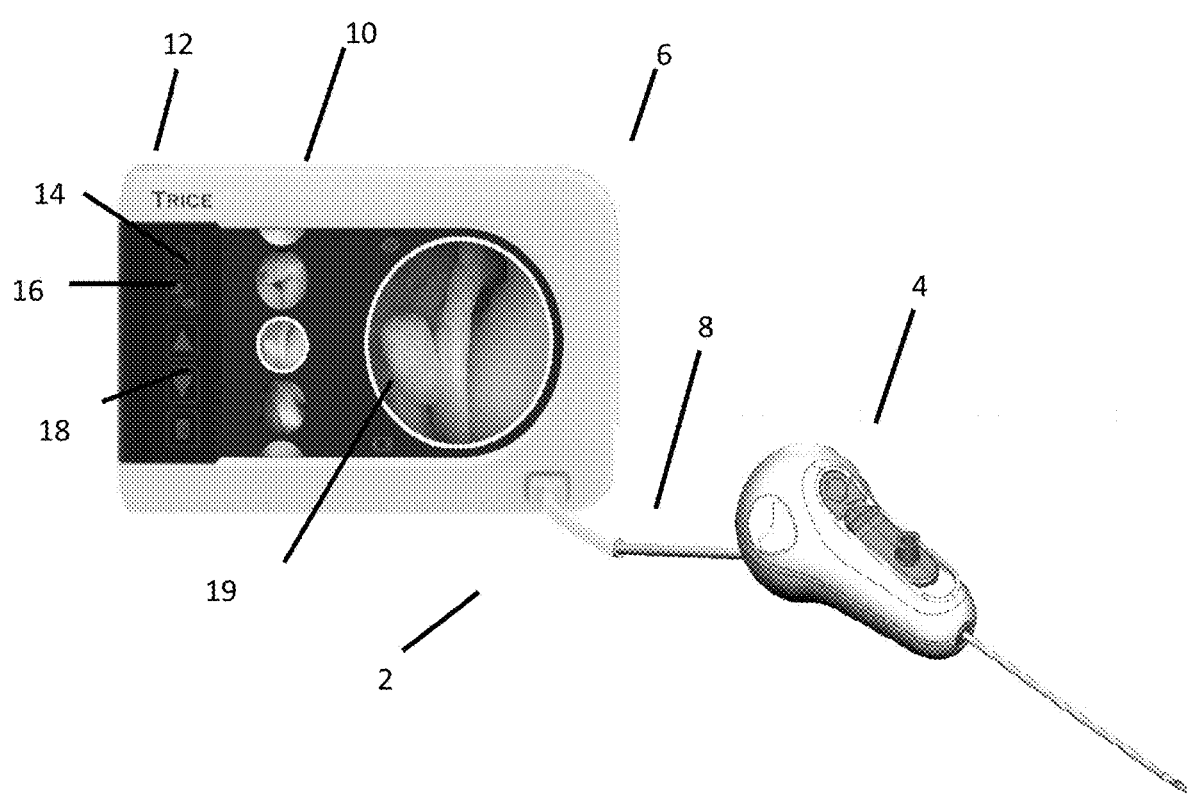
FIG. 1 illustrates an embodiment of a tissue visualization system.

Embodiments disclosed in this section or elsewhere in this application relate to minimally invasive tissue visualization and access systems and devices. Also provided are methods of using the systems in imaging applications, as well as kits for performing the methods. Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the invention include minimally invasive imaging and visualization systems. In some embodiments, imaging systems of the invention are minimally invasive, such that they may be introduced to an internal target site of a patient, for example, a spinal location that is near or inside of an intervertebral disc or an orthopedic joint capsule, through a minimal incision.

In some embodiments, imaging systems of the invention may include both an access device and an elongated body. The access device may be a tubular device having a proximal end and a distal end and an internal passageway extending from the proximal to distal end. Similarly, the elongated body has a proximal end and a distal end and is dimensioned to be slidably moved through the internal passageway of the access device.

In particular embodiments, access devices of the invention are elongated elements having an internal passageway that are configured to provide access to a user (e.g., a health care professional, such as a surgeon) from an extra-corporeal location to an internal target tissue site, e.g., a location near or in the spine or component thereof, e.g., near or in an intervertebral disc, inside of the disc, etc., through a minimally invasive incision. Access devices of the invention may be cannulas, components of retractor tube systems, etc. As the access devices are elongate, they have a length that is 1.5 times or longer than their width, such as 2 times or longer than their width, including 5 or even 10 times or longer than their width, e.g., 20 times longer than its width, 30 times longer than its width, or longer.

In certain embodiments, where the access devices are configured to provide access through a minimally invasive incision, the longest cross-sectional outer dimension of the access devices may (for example, the outer diameter of a tube shaped access device, including wall thickness of the access device, which may be a port or cannula in some instances) range in certain instances from 5 mm to 50 mm, such as 10 to 20 mm. With respect to the internal passageway, this passage can be dimensioned to provide passage of the imaging devices from an extra-corporeal site to the internal target tissue location. In certain embodiments, the longest cross-sectional dimension of the internal passageway, e.g., the inner diameter of a tubular shaped access device, ranges in length from 5 to 30 mm, such as 5 to 25 mm, including 5 to 20 mm, e.g., 7 to 18 mm. Where desired, the access devices are sufficiently rigid to maintain mechanical separation of tissue, e.g., muscle, and may be fabricated from any convenient material. Materials of interest from which the access devices may be fabricated include, but are not limited to: metals, such as stainless steel and other medical grade metallic materials, plastics, and the like.

The systems of the invention may further include an elongated body having a proximal and distal end, where the elongated body is dimensioned to be slidably moved through the internal passageway of the access device or directly through tissue without the use of an additional access device. As this component of the system is elongate, it has a length that is 1.5 times or longer than its width, such as 2 times or longer than its width, including 5 or even 10 times or longer than its width, e.g., 20 times longer than its width, 30 times longer than its width, or longer. When designed for use in knee joint procedures, the elongated body is dimensioned to access the capsule of the knee joint. At least the distal end of the device has a longest cross-sectional dimension that is 10 mm or less, such as 8 mm or less and including 7 mm or less, where in certain embodiments the longest cross-sectional dimension has a length ranging from 5 to 10 mm, such as 6 to 9 mm, and including 6 to 8 mm. The elongated body may be solid or include one or more lumens, such that it may be viewed as a catheter. The term "catheter" is employed in its conventional sense to refer to a hollow, flexible or semi-rigid tube configured to be inserted into a body. Catheters of the invention may include a single lumen, or two or more lumens, e.g., three or more lumens, etc, as desired. Depending on the particular embodiment, the elongated bodies may be flexible or rigid, and may be fabricated from any convenient material.

As summarized above, some embodiments of the invention include visualization sensors and illumination elements. In certain embodiments these visualization sensors are positioned within a handle at the proximal end of the device. The system may include one or more visualization sensors at the proximal end of the device and one or more illumination elements that are located among the distal and/or proximal ends of the elongated body. In particular embodiments, one or more visualization sensors, such as those described in this section or elsewhere in the specification, may be located in the distal end of the device such as within the distal end of the elongated body. In some embodiments, one or more visualization sensors may be located at various locations within the elongated body, such as at approximately one-quarter the length of the elongated body from the distal end, one-half, or three quarters the length of the elongated body from the distal end. In certain embodiments, the visualization sensors may be miniaturized such that they do not substantially increase the outer diameter of the elongated body.

Similarly, with respect to the illumination elements, embodiments of the systems include those systems where one or more illumination elements are located at the distal and/or proximal end of the elongated body. Embodiments of the systems also include those systems where one illumination element is located at the distal and/or proximal end of the elongated body and another illumination element is located at the distal and/or proximal end of the access device. Furthermore, embodiments of the systems include those systems where one or more illumination elements are located at the proximal end of the device and light is propagated via wave guides such as a fiber optic bundle towards the distal end of the device. A longest cross section dimension for the elongated body is generally 20 mm or less, 10 mm or less, 6 mm or less, such as 5 mm or less, including 4 mm or less, and even 3 mm or less.

The elongated body preferably contains an image capture waveguide, an illumination waveguide and a lumen for fluid irrigation or aspiration.

In certain embodiments, miniature visualization sensors have a longest cross-section dimension (such as a diagonal dimension) of 20 mm or less, 10 mm or less, 5 mm or less, or 3 mm or less, where in certain instances the sensors may have a longest cross-sectional dimension ranging from 2 to 3 mm. In certain embodiments, the miniature visualization sensors have a cross-sectional area that is sufficiently small for its intended use and yet retain a sufficiently high matrix resolution. In certain embodiments, miniature visualization sensors may have a longest-cross sectional dimension of 0.5 mm. In some embodiments, the longest cross-sectional dimension is approximately 0.1 mm, 0.2 mm, 0.3 mm, 0.4 mm, or greater than 0.5 mm. In certain embodiments, the visualization sensors may be between 1-2 mm, such as 1.3 mm, or between 0.5-1 mm, such as 0.75 mm. Examples of smaller sized visualization sensors are produced by Fujikura and Medigus. Certain visualization sensors of the may have a cross-sectional area (i.e. an x-y dimension, also known as packaged chip size) that is 2 mm×2 mm or less, such as 1.8 mm×1.8 mm or less, and yet have a matrix resolution of 400×400 or greater, such as 640×480 or greater. In some instances, the visualization sensors have a sensitivity that is 500 mV/Lux-sec or greater, such as 700 mV/Lux-Sec or greater, including 1000 mV/Lux-Sec or greater, where in some instances the sensitivity of the sensor is 2000 mV/Lux-Sec or greater, such as 3000 mV/Lux-Sec or greater. In particular embodiments, the visualization sensors of interest are those that include a photosensitive component, e.g., array of photosensitive elements, coupled to an integrated circuit, where the integrated circuit is configured to obtain and integrate the signals from the photosensitive array and output the analog data to a backend processor. The visualization sensors of interest may be viewed as integrated circuit image sensors, and include complementary metal-oxide-semiconductor (CMOS) sensors and charge-coupled device (CCD) sensors. In certain embodiments, the visualization sensors may further include a lens positioned relative to the photosensitive component so as to focus images on the photosensitive component.

Visualization sensors of interest include, but are not limited to, those obtainable from: OminVision Technologies Inc., Sony Corporation, Cypress Semiconductors. The visualization sensors may be integrated with the component of interest, e.g., the proximal handle or the elongated structure or both. In some embodiments, as the visualization sensor(s) is integrated at the proximal end of the component, it cannot be removed from the remainder of the component without significantly compromising the structure of component. As such, the integrated visualization sensor may not be readily removable from the remainder of the component, such that the visualization sensor and remainder of the component form an inter-related whole. As described above, in some embodiments, the visualization sensor(s) may be located at the distal end of the elongated body or elsewhere along the elongated body.

While any convenient visualization sensor may be employed in devices of the invention, in certain instances the visualization sensor may be a CMOS sensor. For example, the CMOS sensor may be an Aptina CMOS sensor such as the APtina MT9V124. Such a CMOS sensor may provide very small pixels, with small package sizes coupled with low-voltage differential signaling (LVDS). Such a CMOS sensor allows the cable to the display to comprise less conductors, and thus may allow for reduced cable costs as compared to other options. Of additional interest as CMOS sensors are the OmniPixel line of CMOS sensors available from OmniVision (Sunnyvale, Calif.), including the OmniPixel, OmniPixel2, OmniPixel3, OmniPixel3-HS and OmniBSI lines of CMOS sensors. These sensors may be either frontside or backside illumination sensors. Aspects of these sensors are further described in one or more the following U.S. patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

In certain embodiments, the elongated body may further include one or more infusion lumens that run at least the substantial length of the device, e.g., for performing a variety of different functions. In certain embodiments where it is desired to flush (i.e., wash) the location of the target tissue at the distal end of the elongated body and remove excess fluid, the elongated body may include both an irrigation and aspiration lumen. During use, the irrigation lumen is operatively connected to a fluid source (e.g., physiologically acceptable fluid, such as saline) at the proximal end of the device, where the fluid source is configured to introduce fluid into the lumen under positive pressure, e.g., at a pressure ranging from 0 to 500 mm Hg, so that fluid is conveyed along the irrigation lumen and out the distal end. While the dimensions of the irrigating lumen may vary, in certain embodiments the longest cross-sectional dimension of the irrigation lumen ranges from 1 to 3 mm. During use, the aspiration lumen is operatively connected to a source of negative pressure (e.g., vacuum source) at the proximal end of the device, where the negative pressure source is configured to draw fluid from the tissue location at the distal end into the irrigation lumen under positive pressure, e.g., at a pressure ranging from 50 to 600 mm Hg, so that fluid is removed from the tissue site and conveyed along the irrigation lumen and out the proximal end, e.g., into a waste reservoir. While the dimensions of the aspiration lumen may vary, in certain embodiments the longest cross-sectional dimension of the aspiration lumen ranges from about 1 to 10 mm, about 1 to 4 mm, about 1 to 3 mm, or less than 1 mm. Alternatively, a single lumen may be provided, through which irrigation and/or aspiration may be accomplished. In embodiments, the product packaging may include a single port stopcock as a means to control fluid flow. In particular embodiments, the stopcock or suitable valve may be directly integrated into the device. In further embodiments, more than one port or stopcock may be used, such as two ports and two stopcocks, three ports and three stopcocks, and so on. In some embodiments, a three way stopcock may be provided so a clinician can 'toggle' between infusion and aspiration, or infusion of a first and second fluid, without connecting and reconnecting tubes.

In certain embodiments, the systems of the invention are used in conjunction with a controller configured to control illumination of the illumination elements and/or capture of images (e.g., as still images or video output) from the visualization sensors. This controller may take a variety of different formats, including hardware, software and combinations thereof. The controller may be physically located relative to the elongated body and/or access device at any convenient location such as at the proximal end of the system. In certain embodiments, the controller may be distinct from the system components, i.e., elongated body, such that a controller interface is provided that is distinct from the proximal handle, or the controller may be integral with the proximal handle.

FIG. 1 illustrates an embodiment of a system 2 for the visualization of an interior tissue site. In some embodiments, a tissue visualization system 2 comprises: a tissue visualization device 4, described in much greater detail below, a controller 6, and a cable 8 that provides electrical communication between the controller 6 and the tissue visualization device 4.

In certain embodiments, the controller 6 may comprise a housing having a memory port such as an SD card slot 10 and a camera button 12. The camera button 12 may activate the system to collect and store a still or moving image. The controller 6 may further comprise a power button 14, a mode switch button 16, and brightness controls 18. The controller 6 can further comprise a display such as a screen 19 for displaying still images and/or video.

Activating the mode switch button 10 may switch the system between different modes such as a procedure mode in which video and/or still images are collected and displayed in real-time on the video screen 19 and a consultation mode, in which a clinician may selectively display stored images and video on the video screen 19 for analysis. For example, while in procedure mode, the system could display video or images from the visualization sensor in real-time. By real-time, it is meant that the screen 19 can show video of the interior of a tissue site as it is being explored by the clinician. The video and/or images can further be stored automatically by the system for replay at a later time. For another example, while in consult mode, the screen 19 may conveniently display specific images or videos that have previously been acquired by the system, so that the clinician can easily analyze the collected images/data, and discuss the images and data with a patient. In some embodiments, the clinician may be able to annotate the images via a touch screen or other suitable means.

In certain embodiments, the screen 19 may be any type of image plane suitable for visualizing an image, such as the screen on an iPad, a camera, a computer monitor, cellular telephone or a display carried by a head worn support such as eyeglasses or other heads up display. In certain embodiments, the cable may be avoided by configuring the device and display to communicate wirelessly.

In some embodiments, it may be desirable to remove the cord and provide instead a wireless communication link between the probe and the monitor and possibly also to a centralized medical records storage and/or evaluation location. Local transmission such as to the monitor within a medical suite may be accomplished via a local area network such as, for example, a "WiFi" network based on IEEE 802.11 wireless local area networking standards, Bluetooth wireless personal area networking standard, or the low power consumption ANT wireless protocol. Transceiver chips and associated circuitry are well understood in the art, and may be located within the hand piece housing of the visualization device 4, which is discussed below.

As a further alternative to conventional WiFi or IEEE 801.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. As compared to present IEEE 802.15.1 BLUETOOTH wireless personal area networks, for example, ZIGBEE networks provide the advantage of operating with low power requirements (enabling, for example, ZIGBEE transceivers to be integrally coupled to the probe under battery power). However, transmission ranges between individual ZIGBEE transceivers are generally limited to no more than several hundred feet. As a consequence, such networks are suitable for on-site communications with medical devices, but unusable for centralized monitoring locations located off-site. Therefore, a hybrid system may be desirable in which one or more wireless personal area networks are configured to facilitate on-site communications between the probe and associated monitor, and also between the probe and one or more wireless relay modules which are further configured to communicate with off-site centralized monitoring systems (for example, via internet connection or a wireless wide-area network (WWAN) such as a mobile telephone data network, for example, based on a Global System for Mobile Communications (GSM) or Code Division Multiple Access (CDMA) cellular network or associated wireless data channels). Suitable relay modules and systems are respectively described in patent applications entitled "Wireless Relay Module for Remote Monitoring Systems" (U.S. application Ser. No. 13/006,769, filed Jan. 14, 2011) and "Medical Device Wireless Network Architectures" (U.S. application Ser. No. 13/006,784, filed Jan. 14, 2011) which are hereby incorporated by reference within this patent application.

Thus any of the probes disclosed herein may be provided with an interface circuit that includes a transceiver having one or more of a transmitter and/or a receiver for respectively transmitting and receiving video image, still image and potentially other signals with the associated monitor within the medical suite over a wireless network such as, for example, a Low-Rate Wireless Personal Area Networks or "LR-WPAN," ZIGBEE network or another low-power personal area network such as a low power BLUETOOTH or other WiFi network, existing or subsequently developed.

Optionally also provided within the patient facility are one or more relay modules. Each relay module includes a first transceiver for receiving signals from and transmitting signals to the interface circuit within a hand probe or the associated monitor, and further includes an output such as an internet connection or a second transceiver for wirelessly transmitting signals to and receiving signals from an access point via a wireless wide-area network ("WWAN"). Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). For compliance with any applicable patient data privacy provisions of the Health Insurance Portability and Accountability Act of 1996 (HIPAA), communications over each of the facility-oriented wireless network and WWAN are preferably conducted securely using, for example, using a Secure Sockets Layer (SSL) protocol or a Transport Layer Security (TLS) protocol.

Also provided are kits for use in practicing the subject methods, where the kits may include one or more of the above devices, and/or components of the subject systems, as described above. As such, a kit may include a visualization device and a cable for connection to a controller, contained within a sterile package. The kit may further include other components, e.g., a controller, guidewires, stylets, etc., which may find use in practicing the subject methods. Various components may be packaged as desired, e.g., together or separately. Preferably, the components within the package are pre-sterilized. Further details regarding pre-sterilization of packaging may be found in U.S. Pat. No. 8,584,853, filed Feb. 16, 2013, and hereby incorporated by reference into this specification.

In addition to above mentioned components, the subject kits may further include instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also of interest is programming that is configured for operating a visualization device according to methods of invention, where the programming is recorded on physical computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a storage medium having instructions for operating a minimally invasive in accordance with the invention.

In some embodiments, programming of the device includes instructions for operating a device of the invention, such that upon execution by the programming, the executed instructions result in execution of the imaging device to: illuminate a target tissue site, such as an orthopedic joint or portion thereof; and capture one or more image frames of the illuminated target tissue site with the visualization sensor.

Visualization sensors of interest are those that include a photosensitive component, e.g., array of photosensitive elements that convert light into electrons, coupled to an integrated circuit. The integrated circuit may be configured to obtain and integrate the signals from the photosensitive array and output image data, which image data may in turn be conveyed to an extra-corporeal display configured to receive the data and display it to a user. The visualization sensors of these embodiments may be viewed as integrated circuit image sensors.

The integrated circuit component of these sensors may include a variety of different types of functionalities, including but not limited to: image signal processing, memory, and data transmission circuitry to transmit data from the visualization sensor to an extra-corporeal location, etc. The miniature visualization sensors may further include a lens component made up of one or more lenses positioned relative to the photosensitive component so as to focus images on the photosensitive component. Where desired, the one or more lenses may be present in a housing. Specific types of miniature visualization sensors of interest include complementary metal-oxide-semiconductor (CMOS) sensors and charge-coupled device (CCD) sensors. The sensors may have any convenient configuration, including circular, square, rectangular, etc. Visualization sensors of interest may have a longest cross-sectional dimension that varies depending on the particular embodiment, where in some instances the longest cross sectional dimension (e.g., diameter) is 10.0 mm or less, such as 6.0 mm or less, including 3.0 mm or less.

Visualization sensors of interest may be either frontside or backside illumination sensors, and have sufficiently small dimensions while maintaining sufficient functionality to be integrated at the proximal end of the elongated bodies within the hand piece of the devices of the invention. Aspects of these sensors are further described in one or more the following U.S. Patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

The distal end of the elongated body may be configured for front viewing and/or side-viewing, as desired. In yet other embodiments, the elongated body may be configured to provide image data from both the front and the side, e.g., where the primary viewing axis from the distal end of the waveguide extends at an angle that is greater than about 2° or 5° or 10° or 15° or more relative to the longitudinal axis of the elongated body, described in greater detail below.

Depending on the particular device embodiment, the elongated body may or may not include one or more lumens that extend at least partially along its length. When present, the lumens may vary in diameter and may be employed for a variety of different purposes, such as irrigation, aspiration, electrical isolation (for example of conductive members, such as wires), as a mechanical guide, etc., as reviewed in greater detail below. When present, such lumens may have a longest cross section that varies, ranging in some in stances from 0.5 to 5.0 mm, such as 1.0 to 4.5 mm, including 1.0 to 4.0 mm. The lumens may have any convenient cross-sectional shape, including but not limited to circular, square, rectangular, triangular, semi-circular, trapezoidal, irregular, etc., as desired. These lumens may be provided for a variety of different functions, including as irrigation and/or aspiration lumens, as described in greater detail below.

In certain embodiments, the devices may include one or more illumination elements configured to illuminate a target tissue location so that the location can be visualized with a visualization sensor, e.g., as described above. A variety of different types of light sources may be employed as illumination elements, so long as their dimensions are such that they can be positioned at or carry light to the distal end of the elongated body. The light sources may be integrated with a given component (e.g., elongated body) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an inter-related whole. The light sources may be light emitting diodes configured to emit light of the desired wavelength range, or optical conveyance elements, e.g., optical fibers, configured to convey light of the desired wavelength range from a location other than the distal end of the elongated body, e.g., a location at the proximal end of the elongated body within the hand piece, to the distal end of the elongated body.

As with the visualization sensors, the light sources may include a conductive element, e.g., wire, or an optical fiber or bundle, which runs the length of the elongated body to provide for power and control of the light sources from a location outside the body, e.g., an extracorporeal control device.

Where desired, the light sources may include a diffusion element to provide for uniform illumination of the target tissue site. Any convenient diffusion element may be employed, including but not limited to a translucent cover or layer (fabricated from any convenient translucent material) through which light from the light source passes and is thus diffused. In those embodiments of the invention where the system includes two or more illumination elements, the illumination elements may emit light of the same wavelength or they may be spectrally distinct light sources, whereby "spectrally distinct" is meant that the light sources emit light at wavelengths that do not substantially overlap, such as white light and infra-red light. In certain embodiments, an illumination configuration as described in U.S. application Ser. Nos. 12/269,770 and 12/269,772 (the disclosures of which are herein incorporated by reference) is present in the device.

In some embodiments, devices of the invention may include a linear mechanical actuator for linearly translating a distal end element of the device, such as a tubular needle which surrounds a visualization element relative to the visualization element. By "linearly translating" is meant moving the along a substantially straight path. As used herein, the term "linear" also encompasses movement in a non-straight (i.e., curved) path.

In some embodiments, an integrated articulation mechanism that imparts steerability to the distal end of the elongated body and/or distal end of the visualization element is also present in the device. By "steerability" is meant the ability to maneuver or orient the visualization element, tissue modifier and/or distal end of the elongated body as desired during a procedure, e.g., by using controls positioned at the proximal end of the device. In these embodiments, the devices include a steerability mechanism (or one or more elements located at the distal end of the elongated body) which renders the desired distal end component maneuverable as desired through proximal end control. As such, the term "steerability", as used herein, refers to a mechanism that provides a user steering functionality, such as the ability to change direction in a desired manner, such as by deflecting the primary viewing axis left, right, up or down relative to the initial axial direction.

The steering functionality can be provided by a variety of different mechanisms. Examples of suitable mechanisms include, but are not limited to one or more axially moveable pull or push wires, tubes, plates, meshes or combinations thereof, made from appropriate materials, such as shape memory materials, music wire, etc. For example, one active deflection mechanism includes providing a plurality of transverse slots spaced apart axially along a first side of the outer tubular body 1126 within the distal segment 1108. A second side of the outer tubular body 1126 within the distal segment 1108, opposite from (i.e., 180° from) the first side acts as an axially non-compressible spine, while the first side may be compressed axially causing a lateral deflection concave in the direction of the first side. Axial compression (or elongation) of the first side relative to the second side, to induce or remove curvature, may be accomplished by an axially movable control wire. The distal end of the control wire may be secured to the outer tubular body 1126 within the distal segment 1108, preferably at the distal end of the distal segment 1108. The control wire extends proximally throughout the length of the outer tubular body 1126, to a proximal deflection control. Manipulation of the control to retract the control wire proximally will collapse the transverse slots, shortening the axial length of the first side relative to the second side, thereby deflecting the distal segment 1108.

In some instances, the distal end of the elongated body is provided with a distinct, additional capability that allows it to be independently rotated about its longitudinal axis when a significant portion of the operating handle is maintained in a fixed position, as discussed in greater detail below.

The extent of distal primary viewing axis articulations of the invention may vary, such as from at least about 5°, 10°, 25°, or 35° or more from the primary viewing axis. The visualization element may be configured for rotating about its axis so that the full range of angles is accessible on either side of the axis of the probe, essentially multiplying the effective viewing angle e.g., as described in greater detail below. Articulation mechanisms of interest are further described in published PCT Application Publication Nos. WO 2009029639; WO 2008/094444; WO 2008/094439 and WO 2008/094436; the disclosures of which are herein incorporated by reference. Specific articulation configurations of interest are further described in connection with the figures, below.

In certain embodiments, devices of the invention may further include an irrigator and aspirator configured to flush an internal target tissue site and/or a component of the device, such as a lens of the visualization sensor. As such, the elongated body may further include one or more lumens that run at least the substantial length of the device, e.g., for performing a variety of different functions, as summarized above. In certain embodiments where it is desired to flush (i.e., wash) the target tissue site at the distal end of the elongated body (e.g. to remove ablated tissue from the location, etc.), the elongated body may include both irrigation lumens and aspiration lumens. Thus, the tissue modification device can comprise an irrigation lumen extending axially through the elongated body. During use, the irrigation lumen may be operatively connected to a fluid source (e.g., a physiologically acceptable fluid, such as saline) at the proximal end of the device, where the fluid source is configured to introduce fluid into the lumen under positive pressure, e.g., at a pressure ranging from 0 psi to 60 psi, so that fluid is conveyed along the irrigation lumen and out the distal end. While the dimensions of the irrigation lumen may vary, in certain embodiments the longest cross-sectional dimension of the irrigation lumen ranges from 0.5 mm to 5 mm, such as 0.5 mm to 3 mm, including 0.5 mm to 1.5 mm.

During use, the aspiration lumen may be operatively connected to a source of negative pressure (e.g., a vacuum source) at the proximal end of the device. While the dimensions of the aspiration lumen may vary, in certain embodiments the longest cross-sectional dimension of the aspiration lumen ranges from 1 mm to 7 mm, such as 1 mm to 6 mm, including 1 mm to 5 mm. In some embodiments, the aspirator comprises a port having a cross-sectional area that is 33% or more, such as 50% or more, including 66% or more, of the cross-sectional area of the distal end of the elongated body.

In some instances, the negative pressure source is configured to draw fluid and/or tissue from the target tissue site at the distal end into the aspiration lumen under negative pressure, e.g., at a negative pressure ranging from 300 to 600 mmHg, such as 550 mmHg, so that fluid and/or tissue is removed from the tissue site and conveyed along the aspiration lumen and out the proximal end, e.g., into a waste reservoir. In certain embodiments, the irrigation lumen and aspiration lumen may be separate lumens, while in other embodiments, the irrigation lumen and the aspiration functions can be accomplished in a single lumen.

In certain embodiments, the devices may include a control structure, such as a handle, operably connected to the proximal end of the elongated body. By "operably connected" is meant that one structure is in communication (for example, mechanical, electrical, optical connection, or the like) with another structure. When present, the control structure (e.g., handle) is located at the proximal end of the device. The handle may have any convenient configuration, such as a hand-held wand with one or more control buttons, as a hand-held gun with a trigger, etc., where examples of suitable handle configurations are further provided below.

In some embodiments, the distal end of the elongated body is rotatable about its longitudinal axis when a significant portion of the operating handle is maintained in a fixed position. As such, at least the distal end of the elongated body can turn by some degree while the handle attached to the proximal end of the elongated body stays in a fixed position. The degree of rotation in a given device may vary, and may range from 0 to 360°, such as 0 to 270°, including 0 to 180°.

As described herein this section and elsewhere in the specification, in certain embodiments, the device may be disposable or reusable. As such, devices of the invention may be entirely reusable (e.g., be multi-use devices) or be entirely disposable (e.g., where all components of the device are single-use). In some instances, the device can be entirely reposable (e.g., where all components can be reused a limited number of times). Each of the components of the device may individually be single-use, of limited reusability, or indefinitely reusable, resulting in an overall device or system comprised of components having differing usability parameters.

As described herein this section and elsewhere in the specification, in certain embodiments, devices of the invention may be fabricated using any convenient materials or combination thereof, including but not limited to: metallic materials such as tungsten, stainless steel alloys, platinum or its alloys, titanium or its alloys, molybdenum or its alloys, and nickel or its alloys, etc.; polymeric materials, such as polytetrafluoroethylene, polyimide, PEEK, and the like; ceramics, such as alumina (e.g., STEATITE™ alumina, MAECOR™ alumina), etc. In some embodiments, materials that provide both structural as well as light piping properties may be used.

With respect to imaging the interior of a joint capsule, methods include positioning a distal end of the visualization element of the invention in viewing relationship to the target tissue. By viewing relationship is meant that the distal end is positioned within 40 mm, such as within 10 mm, including within 5 mm of the target tissue site of interest. Positioning the distal end of the viewing device in relation to the desired target tissue may be accomplished using any convenient approach, including direct linear advance from a percutaneous access point to the target tissue. Following positioning of the distal end of the imaging device in viewing relationship to the target tissue, the target tissue is imaged through use of the illumination elements and visualization sensors to obtain image data. Image data obtained according to the methods of the invention is output to a user in the form of an image, e.g., using a monitor or other convenient medium as a display means. In certain embodiments, the image is a still image, while in other embodiments the image may be a video.

In embodiments, the internal target tissue site may vary widely. Internal target tissue sites of interest include, but are not limited to, orthopedic joints, cardiac locations, vascular locations, central nervous system locations, etc. In certain cases, the internal target tissue site comprises spinal tissue. Orthopedic joints may comprise any type of joint of interest within the human body, such as the knee or the shoulder. In some embodiments, the internal tissue site may comprise sites of interest during general surgery, such as abdominal organs and/or surrounding tissues.

Further applications of the tissue visualization devices described herein this section or elsewhere in the specification include use in general surgery (laparoscopic or other minimally invasive surgery) as a secondary visualization device. In some instances, the laparoscopic camera may need to be removed and the procedure is blind. However, the outer diameters of the devices described herein this application are small enough that they can be used to eliminate blackout once a laparoscopic camera is removed. In such embodiments, the elongated body is no longer rigid, instead the body is flexible and can be mounted in an elongated flexible tubular body with any of a variety of steering mechanisms such as one or two or three or more pull wires to deflect the distal end. In some embodiments, the device may comprise a biased curved distal end (e.g., Nitinol) that can be selectively curved or straightened by retracting an outer straight sleeve or internal straightening wire, etc.

Beyond general surgery and the other applications described herein this section and elsewhere in the specification, embodiments of the visualization devices described herein can be utilized in ear, nose, and throat applications. For example, the devices described herein may be used in any diagnostic evaluation where visualization may be valuable. As another example, the devices described herein may also be used to guide or evaluate the treatment of chronic sinusitis, for instance, the dilatation of a sinus such as the maxillary sinus.

In some embodiments, the subject devices and methods find use in a variety of different applications where it is desirable to image and/or modify an internal target tissue of a subject while minimizing damage to the surrounding tissue. The subject devices and methods find use in many applications, such as but not limited to surgical procedures, where a variety of different types of tissues may be visualized and potentially treated, including but not limited to; soft tissue, cartilage, bone, ligament, etc. Additional methods in which the imaging devices find use include those described in United States Published Application No. 2008/0255563.

In one embodiment, the imaging device is utilized to accurately position the distal end of a needle within the joint capsule in, for example, a knee. This enables injection of therapeutic media into the capsule on a reliable basis. For this application, the outside diameter of the tubular body has a diameter of less than about 3 mm, preferably less than about 2.5 mm and, in one implementation, approximately 2.1 mm (14 gauge).

Figure 2A:
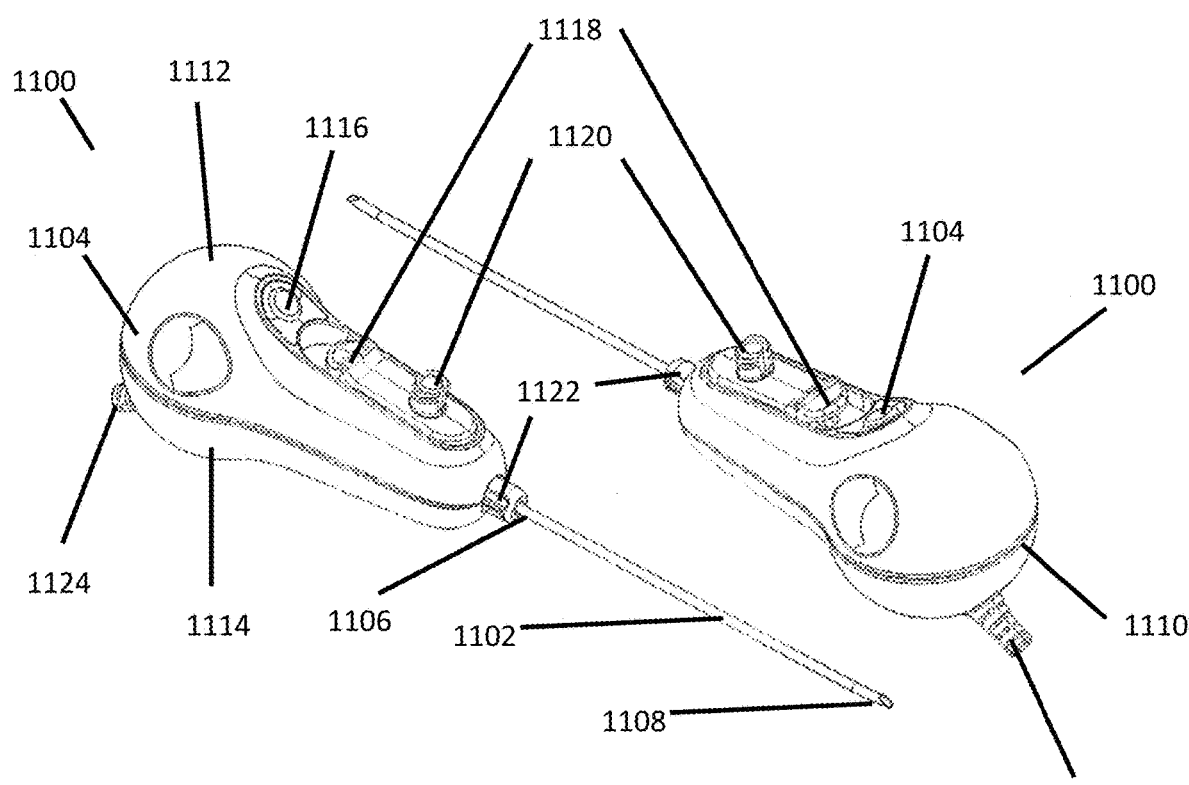
FIGS. 2A-C illustrate various embodiments of a tissue visualization device.

FIG. 2A illustrates an embodiment of a tissue visualization device 1100, comprising an elongated body 1102 and a handpiece 1104. The elongated body may have a length that is at least around 1.5 times longer than its width, at least around 2 times longer than its width, at least around 4 times longer than its width, at least around 10 times or longer than its width, at least around 20 times longer than its width, at least around 30 times longer than its width, at least around 50 times longer than its width, or longer than 50 times the width. The length of the elongated body may vary, and in some instances may be at least around 2 cm long, at least around 4 cm long, at least 6 cm long, at least 8 cm long, at least 10 cm long, at least 15 cm long, at least 20 cm long, at least 25 cm, at least 50 cm, or longer than 50 cm. The elongated body may have the same outer cross-sectional dimensions (e.g., diameter) along the entire length. Alternatively, the cross-sectional diameter may vary along the length of the elongated body. In certain embodiments, the outer diameter of the elongated body is approximately 0.1 to 10 mm, approximately 0.5 mm to 6 mm, approximately 1 mm to 4 mm, approximately 1.5 mm to 3 mm, approximately 2 mm to 2.5 m, or approximately 2.1 mm. In certain embodiments, the elongated body is a 14 gauge needle, having an OD of about 2.1 mm and a ID of about 1.6 mm.

In certain embodiments, and as described elsewhere in the specification, the elongated body may have a proximal end 1106 and a distal end 1108. The term "proximal end", as used herein, refers to the end of the elongated body that is nearer the user (such as a physician operating the device in a tissue modification procedure), and the term "distal end", as used herein, refers to the end of the elongated body that is nearer the internal target tissue of the subject during use. The elongated body is, in some instances, a structure of sufficient rigidity to allow the distal end to be pushed through tissue when sufficient force is applied to the proximal end of the elongated body. As such, in these embodiments the elongated body is not pliant or flexible, at least not to any significant extent. In certain embodiments, the distal end 1108 can further comprise a sharpened tip as depicted in FIG. 2A, allowing the distal end to pierce through tissue such as a joint capsule. In certain embodiments, the distal end may be pushed from the exterior of the body into the joint capsule, by piercing through the skin and underlying tissues.

As depicted in FIG. 2A, in embodiments, the handpiece may have a rounded "clamshell" shape comprising a seam 1110 connecting a clamshell top 1112 and a clamshell bottom 1114. In some embodiments, the clamshell top 1112 and bottom 1114 and can be manufactured in two pieces and then attached together at the seam 1110. The rounded clamshell shape provides a comfortable and ergonomic handle for a user to hold while using the device. In certain embodiments and as will be described in greater detail later, the handpiece may comprise an image capture control such as a button 1116 configured to capture a desired image. In further embodiments, the image capture control may comprise a switch, dial, or other suitable mechanism. The handpiece 104 may further comprise a retraction control 1118 that retracts or extends a portion of the elongated body 1102 such as a sharpened needle. The retraction control will be described in greater detail in relation to FIGS. 2B-C and later Figures.

In certain embodiments, the control 1116 may selectively activate the acquisition of an image and/or video. The control 1116 may thus be configured to selectively start video recording, stop video recording, and/or capture a still image either during video recording or while video recording is off. In some embodiments, the control or another control may turn on/off an ultraviolet light (UV) source that would be used with UV sensitive material such as a gel. For example, a UV-sensitive liquid could be delivered to a target tissue, such as the knee, followed by application of UV liquid to solidify the liquid into a solid or semi-solid material. UV light may be generated via a standard LED, such as those described elsewhere in the specification. The UV light could be directed towards the target tissue via illumination fibers such as those described elsewhere in the specification, while still retaining some illumination fibers to illuminate the target tissue for the purposes of imaging.

In embodiments, the handpiece may comprise a luer connection 1120, configured to connect to any fluid source as described herein this section or elsewhere in this specification, such as sterile saline. The luer connection 1120 may be in fluid communication with a lumen extending throughout the length of the elongated body, allowing for the delivery of fluid or agents to the tissue site.

The junction between the handpiece 1104 and the elongated body 1102 may include a hub 1122 that connects the handpiece 1104 to the elongated body 1102. In some embodiments, the hub may be detachable, allowing the elongated body to be detached from the handpiece. In other embodiments, the elongated body is permanently attached to the handpiece via the hub to provide an integrated assembly.

The handpiece may further comprise a strain relief node 1124, configured to attach to an electrical cable (not shown in FIG. 2A). The strain relief node 1124 can serve to reduce strain on electrical wiring that may be in electrical communication with the handpiece.

In some embodiments, the tissue visualization device 1100 is configured as an integrated assembly for one time use. In certain embodiments, the tissue visualization device 1100 is pre-sterilized, thus the combination of integration and pre-sterilization allows the tissue visualization device to be ready for use upon removal from the packaging. Following use, it may be disposed. Thus the handpiece 1104, elongated body 1102, and other components, such as the cable, may be all one integrated unit. By one integrated unit, it is meant that the various portions described above may be attached together as one single piece not intended for disassembly by the user. In some embodiments, the various portions of the integrated unit are inseparable without destruction of one or more components. In some embodiments, the display, as described herein this section or elsewhere in the specification, may also be incorporated and sterilized as part of a single integrated tissue visualization device.

Figure 2B:
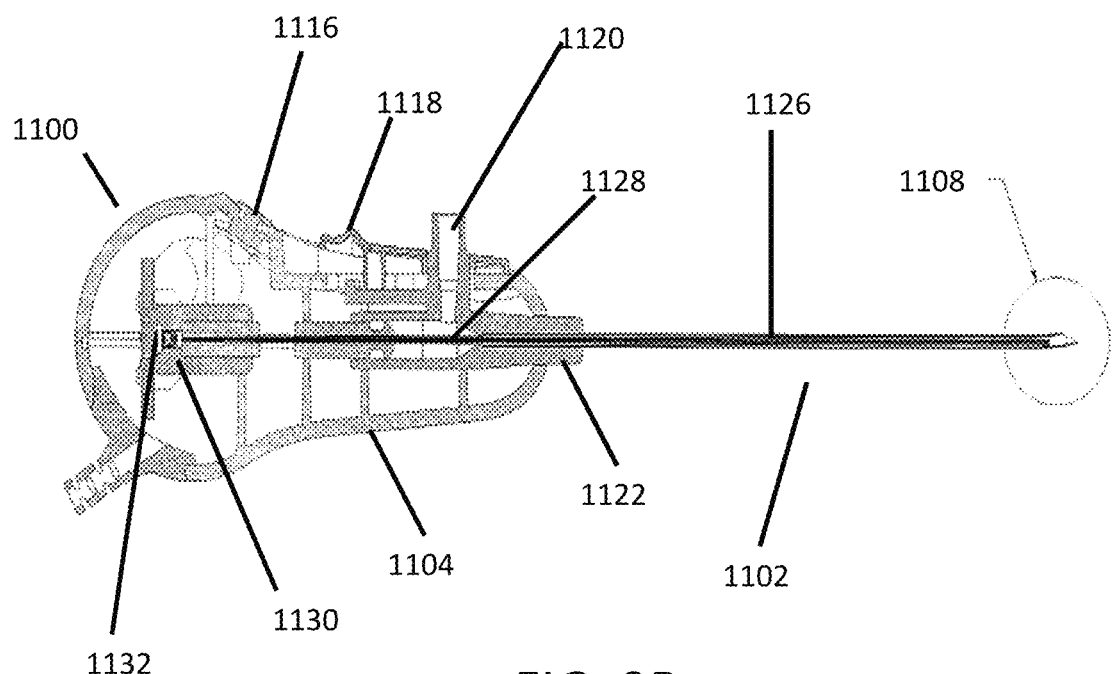

FIG. 2B illustrates a cross-sectional side view of an embodiment of the tissue visualization device depicted in FIG. 2A. As in FIG. 2A, the tissue visualization device comprises a number of components such as an image capture trigger 1116, retraction control 1118, luer 1120, elongated body 1102, handpiece 1104, and hub 1122.

In some embodiments, the distal end 1108 may comprise a deflected configuration, in which the distal end of the elongated body inclines away from the longitudinal axis of the elongated body 1102. This deflected tip is preferably sharpened, allowing the tip to penetrate a tissue site of interest. The deflected tip embodiment of the distal end 1108 will be described below in greater detail in relation to FIGS. 3A-B. In embodiments, the tip is capable of penetrating through the skin and other tissues to reach an internal tissue site.

Figure 3A:
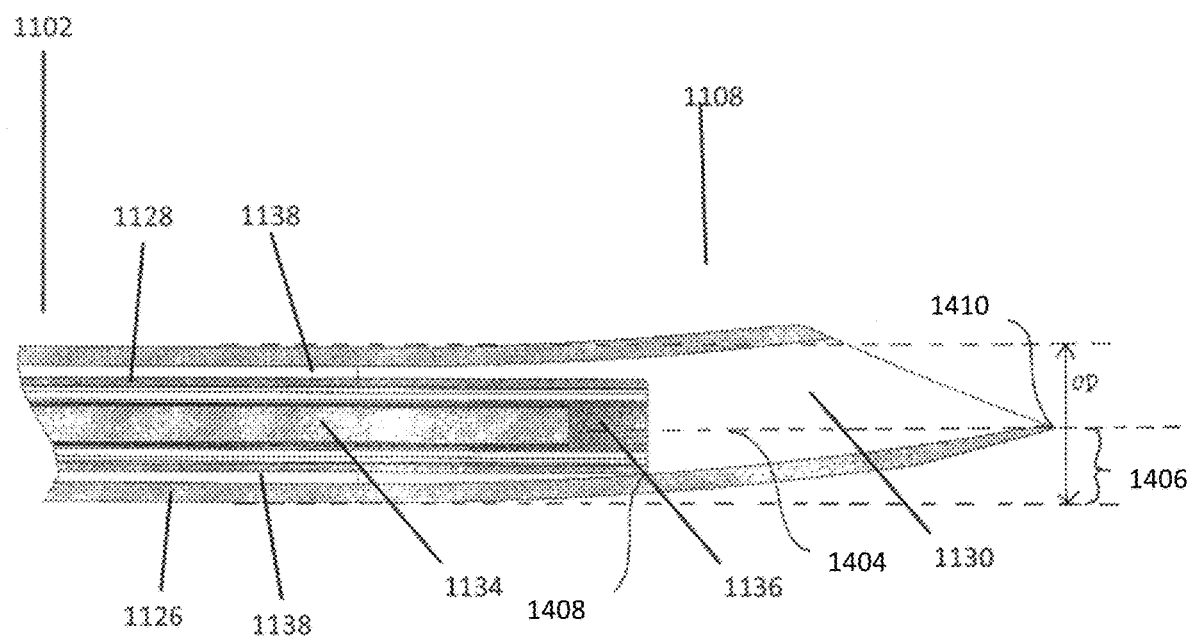

As can now be seen in FIG. 3A, the elongated body 1102 comprises an outer tubular body 1126 which may be a hypodermic needle such as a 14 gauge needle with a sharpened tip. The visualization element is in the form of an inner optical hypotube 1128 extending concentrically through the outer tubular body 1126. The optical hypotube can act to transmit an image of a tissue site to a visualization sensor 1132 (FIG. 2B) such as those described herein this section and elsewhere in the specification. The handpiece 1104 further comprises a proximal lens housing 1130, described in more detail below in FIG. 7.

In certain embodiments, as described elsewhere, the distal end of the visualization element may comprises one or more visualization sensors 1350, such as any visualization sensor or imaging sensor described herein this section or elsewhere in the specification. In certain embodiments, one or more visualization sensors may be position on the inner diameter of the outer tubular body. In embodiments where one or more visualization sensors is positioned on the inner diameter of the outer tubular body, the visualization sensor may be positioned in such a manner as to allow the sensor an angled field of view out of the end of the outer tubular body, for example at optional position 1352. In some embodiments, the visualization sensor may be positioned on the inner diameter of the outer tubular body, opposite the sharpened tip. The sensor may also be positioned at any suitable location on the interior of the outer tubular body to provide a field of view through the distal openeing of the outer tubular body.

Figure 2C:
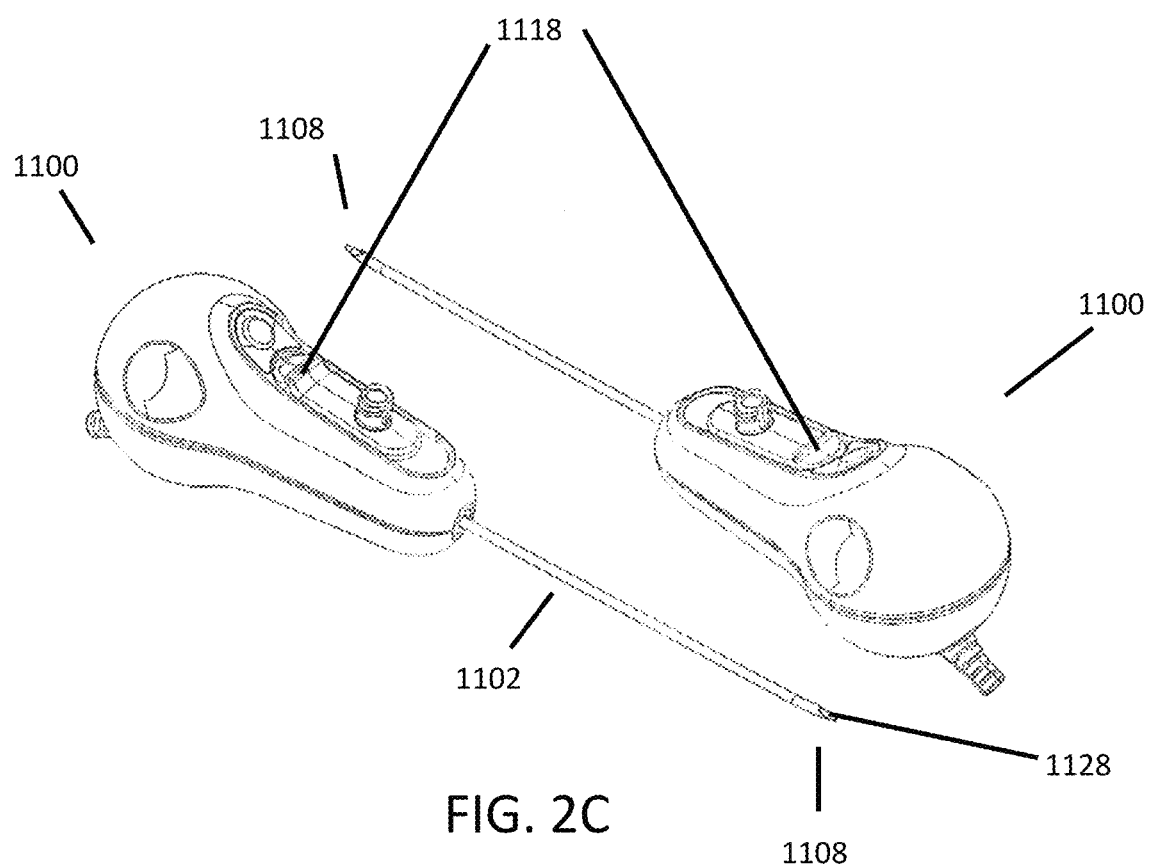

Referring to FIGS. 2C and 3A, as described above, in some embodiments the handpiece may comprise a retraction control 1118. The retraction control can serve to retract the outer tubular body 1126 of FIG. 3A, relative to the optical hypotube, thus allowing the optical hypotube to extend beyond the front opening of the outer tubular body at the distal end 1108. See FIG. 3B. In some embodiments, the sharpened distal end is used to pierce the tissue to direct the elongated body into the target area. Once the elongated body has reached the target area, such as within the joint capsule the retraction control 118 can then be used to retract the sharpened tip proximally of the distal end of the visualization element. By retracting the sharpened tip, the user may direct the now blunt distal end of the elongated body within a tissue site without risk of piercing the tissue again. Retraction of the sharpened tip can be particularly useful for certain tissue sites. For example, once a sharpened distal end has pierced the joint capsule of an orthopedic joint, there is risk of piercing through the opposite end of the joint capsule. By retracting the sharpened end, images of the joint capsule can be captured and medication injected without fear of further damaging the joint capsule.

In certain embodiments, the edges and sides of the elongated body and tip are blunted so as not to damage the surrounding tissue while inserting the elongated body. Blunting of the sharp edges from both the axial end and the side are critical as the integrated nature of the device results in the sharp edges being exposed to the interior anatomy. Similarly, typically a blunt cannula has a removable trocar which provides access through the tissue, the trocar then replaced with a separate camera hypotube.

In some embodiments, blunting is accomplished with the deflected geometry of the distal end biasing the optical hypotube against the inner diameter of the outer tubular body. Furthermore, the distal end of the outer tubular body may comprise a reverse grind that further protects the sharp edge as the edge is directly against the OD of the optical hypotube. In some embodiments the outer tubular body may comprise dimples on either the outer tubular body or the optical hypotube that would bias the OD of the optical hypotube against the ID of the elongated body. In certain embodiments, there may be one dimple, two dimples, three dimples, four dimples, or more than four dimples. In some embodiments, the dimples may be replaced or added to with spring fingers and/or other secondary parts to bias and direct the optical hypotube. For example, spring fingers on the hypotube could touch the inner diameter of the outer tubular body. Such fingers or features may maintain the optical hypotube properly positioned as to direct the optical hypotube to blunt the sharpened tip. Such fingers or features may be shaped to minimally disrupt the fluid flow. In embodiments, the fingers or features may present a thin cross-section in a direction parallel to the fluid flow, for example as one, two, three, four, or more "c" shaped features protruding from the outer diameter of the optical hypotube that are axially long but provide a thin cross-section to the fluid.

Figure 3B:
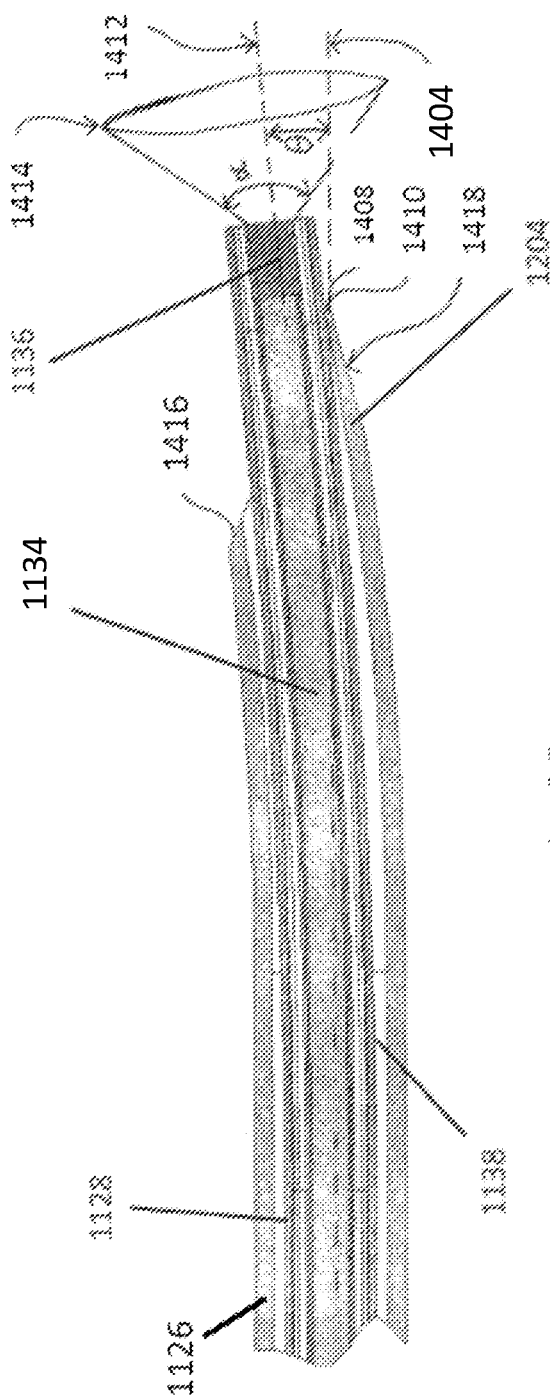

The reverse grind or reverse bevel feature may be seen with reference to FIG. 3B. The outer tubular body 1126 may be provided with a diagonal cut to produce a primary bevel surface 1416 as is common for hypodermic needle tips. However, this results in the sharpened distal tip 1410 being spaced apart from the interior wall of outer tubular body 1126 by the thickness of the wall. In that configuration, distal advance of the probe through tissue can cause tissue to become entrapped in the space between the distal tip 1410 and the outside wall of the optical hypo tube 1128.

Thus, referring to FIG. 3B, the outer tubular body 1126 may be additionally provided with a reverse bevel or tapered surface 1418, inclining radially inwardly in the distal direction, opposing the direction of the primary bevel 1416. This places the distal sharpened tip 1410 against the inside wall of the outer tubular body 1126, thereby eliminating or minimizing the risk of tissue injury due to the distal advance of sharpened tip 1410. The point of sliding contact 1408 (discussed below) is located at the distal tip 1410, when the outer tubular body 1126 is in the retracted orientation as shown in FIG. 3B, for blunting. The lateral bias of the optical hypo tube 1128 against the outer tubular body 1126, in combination with the reverse bevel 1418 produces an atraumatic distal structure.

FIG. 3A depicts an embodiment of the distal end 1108 of the elongated body 1102 similar to the embodiments described in FIGS. 2A-C. The elongated body 1102 may be in the extended position, such as illustrated in FIG. 3A, allowing the sharpened tip 1410 of the distal end 1108 to pierce the tissue of interest as described herein this section or elsewhere in the specification. As described above, while in the retracted position depicted in FIG. 3B), the elongated body is less likely to further damage the tissue site. Further, the sharpened distal tip 1410 of the elongated body 1108 may have a lateral deflection relative to the longitudinal axis of the elongated body 1102, resulting in a deflected tip 1130. In further embodiments, the tip may be straight. The deflection may be in an upward direction when the handpiece is oriented as in FIG. 2B with the controls on the top. Deflection may be at least about 1 degree, 3 degrees, 7 degrees, 12 degrees, 15 degrees or more from the axis of the elongated body.

The deflected tip 1130 allows a mechanical means of altering the direction of view of the optical hypotube (such as about 5-6 degrees). In some embodiments, the direction of view may be at least about 3 degrees, at least about 6 degrees, at least about 12 degrees, at least about 15 degrees, at least about 20 degrees, at least about 30 degrees, at least about 45 degrees, or greater than 45 degrees off the central longitudinal axis 1112 of the optical hypotube. Wide angle field of view can be accomplished with a lens, or by rotating the fiber optic if the distal end is deflected off axis. The deflected tip may also provide better directional performance during insertion and limit the "coring" associated with traditional needle geometry (minimizing the chance that a skin core will be dragged into the patient and potentially cause an infection).

With continuing reference to FIG. 3A, The elongated body 1102 may be substantially linear throughout at least about the proximal 65% and in some implementations at least about 80% of the axial length, with a deflected distal segment 1108 as has been discussed. Disregarding the deflection, the elongated body 1102 may be characterized by a central longitudinal axis 1104 from which the distal segment 1108 deviates laterally.

In the illustrated embodiment, the degree of deflection of the distal segment 1108 positions the distal sharpened tip 1410 approximately in alignment with the central longitudinal axis 1404. Thus the lateral displacement 1406 resulting from the deflection in the illustrated embodiment is approximately 50% of the outside diameter of the elongated body 1102. The lateral displacement 1406 is generally no more than about the outside diameter of the elongated body 1102, and in many implementations is at least about 10% and sometimes at least about 25% of the OD of the elongated body 1102. In certain implementations of the invention, the lateral displacement 1106 is within the range of from about 40% to about 60%, and sometimes between about 45% and 55% of the OD of elongated body 1102.

The foregoing tip configuration allows the elongated body 1102 to penetrate through tissue along a substantially linear axis, while at the same time launching the distal tip of the optical hypotube with a lateral inclination. Since the optical hypo tube 1128 is substantially linear, and the elongated body 1102 is provided with the deflected distal segment, a point of sliding contact 1408 is created between a distal edge of the optical hypo tube 1128 and an inside surface of the elongated body 1102. The lateral inclination of the outer tubular body 1126 causes the optical hypo tube 1128 to bend laterally as the outer tubular body 1126 is withdrawn proximally with respect to optical hypo tube 1128. This result may alternatively be accomplished by providing a preset lateral deflection in a distal segment of the optical hypotube, in combination with an outer tubular body having either a deflected or substantially linear distal segment 1408.

The effect of the foregoing geometry, as has been briefly discussed, is to enable a mechanical broadening of the lateral field of view. Optical broadening of the field of view may alternatively or additionally be accomplished, using a variety of optical lens systems well known in the art.

Referring to FIG. 3B, the optical hypo tube 1128 will enable viewing along a primary viewing axis 1412. Depending upon the distal optics of the optical hypo tube, the primary viewing axis 1412 will typically launch at a perpendicular angle to the distal optical surface, and reside on a center of rotation of a typically substantially conical field of view 1414. The geometric shape of the field of view 1414 may be modified, as desired, such as to oval, rectangular or other shape either through optics or software.

The lateral deflection of the primary viewing axis 1412 may be quantified, among other ways, by identifying an angle theta between the central longitudinal axis 1404 of the elongated probe body 1102 and the primary viewing axis 1412. The angle theta may be at least about 1°, at least about 3°, at least about 7°, at least about 12°, at least 15 degrees, or more, but typically no more than about 45°, and in certain embodiments, at least about 3° and no more than about 8° or 10°.

The field of view 1414 may be characterized by an angle alpha, which will depend primarily upon the distal optics 1136. The angle Alpha will typically be between about 45° and about 120°, such as between about 55° and 85°. In one implementation, the angle Alpha is approximately 70°.

As will be appreciated by reference to FIG. 3B, the field of view Alpha enables lateral deflection of the primary viewing axis 1412 throughout a range to enable lateral viewing, while still permitting the central longitudinal axis 1104 to intersect target tissue at a point that remains within the field of view 1414. This enables visualization straight ahead of the tubular body, along the central longitudinal axis, while at the same time permitting increased lateral viewing in the angle of deflection. Rotation of the elongated body 1102 about the central longitudinal axis 1404 therefore enables sweeping the optical field of view through a range of rotation which effectively increases the total visualized target size. For example, in an embodiment having a field of view of 70°, and a deflection of 5°, rotation about the central longitudinal axis 1404 throughout a full revolution enables sweeping through an effective field of view of 152°.

In some embodiments, the elongated body 1102 comprises a lumen 1138 that may deliver fluid including medications such as anti-inflammatory agents, antibiotics, anesthetics or others known in the art within the capsule or to other tissue site. In certain embodiments, as depicted in FIG. 3A, the lumen 1138 may encompass the annular space between the optical hypotube 1128, and the outer tubular body 1126.

In some embodiments, the distal end of the visualization element may comprise a distal lens 1136 configured to facilitate the imaging of an internal tissue site. The distal lens, or any other lens, may develop defects and imperfections during manufacturing, leading to a distortion in the image. These distortions may be unique to individual lenses and thus in the case of the embodiments disclosed herein this application, may be unique to an individual tissue visualization device. Thus, to enhance image quality, the device 1100 as depicted in FIG. 2A, may include an automatic optical correction in the form of a unique algorithm. In some embodiments, the algorithm may be stored in a chip or other suitable means within the handpiece 1004.

In certain embodiments, the automatic optical correction may serve to improve the image quality generated by the tissue visualization device. The Abbe number, also known as the V-number or constringence of a transparent material, is a measure of the material's dispersion (variation of refractive index with wavelength) in relation to the refractive index, with high values of V indicating low dispersion (low chromatic aberration). Low chromatic aberration is desired to optimize image quality, but achieving low chromatic aberration normally increases manufacturing cost. In some embodiments, chromatic aberrations in the tissue visualization device may be corrected via the aforementioned software algorithm at the time of clinical use, which allows economies during manufacturing. For example, the optical correction may allow for visualization performance from the device with less expensive lenses that rivals the performance of visualization devices that use far more expensive lenses with minimal imperfections.

In embodiments, to generate the algorithm at the point of manufacture, the distal optic is focused on a known definition pattern. A computer can then compare the captured image to the known pattern and create an algorithm that restores the captured image to the true definition pattern. As described above, that algorithm may then be stored in a chip in the handpiece 1104.

When the handpiece 1104 is connected to a displayer 6 at the clinical site, as described previously in relation to FIG. 1, the algorithm serves as the basis for the displayer 6 to correct the captured image such that aberrations in the optical system are removed. Each individual tissue visualization device will have unique aberrations, so each handpiece will carry a unique algorithm designed to correct that system.

Returning to FIG. 3B, FIG. 3B further depicts a closer view of an embodiment of the sharpened distal end 1204 of the elongated body in the retracted position. As described above, in relation to FIG. 2C, the retraction control serves to retract the sharpened deflected tip 1204 to prevent further damage to the surrounding tissue while viewing an interior tissue site.

As shown in FIG. 3C, in certain embodiments of the distal end of the elongated body 1700, the distal end of the optical hypotube 1702 may be flared 1706 to accommodate a larger sensor 1708 positioned at the distal end of the optical hypotube 1702 than would ideally fit into the diameter of a standard hypotube 1704. This flare could simply be a larger diameter cross-section, a square cross section or something to match what is within. The axial length of this flare would be to accommodate the length of the sensor plus routing of illumination fiber around the sensor and would have a transition zone back to the circular cross section of the normal hypotube. In certain embodiments, this may be accomplished with a non-circular cross-section. The sharpened tip may also need to would also be flared with or without a gap to provide a lumen between the optical hypotube's "OD" and the elongate member's "ID". In certain embodiments, the outer tubular body may be curved such as disclosed herein this section or elsewhere in the specification or the outer tubular body may be straight to accommodate the flared tip.

As described above in relation to the "flared" embodiment, in order to minimize the overall size of the product/needle, the inner diameter (ID) of the outer tubular body may be sized so that it is completely "filled" by the outer diameter(OD) of the flared distal end of the optical hypotube. In embodiments, the flared geometry restricts the inner lumen and prevents the passage of fluid from the end of the outer tubular body.

In embodiments, to allow for fluid flow, the axial length of the flare geometry may be designed to be shorter than the translation distance of the outer tubular body 1710. When the outer tubular body is in the forward or sharp position, the flare is contained within the inner diameter of the tubular body and flow is restricted through the lumen 1712. However, when the tubular body is the retracted position (and blunted), the flared portion of the hypotube completely protrudes out of the open bevel of the tubular body, thereby allowing the effective lumen of the device to be between the normal cross-section of the hypotube and the ID of the needle. In some embodiments, the outer tubular body may contain axial holes to allow for fluid flow from the lumen in a different direction and location from the open end of the elongate body.

Figure 4:
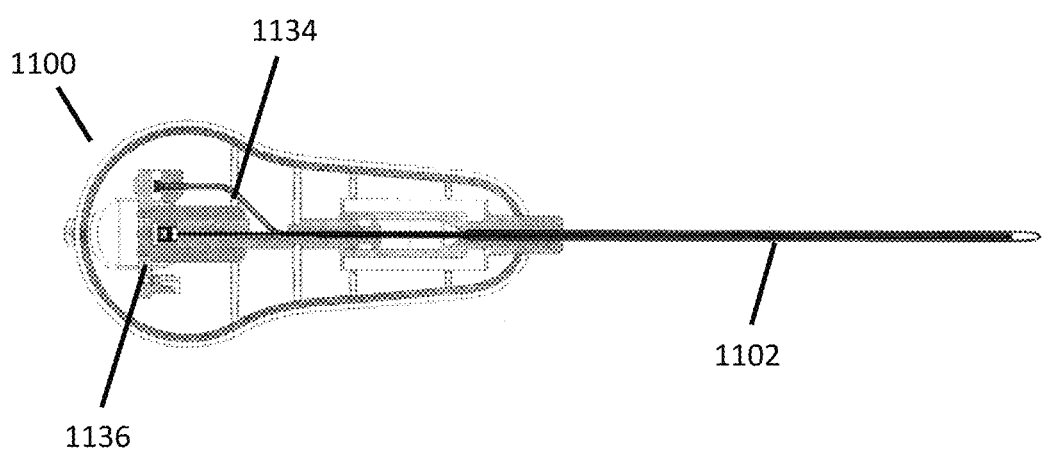
FIG. 4 illustrates a cross-sectional top view of an embodiment of a tissue visualization and modification device

FIG. 4 depicts a cross-sectional top view of an embodiment of the tissue visualization device 1100. The handpiece 1104 comprises an illumination element 1134 and a visualization sensor support 1180, described in greater detail below. Similar to illumination elements or apparatuses described elsewhere in this specification, the illumination element 1134 may extend down the length of the elongated body and convey light down the elongated body to an interior tissue site to allow for visualization of the target tissue. In some embodiments, the illumination element 1134 comprises a bundle or bundles of illumination fibers.

Figure 5:
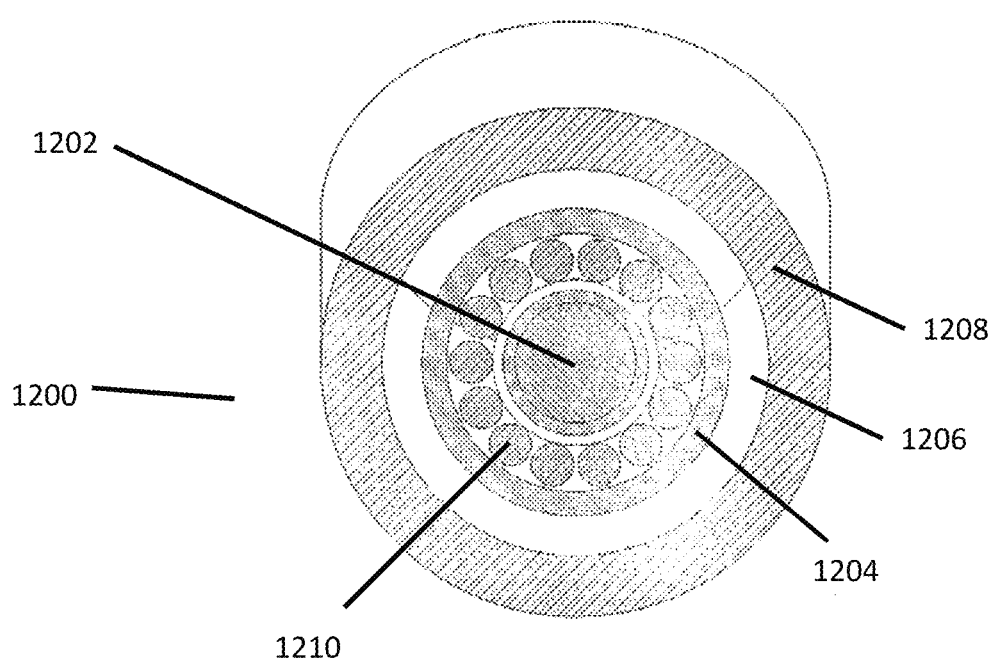
FIG. 5 illustrates a cross-sectional view of an embodiment of a tubular portion of a tissue visualization and modification device.

FIG. 5 illustrates cross sectional views of an embodiment of a tissue visualization device down the length of an elongated body 1200, similar to the elongated bodies depicted in FIGS. 2A-4. In certain embodiments, the optical hypotube 1204 may comprise an image guide 1202, at least one illumination fiber or fiber bundle 1210, an infusion lumen 1206, and outer tubular body 1208. As will be understood by one skilled in the art, the use of the term "illumination fiber" here encompasses an illumination fiber or fiber bundle. As described elsewhere in the specification, the illumination fibers or fiber bundles may be configured to transmit a wavelength of light suitable for illuminating a target tissue for visualization; however, the illumination fibers may also be configured to transmit UV light to a tissue site for the purpose of solidifying a UV-sensitive material. For example, if there are 14 total illumination fibers or fiber bundles, then 7 may be configured to deliver light suitable for visualization while another 7 may be suitable for delivering UV light. However, any suitable combination may be used. For example, most of the illumination fibers may be UV, half of the illumination fibers, or less than half. In particular embodiments, the number of illumination fibers may be increased or decreased from the number depicted in FIG. 5. For example, there may be one fiber, at least two fibers, at least 5 fibers, at least 10 fibers, at least 14 fibers, at least 20 fibers, at least 25 fibers, at least 50 fibers, or more than 50 fibers. In certain embodiments, the illumination fibers may be configured to output multiple wavelengths of light suitable for imaging an internal tissue site.

The wavelength of light delivered via illumination fibers 1210 [which can be at least 4, 8, 12 or more fibers or bundles of fibers, and which may be arranged in an annular configuration surrounding the image guide 1202 as shown in FIG. 5 but described in detail below] may be selected for various wavelength specific applications. For example, wavelengths in the UV range can be utilized to permit visual differentiation of tissue types such as to distinguish nervous tissue from surrounding tissue and/or minimally vascularized nervous tissue. Blood vessels may appear to have a first color (such as red) while nerve tissue may appear to have a second color (such as blue). The wavelength may also be optimized to distinguish nervous tissue from muscle.

In another application, light such as UV light or visible light may be propagated via fiber 1210 to promote or initiate curing of an infused solution (e.g., via polymerization or cross-linking), where the solution or gel is administered via infusion lumen 1206, to form a solid or semi-solid mass in vivo. The mass may be a tissue bulking device, coating layer or other structural element.

Another wavelength specific application involves directing a preselected wavelength to a target impregnated with a drug or drug precursor. Upon delivery of the preselected wavelength to the target, drug is released, or the precursor is converted into a drug which is then released. The target may be an implanted mass or device, or an infused carrier medium such as any or a combination of a liquid, gel, or beads.

The UV light may include Ultraviolet A, long wave, or black light, abbreviated "UVA" and having a wavelength of 400 nm-315 nm; Near UV light, abbreviated "NUV" and having a wavelength of 400 nm-300 nm; Ultraviolet B or medium wave, abbreviated "UVB" and having a wavelength of 315 nm-280 nm; Middle UV light, abbreviated "MUV" and having a wavelength of 300 nm-200 nm; Ultraviolet C, short wave, or germicidal, abbreviated "UVC" and having a wavelength of 280 nm-100 nm; Far UV light, abbreviated "FUV" and having a wavelength of 200 nm-122 nm; Vacuum UV light, abbreviated "VUV" and having a wavelength of 200 nm-400 nm; Low UV light, abbreviated "LUV" and having a wavelength of 100 nm-88 nm; Super UV light, abbreviated "SUV" and having a wavelength of 150 nm-10 nm; and Extreme UV light, abbreviated "EUV" and having a wavelength of 121 nm-10 nm. In some embodiments, the catheters may include an element that emits visible light. Visible light may include violet light having a wavelength of 380-450 nm; blue light having a wavelength of 450-475 nm; cyan light having a wavelength of 476-495 nm; green light having a wavelength of 495-570 nm; yellow light having a wavelength of 570-590 nm; orange light having a wavelength of 590-620 nm; and red light having a wavelength of 620-750 nm. In some embodiments, the catheter includes an element that emits light having a wavelength between about 300 nm and 500 nm. In particular, the catheter may include an element that emits light having a wavelength associated with blue light (e.g., light having a wavelength between about 450-475 nm).

Wavelength selection information and characterization and other details related to infrared endoscopy are found in U.S. Pat. No. 6,178,346; US Patent Application Publication No. 2005/0014995, and US Patent Application Publication No. 2005/0020914, each of which is hereby incorporated by reference in its entirety.

In certain embodiments, the outer diameter of the optical hypotube may range from approximately 0.1 mm to 3 mm, approximately 0.5 mm to 2.5 mm, or approximately 1 mm to 2 mm. In certain embodiments, the outer diameter of the optical hypotube is approximately 1.27 mm. In some embodiments, the inner diameter of the outer tubular body ranges from approximately 0.1 mm to 10 mm, approximately 0.2 mm to 8 mm, approximately 0.5 mm to 6 mm, approximately 1 mm to 5 mm, approximately 1.2 mm to 4 mm, or approximately 1.4 mm to 3 mm. In certain embodiments, the inner diameter of the outer tubular body 1208 is approximately 1.6 mm.

In some embodiments, the image guide 1202 allows for the viewing of an image of the tissue site by the visualization sensor in the handpiece. In particular embodiments, the image guide may be a fiber optic or other suitable medium to allow for imaging of the tissue site by a visualization sensor as described herein this section or elsewhere in the specification. The fiber optic bundle may have at least about 6K, or at least about 10K or at least about 15K or at least about 30K fibers or more, depending upon the desired performance. In some embodiments, the image fiber may be a 6.6 k fiber bundle or a 10 k fiber bundle.

Figure 6A:
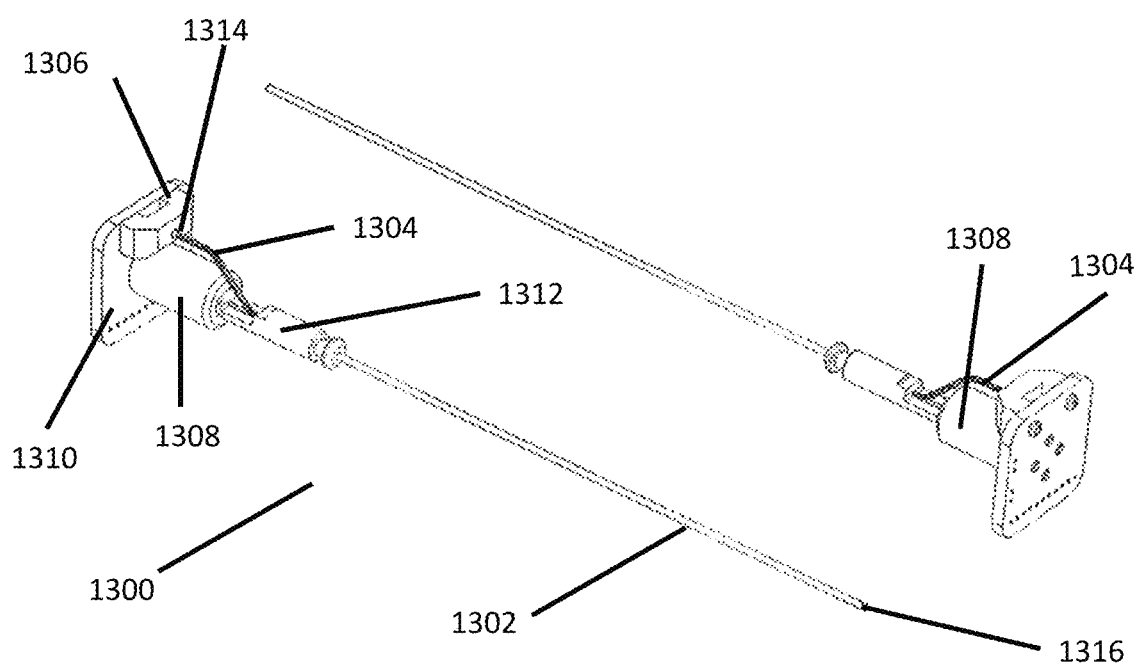
FIGS. 6A-C illustrate embodiments of a tissue visualization device with the outer housing removed.
Figure 6B:
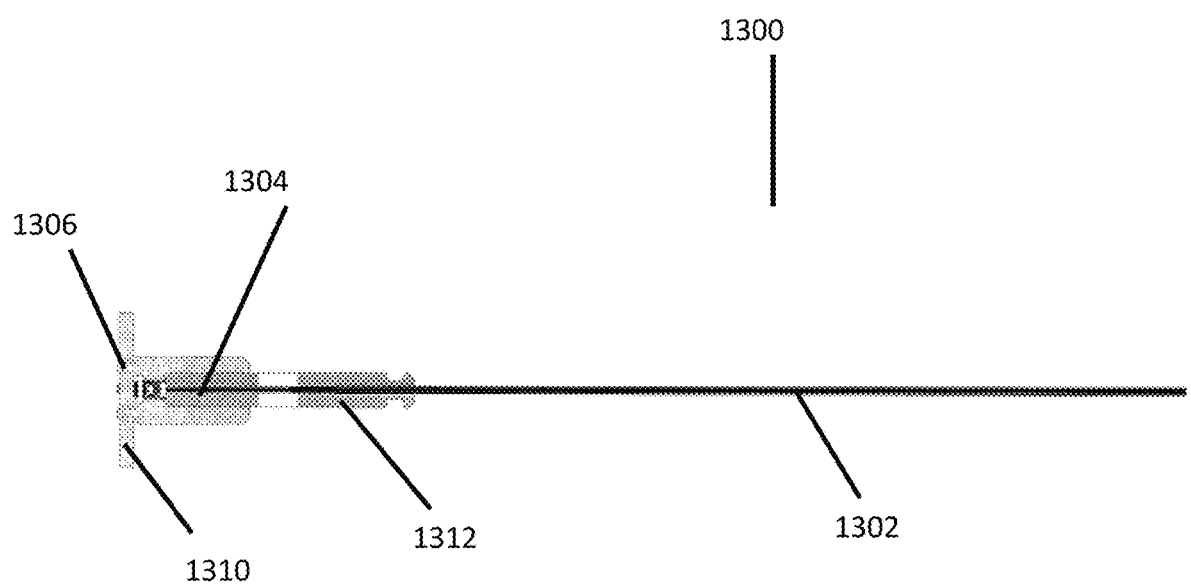
Figure 6C:
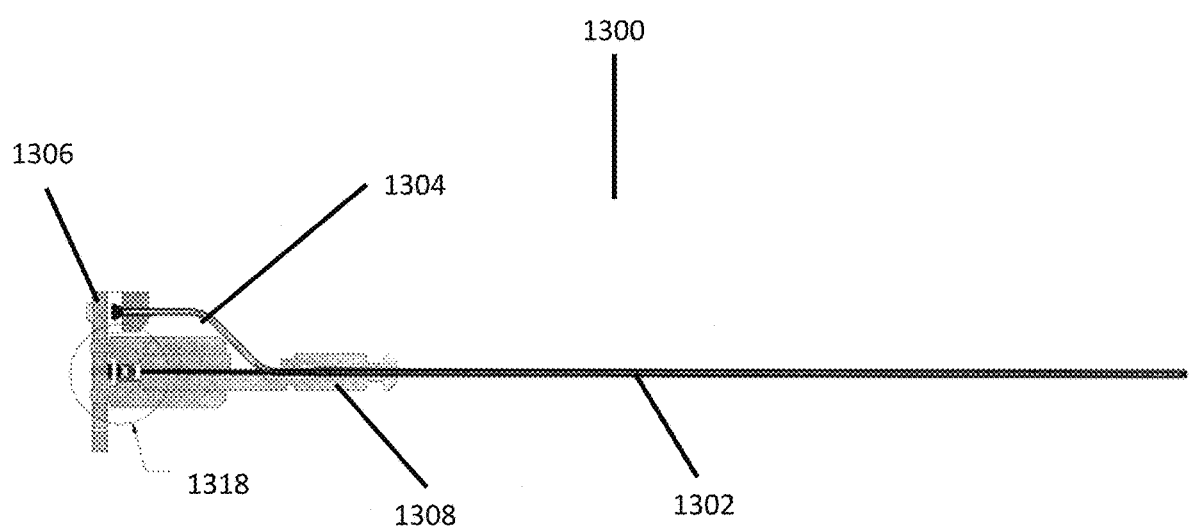

FIGS. 6A-C illustrate embodiments of the elongated body and inner components of a tissue visualization device 1300, similar to the embodiments depicted elsewhere herein. In this particular figure, the outer shell of the handpiece is removed to better view the interior of the device. In certain embodiments, the tissue visualization device comprises an elongated body 1302, an illumination element 1304, light source housing 1306, a proximal lens housing 1310m a ferrule 1314, a nosepiece 1312, and a distal lens 1316.

FIG. 6B illustrates a top view of the tissue visualization device 1300 of FIG. 6A, while FIG. 6C illustrates a side view. The components in these figure are similar to the components illustrated in 6A, however in 6B, the visualization complex is identified as 1318. The visualization complex and surrounding components can be viewed in more detail in FIG. 7.

Figure 7:
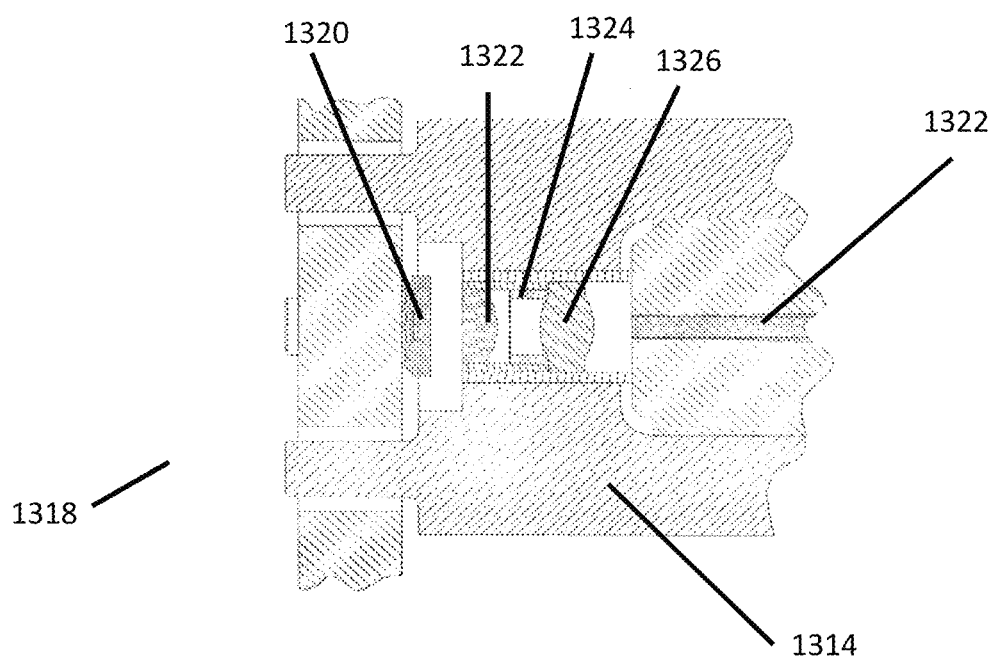
FIG. 7 illustrates a cross-sectional side view of an embodiment of the lens housing depicted in FIG. 6A-C.

FIG. 7 illustrates a cross-sectional side view of an embodiment of the visualization complex of FIG. 6C. In some embodiments, the visualization complex 1318 may comprise a visualization sensor 1320 such as those visualization sensors described herein this section or elsewhere in the specification. In certain embodiments, the visualization sensor may be a CMOS sensor as described herein this section or elsewhere in the specification.

In certain embodiments, the visualization complex can comprise a first lens 1322, an optical aperture 1324, and a second lens 1326. In some embodiments, the aperture may have a diameter of at least about 0.1 mm, at least about 0.2 mm, at least about 0.3 mm, at least about 0.5 mm, or more than 0.5 mm. Preferably, the aperture may be approximately 0.222 mm. To support the lenses, the visualization complex may comprise a proximal lens housing as described previously, wherein the proximal lens housing may serve to secure the lenses 1320 and 1326 in the proper location and orientation. The visualization complex may further comprise an image guide, similar to the image guide described previously in relation to FIG. 5.

Figure 8A:
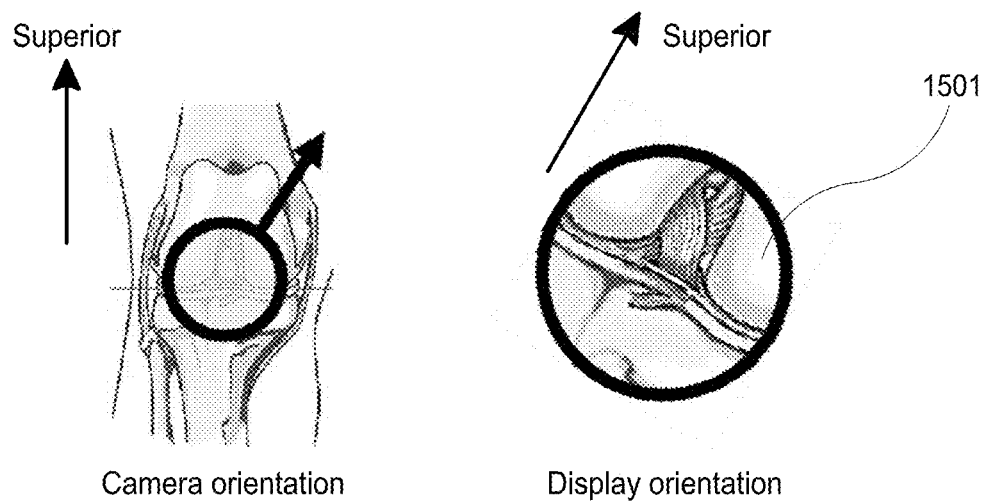
FIGS. 8A-B illustrates embodiments of images with or without rotational image stabilization.
Figure 8B:
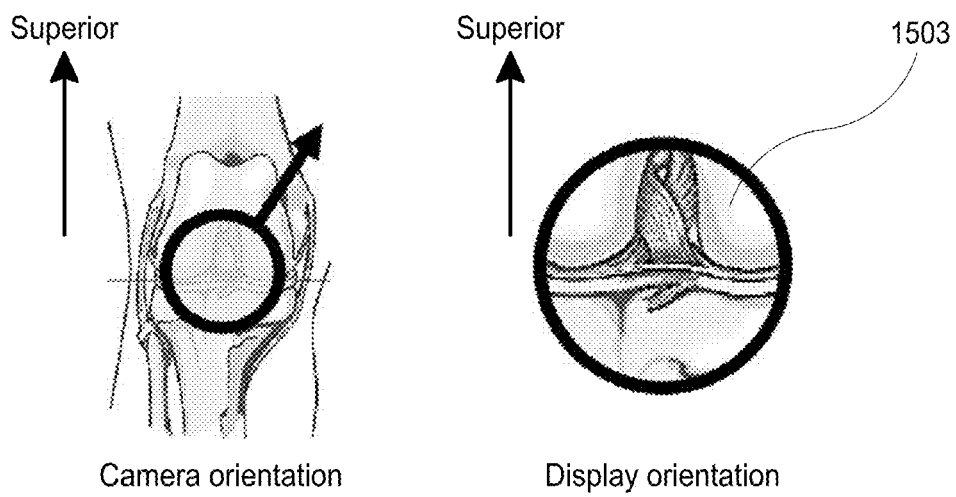

As illustrated in FIG. 1 and FIG. 8A, one consequence of the integrated visualization device of the present invention is that rotation of the visualization device 4 about the central longitudinal axis 1404 to achieve the enlarged field of view will simultaneously cause a rotation of the apparent inferior superior orientation as seen by the clinician on the display such as video screen 19 of FIG. 1 or image 1501 of FIG. 8A. It may therefore be desirable to compensate such that a patient reference direction such as superior will always appear on the top of the screen 19, regardless of the rotational orientation of the visualization device 4, such as depicted in image 1503 of FIG. 8B.

This may be accomplished by including one or more sensors or switches carried by the visualization device 4, that are capable of generating a signal indicative of the rotational orientation of the visualization sensor 1132. The signal can be transmitted via wire or wireless protocol to the controller 6 for processing and correction of the rotational orientation of the image on screen 19 or other display, to stabilize the image.

Suitable sensors may include simple tilt or orientation sensors such as mercury switches, or other systems capable of determining rotational orientation relative to an absolute reference direction such as up and down. Alternatively, the rotational orientation image correction system may comprise a 3-axis accelerometer with associated circuitry such as a small accelerometer constructed with MEMS (micro-electro mechanical systems) technology using capacitance measurement to determine the amount of acceleration, available from Freescale Semiconductor, Inc., of Austin, Tex. and other companies.

As an alternative or in addition to the accelerometer, the visualization device may carry a gyroscope such as a three-axis gyroscope. The output of the gyroscope may be the rate of change of roll angle, pitch angle and yaw angle and rotational rate measurements provided by the gyroscope can be combined with measurements made by the accelerometer to provide a full six degree-of-freedom description of the sensor 1132's motion and position, although that may not be necessary to simply correct for rotational orientation. A control may be provided on the hand piece or controller 6, allowing the clinician to select what reference orientation (e.g., patient superior, inferior, true up or down, etc. or true sensor view such that the image on the screen rotates with the sensor) they would like to have appearing at the top of the screen regardless of sensor orientation. In certain embodiments, markers such as an arrow or line may be projected onto the image to further identify different orientations and/or directions In some embodiments, the optical hypotube may be sheathed in heat shrink tubing. For example, the outer tubular body as described elsewhere in the specification, may be constructed from a heat-sensitive material. Thus, to construct the elongated body as described elsewhere in the specification, the optical hypotube and other components may be extended down an over-sized outer tubular body which is then shrunk down to the diameter of the optical hypotube via means such as heat, UV, chemical, or other means. In contrast, traditional endoscopes and some endoscopes described elsewhere in the specification house the optics in a rigid stainless steel tube. However, housing the optics within a stainless steel tube may require forcing many optical and illumination fibers down a very tight ID and then applying an adhesive such as epoxy. Such a process is difficult and costly.

Figure 9A:
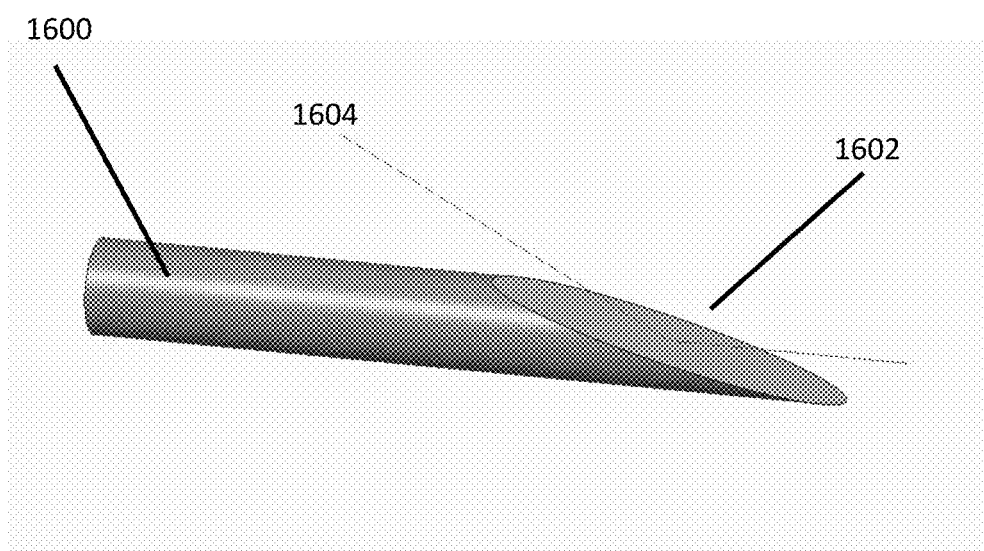
FIGS. 9A-D illustrate embodiments of a tissue visualization device comprising a mirrored surface.
Figure 9B:
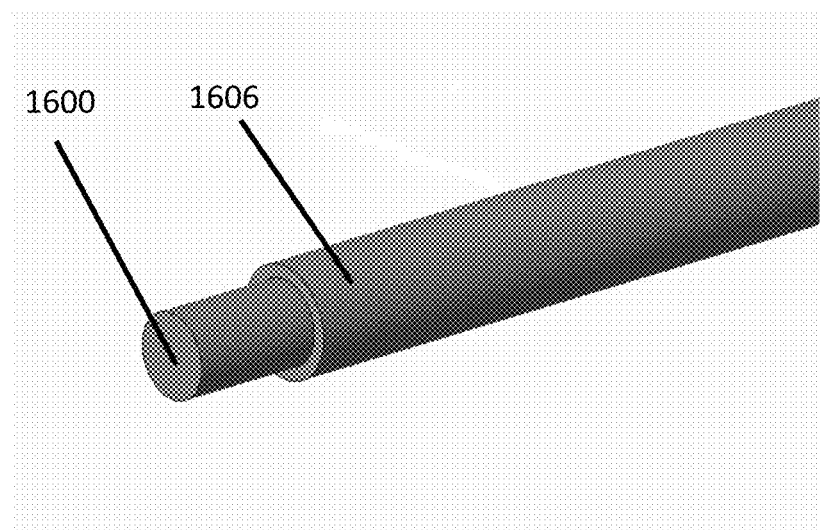

FIGS. 9A-D illustrate an embodiment of a visualization device, similar to the visualization devices in FIGS. 1-7. The visualization device of FIGS. 9A-D incorporate at least one mirror to alter the viewing direction and field of view of the visualization device. FIG. 9A depicts a reflective plug 1600 which may be inserted into the distal end of a tubular body, such as the tubular bodies described above in relation to FIGS. 1-3B. Such a plug may comprise a mirrored surface 1602 that will reflect an image at a particular angle 1604, for example, providing a direction of view 30 degrees from the axis of the plug. In some embodiments, the angle may be much smaller, such as between 0-15 degrees. In further embodiments the angle may range from 15-45 degrees. In some embodiments, the angle may be at least 45 degrees, at least 60 degrees, at least 75 degrees or at least 90 degrees or more. As illustrated in FIG. 9B, and described above in relation to FIG. 9A, the plug 1600 may be inserted into the end of a tubular body 1606, similar to the tubular bodies described elsewhere in the specification. In embodiments, the plug may be incorporated into any of the visualization devices described elsewhere in the specification. In some embodiments, the plug may be sharpened to allow the plug to pierce tissues.

Figure 9C:
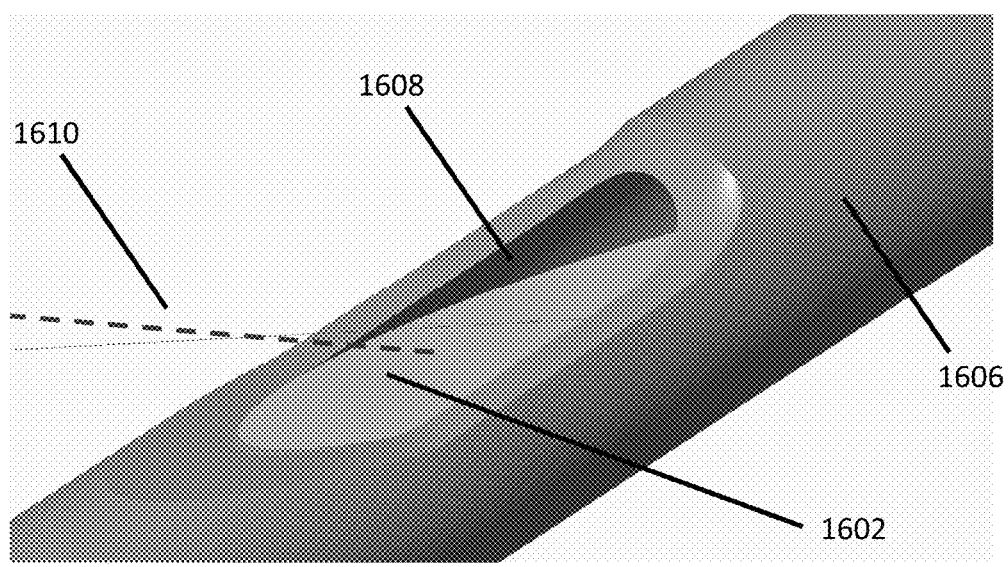
Figure 9D:
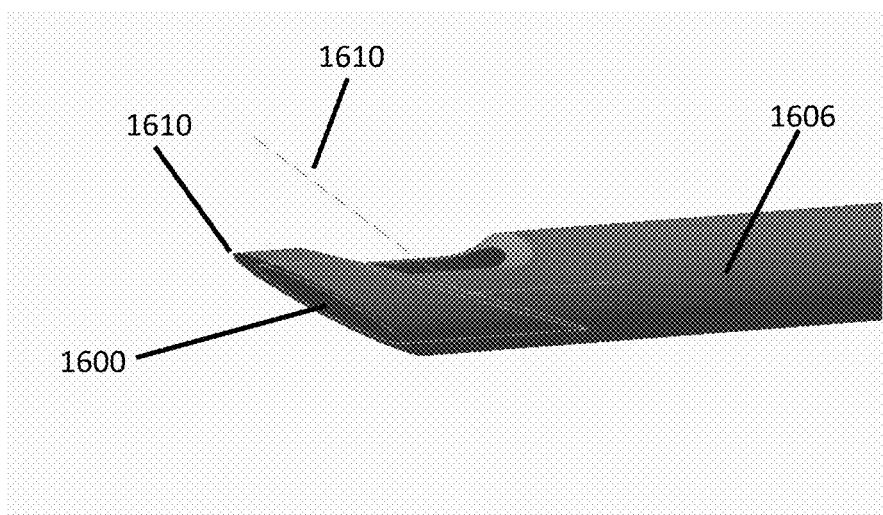

FIGS. 9C-D illustrate embodiments of the outer tubular body of FIG. 9B comprising a gap 1608. The gap allows for light to reflect from the mirrored surface 1602 and be directed down the tubular body 1606, thereby transmitting an image of the field of view available through the gap down the elongated body. Such an image may be transmitted along an optical hypotube and/or image guide such as described elsewhere in the specification. Further components, such as illumination elements may be used to direct light along the mirrored surface and out through the gap to illuminate surrounding tissues. In embodiments, the gap may allow for a field of view 1610 that extends forward and above the distal end of the tubular body. Depending on the angle and orientation of the mirrored surface, the magnitude of the field of view may be between about 45° and 120°, such as between about 55° and 85°. In one implementation, the angle may be approximately 70°.

In embodiments, the visualization devices of FIGS. 9A-D may be manufactured from a variety of means. For example, a tubular reflective material such as depicted by reflective plug 1600 may be sliced at a desired angle and milled/polished to create a mirrored surface 1602. Such a plug with a mirrored surface may be fed through an open end of a tubular body with a cut gap 1608, such as tubular body 1606 of FIGS. 9B-D, and welded to the tubular body. Once the mirrored surface is properly positioned within the tubular body, the tubular body and reflective plug may be cut/milled at the same time to create a sharpened tip 1612, such as illustrated in FIG. 9D.

In certain embodiments, a desired direction of view may be reached by positioning a prism at the distal end of the elongated body. Such a prism may provide a direction of view such as disclosed elsewhere in the specification, for example: providing a direction of view 30 degrees from the axis of the elongated body. In some embodiments, the angle may be much smaller, such as between 0-15 degrees. In further embodiments the angle may range from 15-45 degrees. In some embodiments, the angle may be at least 45 degrees, at least 60 degrees, at least 75 degrees or at least 90 degrees or more.

In some embodiments, the elongated body may be in a shape that is non-circular. For example, the entirety of the elongated body may be oval or elliptical in shape. In some embodiments, only the distal end of the elongated body is oval-shaped while the remainder of the elongated body is circular. An oval shaped elongated body advantageously allows for additional space for the deflected distal tip. In certain embodiments, the major axis of the ellipse is approximately 1.1 times as long as the minor axis. In some embodiments, the major axis is at least 1.2 times, 1.3 times, 1.5 times, 1.75 times, 2 times, 3 times, 4 times, 5 times, or more than 5 times as long as the minor axis.

In particular embodiments, the distal tip of the elongated body may be constructed from elastic material to allow the distal tip to flex distally. Further, the deflected portion of the distal tip may be very short, allowing the deflected portion to stay within the outer perimeter confines of the elongated body.

In certain embodiments, the distal end of the elongated body may be rotated with respect to the optical hypotube. For example, the sharped distal point may be under the optical hypotube, over the top of the optical hypotube, or on with side of the optical hypotube. In certain embodiments, the optical hypotube may act as a shield to prevent the sharpened distal point from damaging the surrounding tissue in any orientation. In certain embodiments, the optical hypotube may comprise a shield at the distal tip, the shield acting to protect the surrounding tissue from the sharpened distal tip of the elongated body. Upon rotation of the optical hypotube, the shield may be moved from the sharpened distal tip of the elongated body, allowing for further penetration through tissue.

Figure 10A:
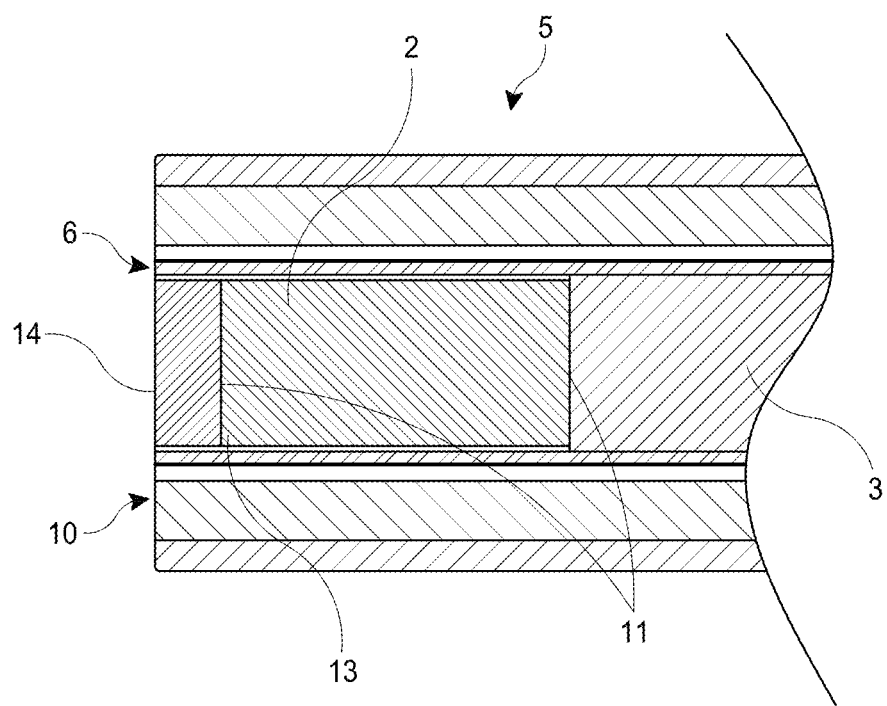
FIGS. 10A-C illustrate embodiments of a tissue visualization device.

FIG. 10A illustrates an embodiment of the distal end of a tissue visualization device, similar to the tissue visualization devices depicted in FIGS. 1-9. Here, the arrow "C" indicates the distal direction towards the tissue site. The distal end of the elongated member 5 comprises an optical fiber 3, similar to the optical hypotubes and optical elements described elsewhere in the specification. Distal lens 2 may comprise any type of lens described herein this section or elsewhere in the specification, including a GRIN (Gradient-index) lens. The lens may have a diameter of between about 100-700 microns, about 200-600 microns, about 400-500 microns, or about 465 microns.

In certain embodiments, as depicted in FIG. 10A, the distal end of the tissue visualization device may include a circular transparent plate 12, such as a glass plate or other suitable transparent material. In the embodiment depicted in FIG. 10A, the plate is non-powered, however in some embodiments the plate may be powered to have magnification levels of about 2×, 4×, 10×, 20×, 100×, or greater than 100×. The plate may be flat on both sides of the plate, rounded on both sides of the plate, or rounded on one side and flat on the other side. In certain embodiments, the plate may have a diameter of between about 100-700 microns, about 200-600 microns, about 400-500 microns, or about 465 microns. In certain embodiments, an adhesive 11 adheres the plate to the distal lens 2, and the distal lens 2 adhered to the optical fiber 3 by another adhesive.

In embodiments, and as depicted in FIG. 10A, the plate 12 may include a mask 13 on the proximal side of the plate, surrounding a transparent window 14. However, in certain embodiments, the mask may be on the distal side of the plate. By placing the mask on the proximal side of the plate, potentially toxic mask materials are prevented from interacting with tissue. The mask may comprise any suitable material that limits transmission of light such as a chrome coating. However, any suitable evaporative coating may be used such as different metallic materials.

The window encompasses an area of the plate not covered by the mask, thereby allowing light to pass through the window. As described in more detail in relation to FIG. 12 below, the mask may be applied in an annular region of the plate, thereby creating a rounded window 14.

In particular embodiments, the mask acts to limit the transmission of light through the plate, for example the mask may restrict the gathering of all the angles of light reflecting from the object being viewed (e.g. tissue site). The overlap of light rays on the image is therefore very small and the result is a sharper image over a wider depth of field. Although this may reduce the brightness of the image, the image is much sharper. In certain embodiments, the material of the mask allows at most about 0% transmission of light through the material, about 2%, about 4%, about 5% or about 10%. Further, the mask preferably absorbs light rather than reflects light to limit stray light from affecting the sharpness of the image. In embodiments, the material of the mask may reflect at most about 0% of the light impacting the surface, about 5%, about 10%, about 20%, about 25%, or about 30%. In certain embodiments, the reflectivity at 400 nm of light may be 12%, at 500 nm-20%, at 600 nm-27%, at 700 nm 33%.

The circular plate may be sized to have the same diameter as the lens 2, however, in embodiments the plate may be smaller than the lens 2, such as at least about: 10% of the size of the lens, 25%, 50%, 75%, or 90%. When the plate is smaller than the lens, light may potentially leak through the plate into the lens, thus in these scenarios an opaque adhesive or cover may be applied to the distal end of the lens to limit the passage of light into the lens. In certain embodiments, the plate may be non-circular such as rectangular or polygonal. As with the circular plate, the non-circular plate may be about: 10% of the size of the lens, 25%, 50%, 75%, or 90%. As with the smaller rounded plate, the non-covered regions of the lens may be coated in an opaque adhesive to limit the transmission of light.

In certain embodiments, rather than using a transparent plate with a mask, the plate may be replaced with any suitable material comprising an aperture. For example a metal plate with a window may be used, or an opaque polymeric material.

Commonly in the field of imaging, when using a GRIN lenses such as those described herein this section or elsewhere in the specification, an optical mask such as described above in relation to the plate, would normally be placed between two GRIN lenses or at the focus point of the lens, however, here the mask is positioned between a non-powered plate and a powered lens. Further, although the mask may be placed in the focal point of the lens, here the mask need not be located at the focal point.

Figure 10B:
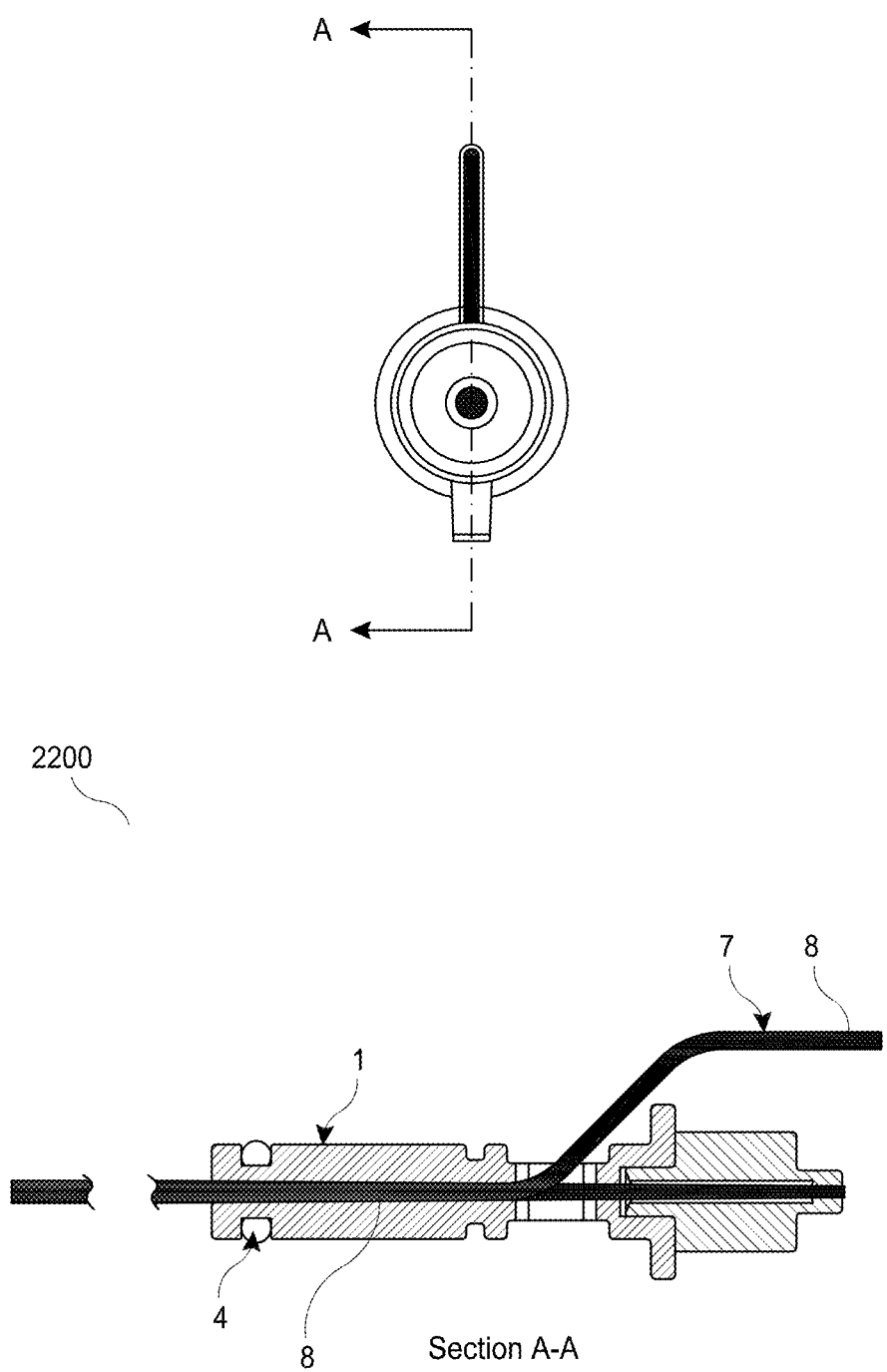

FIG. 10B illustrates a side and front view of embodiments of the visualization device, similar to the embodiments depicted in FIG. 6A.

In further embodiments, a cmos/ccd sensor may be located at the distal tip of the visualization device rather than a proximal location. With a distally mounted sensor, distally located LEDs may be utilized with or without a short light pipe rather than relying on illumination fibers to transmit the light from a proximal led.

Figure 10C:
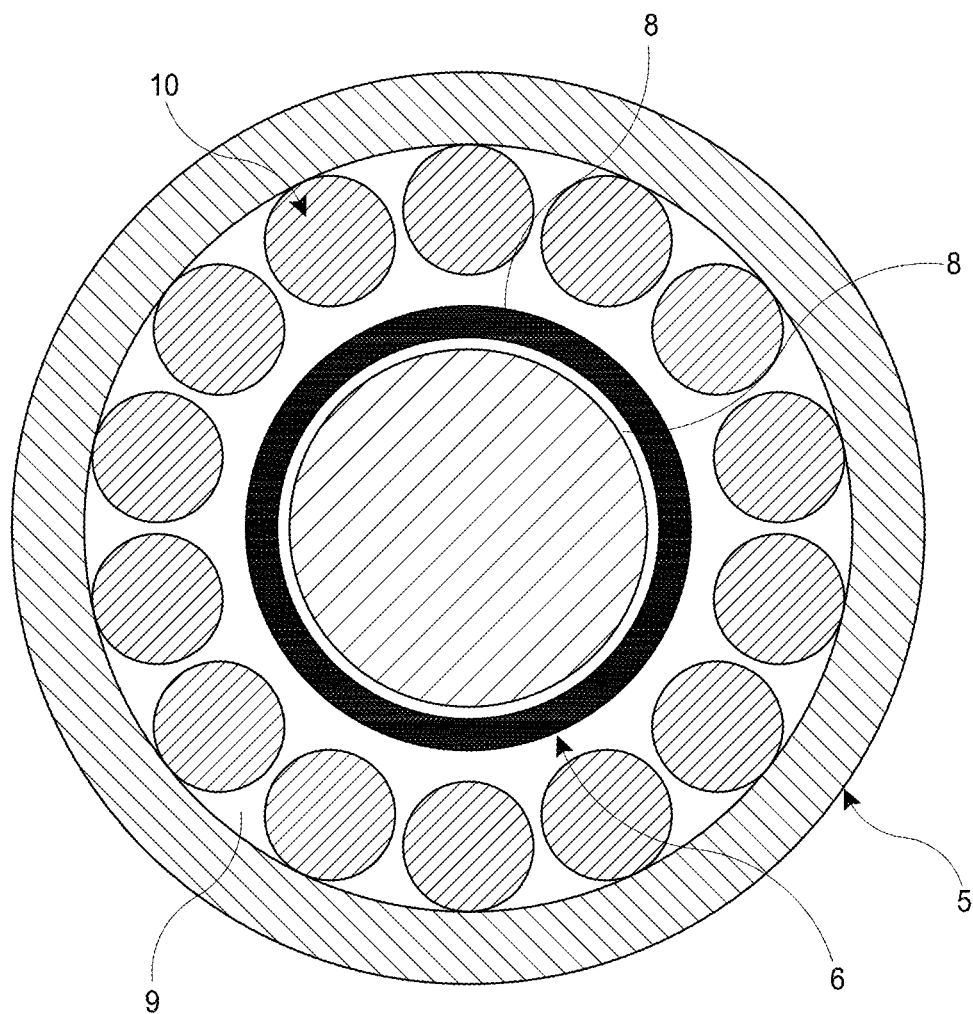

FIG. 10C illustrates a view along the elongate member of the visualization device, such as is depicted in FIG. 5. Illumination fibers 10 are secured within epoxy around a central optical element and/or image guide.

In certain embodiments, the illumination fibers can also be bunched to one side of the tube with the imaging lens and fiber on the opposite side (the drawing has them around the circumference but may also be asymmetric. The claims also talk about the ratio of the window to the fiber but the ratio is more appropriate to the diameter of the Lens.

Figure 11:
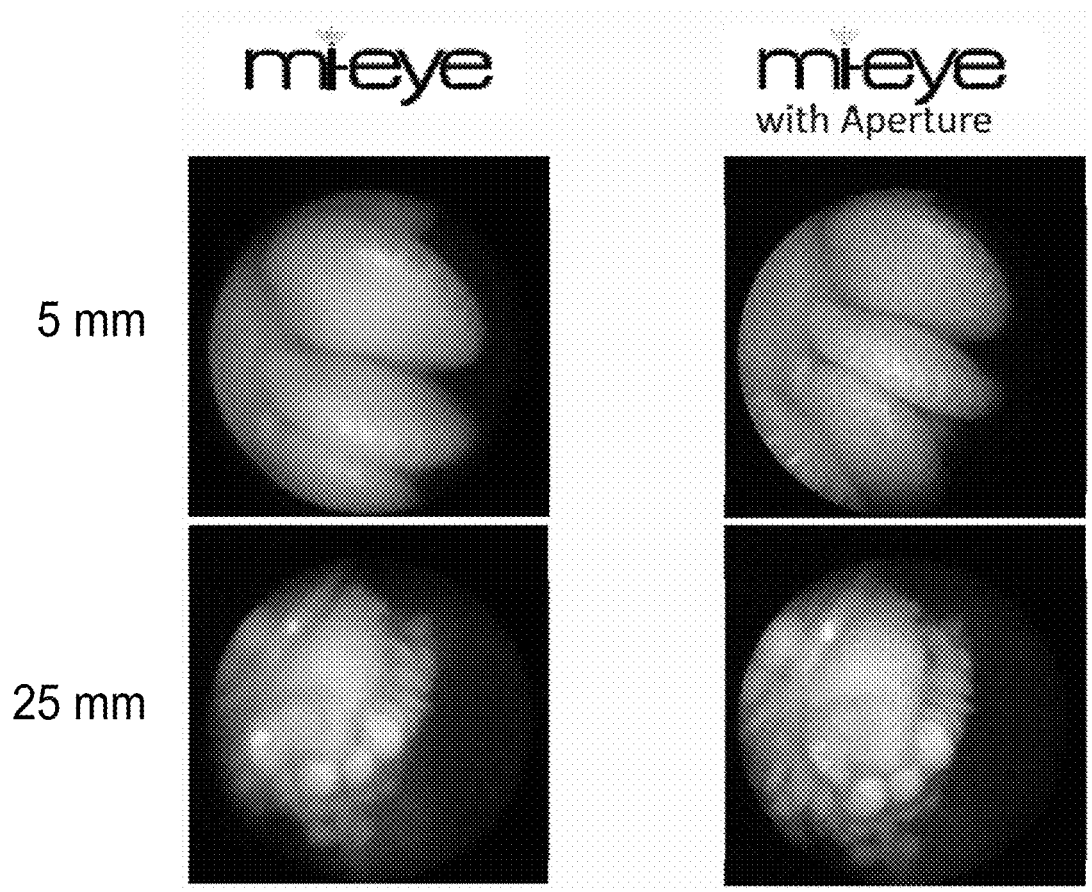
FIG. 11 is a comparison of pictures taken with and without embodiments of a non-powered plate and mask.

FIG. 11 compares pictures of the interior of a red pepper imaged with a visualization device comprising the plate described above and a visualization device without the plate. As can be viewed in the image, the addition of the plate dramatically improves the sharpness of the image.

Figure 12:
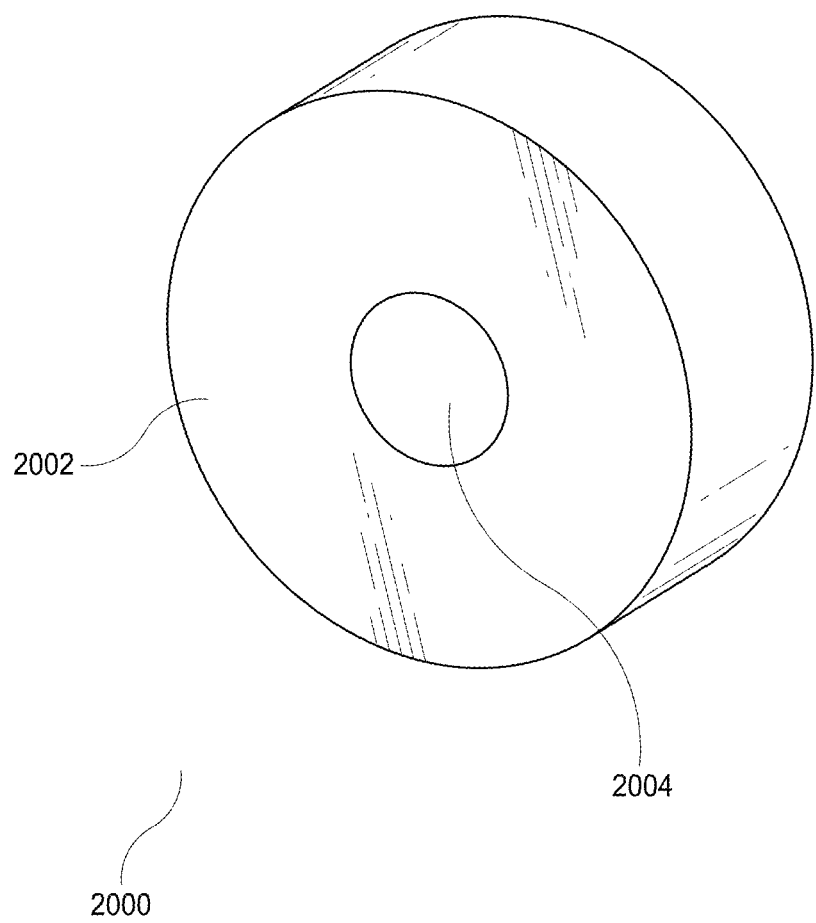
FIG. 12 is a close up view of an embodiment of a non-powered plate with an optical mask.

FIG. 12 depicts a plate 2000 such as the plate described above in relation to FIG. 10. Here the mask 2002 is annular and surrounds a transparent window 2004 that allows the passage of light. Although here the mask and window are depicted as annular, in other embodiments the mask and window may be rectangular, triangular, octagonal, or in the form of other suitable polygons. In certain embodiments the mask may cover at most: about 25% of the surface of a single side of the plate, about 50%, about 60%, about 70%, about 80%, about 90%, or about 95% of the surface area of one side of the plate. In some embodiments, as described above, the plate may have a diameter of about 0.5 mm or any diameter described above, however, the window 2004 may have any suitable diameter corresponding to the percentages described above, for example the window may have a diameter of between about 50-200 microns, 75-150 microns, or about 100-125 microns. For example the diameter may be 90 microns, 130 microns, or 150 microns.

In certain embodiments, the ratio between the diameter of the active area of the imaging element/imaging fiber to the diameter of the window may be approximately at least: about 2×, about 3×, about 4×, about 5×, about 6×, about 8×, about 10×, or more than 10×. In certain embodiments where the window is non-circular, the ratio of the area of the window to the active area of the imaging element or imaging fiber may be at least about 5×, about 10×, about 15×, or about 20×.

Figure 13A:
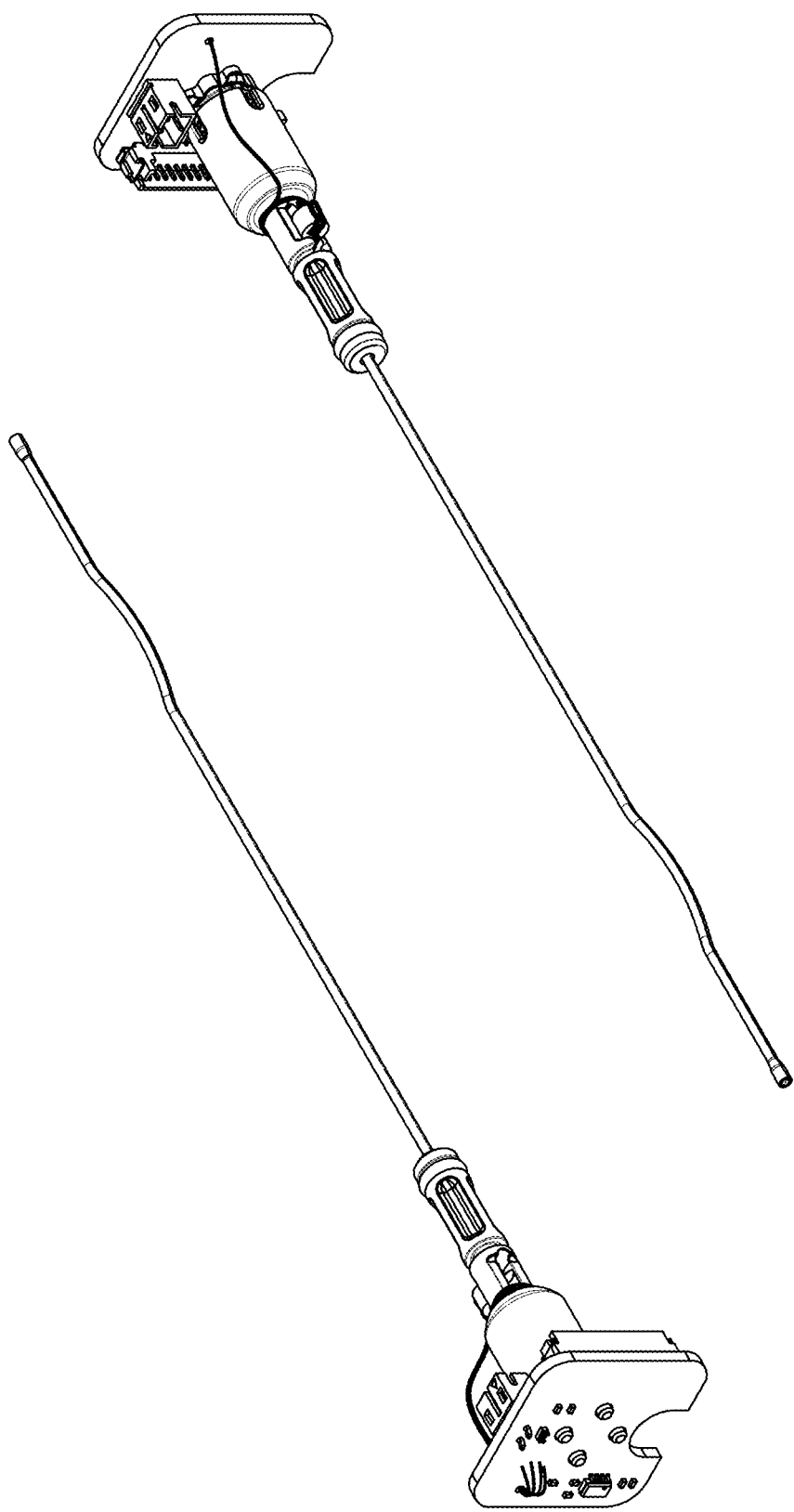
FIGS. 13A-C depict embodiments of a tissue visualization device comprising bent optical hypotubes.

FIG. 13A depicts an embodiment of an inner optical hypotube 3002, similar to the optical hypotubes depicted previously in FIGS. 3A-6C. Here, the optical hypotube is shown without the outer tubular body; however, in use the optical hypotube would be contained within an outer tubular body as shown in FIGS. 3A-6C. In embodiments, the optical hypotube may have a bend 3004, the bend biasing the distal end 3006 of the optical hypotube against the outer tubular body, when the optical hypotube is contained within an outer tubular body. In certain embodiments, the bend may be positioned about 50% down the length of the of the optical hypotube from the handpiece, about 60%, about 70%, about 80%, or about 90%. In certain embodiments the bend may be a gradual bend, wherein other embodiments the bend may be a sharp bend. In embodiments, there may be a single bend, two bends, three bends, four bends, five bends, or more than five bends. In certain embodiments, a bend may have a degree of bending of at least about: 1 degree, 5 degrees, 10 degrees, 15 degrees, 25 degrees, 35 degrees, 45 degrees, 50 degrees, 60 degrees, 75 degrees, or 90 degrees.

Figure 13B:
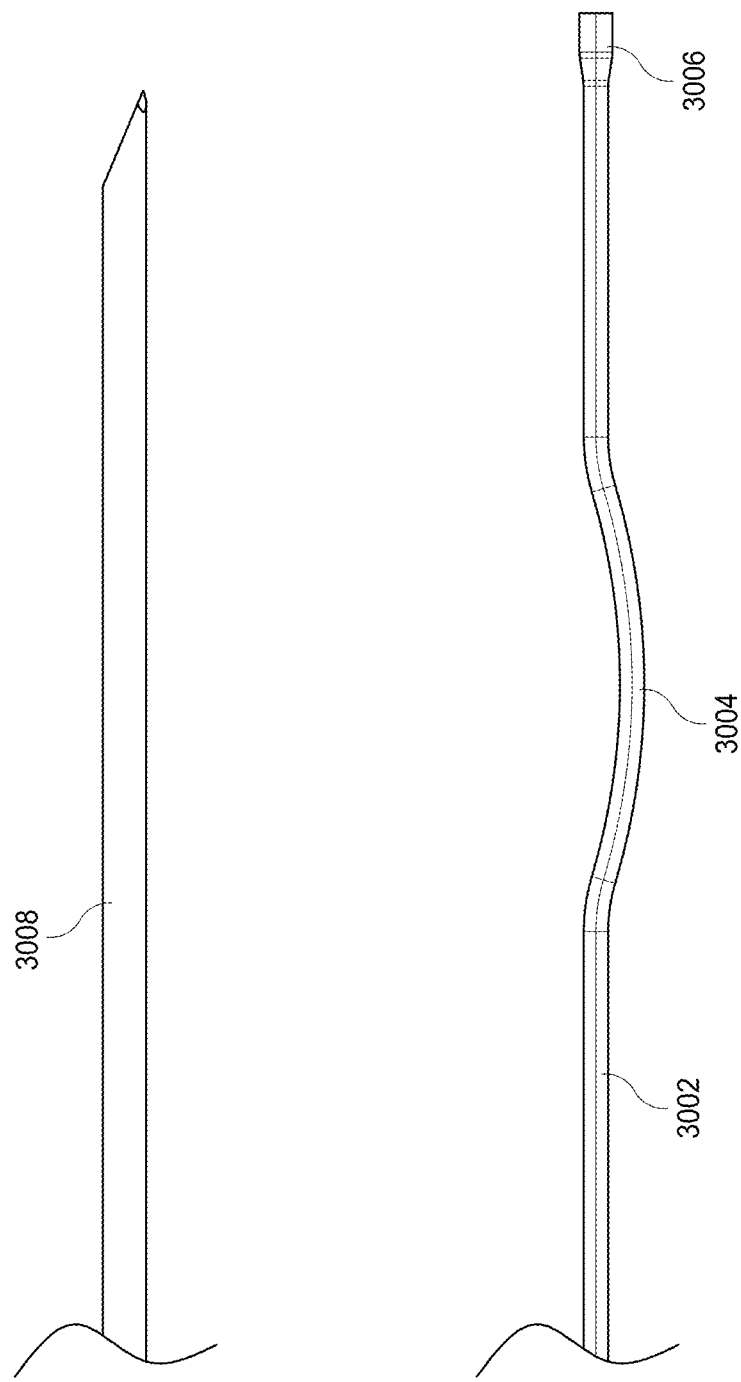
Figure 13C:
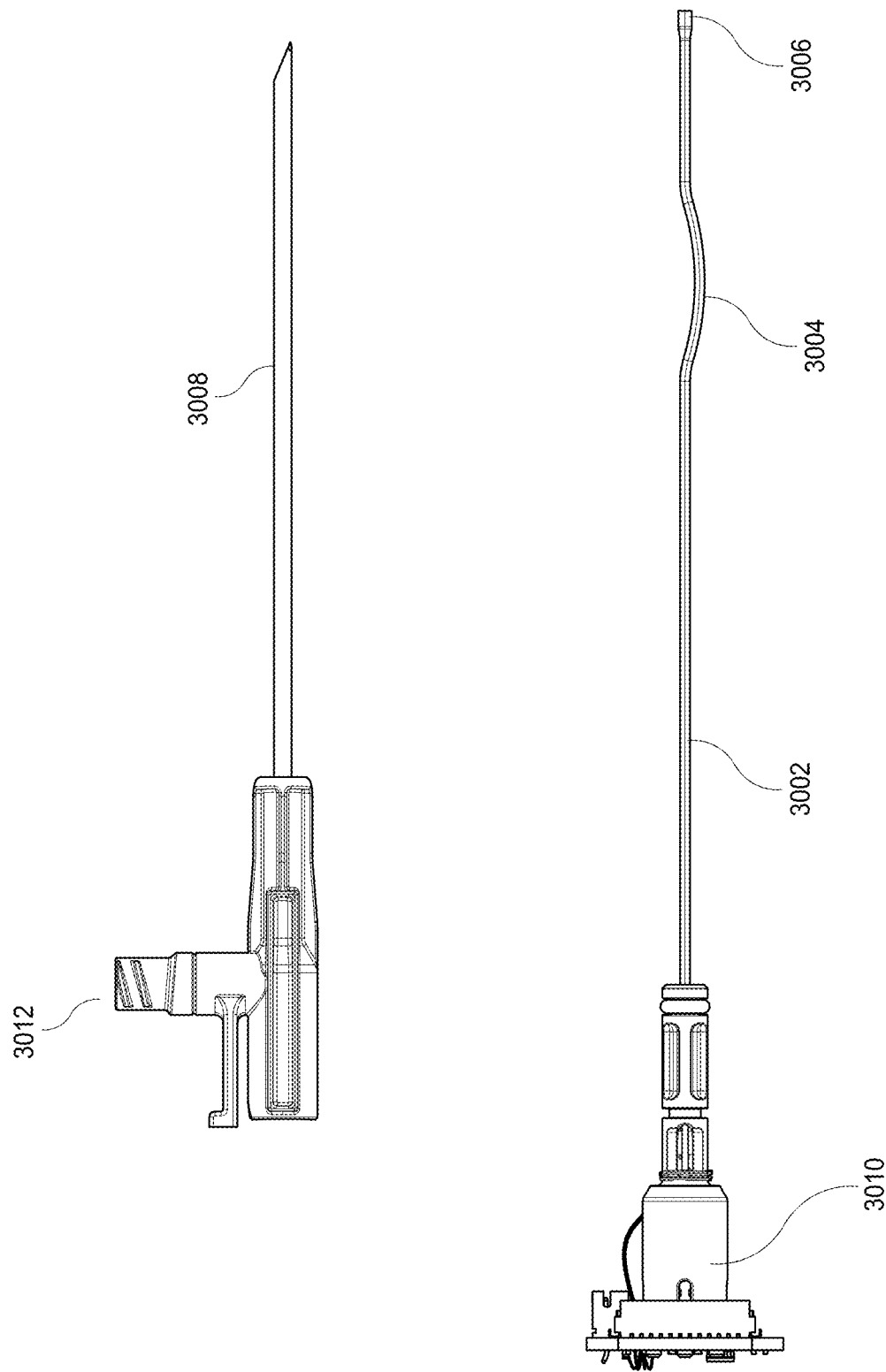

13B is a photograph of embodiments of the optical hypotube 3002 side by side with an embodiment of an outer tubular body 3006, similar to the outer tubular bodies depicted previously in FIGS. 3A-6C. Here, the bend 3004 is fairly gradual, biasing the tip 3006 against the sharpened distal end of the outer tubular body 3008. FIG. 13C further depicts embodiments of the optical hypotube 3002 and the outer tubular body 3008, however, here the needle hub assembly 3012 and the electro-optical assembly 3010, similar to the embodiments described above in relation to FIGS. 1-7.

Figure 14A:
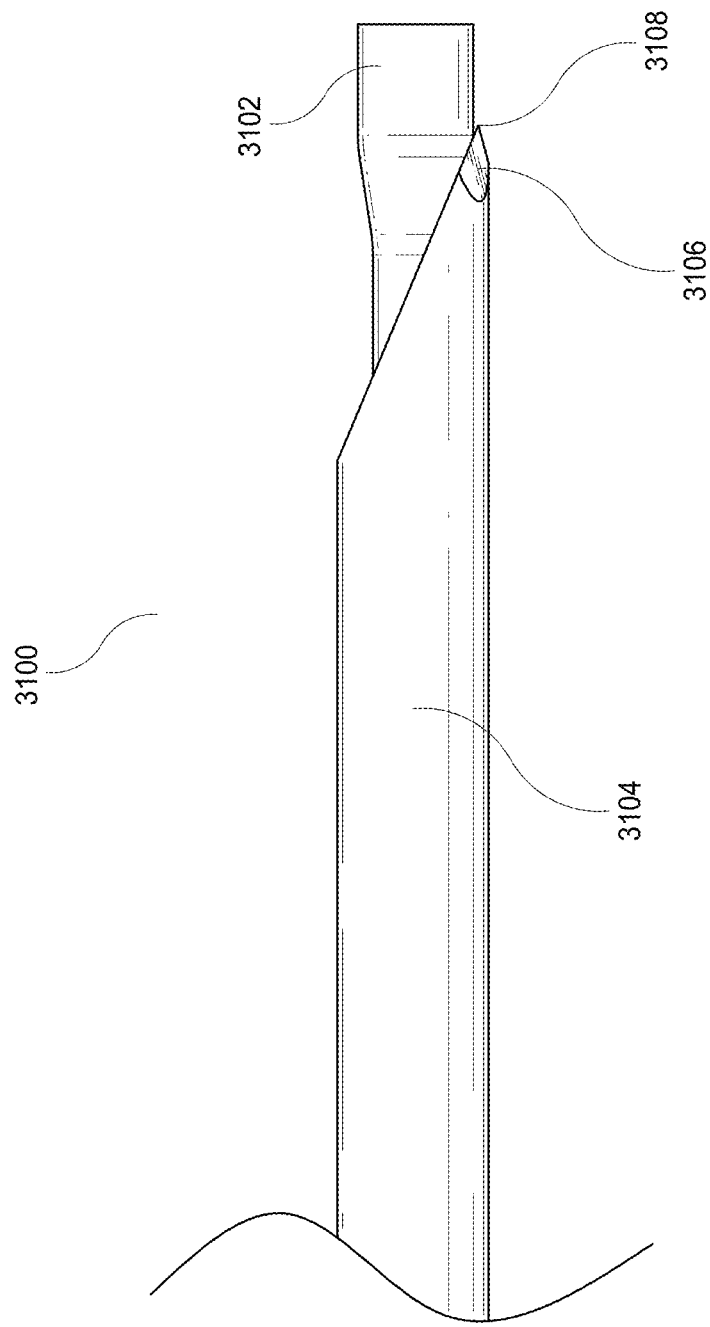
FIGS. 14A-B are a photograph and illustration of embodiments of the distal tip of a tissue visualization device.
Figure 14B:
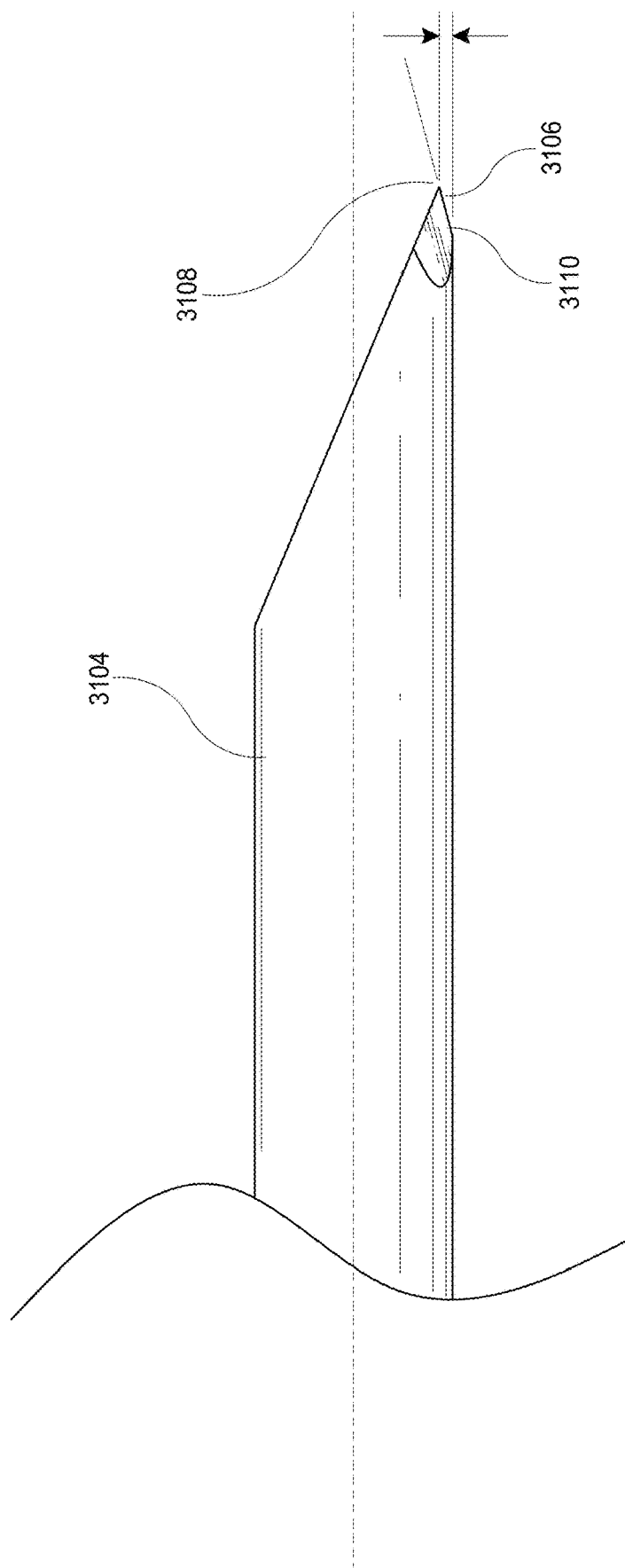

FIG. 14A is a close-up photograph of an embodiment of the distal end of the elongate body 3100, similar to those described previously, comprising outer tubular body 3104 and optical hypotube 3102. Here, the outer tubular body 3104 is retracted and blunted as will be described further below. As described previously, the elongate body has a reverse grind 3106 bringing the needle point 3108 closer to the optical hypotube. As shown in FIGS. 13A-C, the Optical Hypotube bending biases it against the inner diameter of the outer tubular body 3104, closest to the point of the sharpened tip 3108. As shown in previous embodiments, when the outer tubular body is retracted, it is blunted against the optical hypotube 3102. FIG. 14B depicts a close-up view of an embodiment of the distal end of the outer tubular body 3104, similar to the embodiments described previously. Here, the reverse grind on the outer tubular body, raises the sharpened tip upward, allowing the sharpened tip to be better blunted by the optical hypotube. In certain embodiments, the reverse grind may raise the sharpened tip upward by angle 3110. In certain embodiments, the angle may be about: 5 degrees, 10 degrees, 15 degrees, 25 degrees, 30 degrees, 45 degrees, 60 degrees, 75 degrees, 90 degrees, or more than 90 degrees.

In certain embodiments, the blunting contact between the optical hypotube 3102 and the outer tubular body 3104 may generate a tangential contact force. In some embodiments, a Huber type bend in the outer tubular body may result in tangential contact with the optical hypotube and deflect the hypotube to provide a contact force that provides blunting as the resistance to this force needs to be overcome before the optical hypotube no longer blunts the sharpened tip. In certain embodiments, the outer tubular body may comprise a long bend in needle to bias the optical hypotube towards the direction of bend of the outer tubular body for example, in certain embodiments, a bend may have a degree of bending of at least about: 1 degree, 5 degrees, 10 degrees, 15 degrees, 25 degrees, 35 degrees, 45 degrees, 50 degrees, 60 degrees, 75 degrees, or 90 degrees.

In certain embodiments, a thin-wall component may be attached to the optical hypotube to bias the optical hypotube in a certain direction and/or orientation. This component may have a larger diameter than the distal portion of the optical hypotube and could optionally be attached to the outer surface of the optical hypotube, for example at a point/line on the lower most portion of the outer diameter. This component may be in the form of a tube along the outside of the optical hypotube but in certain embodiments may have portions removed to minimize the impact to the lumen or fluid path. In certain embodiments, the thin wall component could be located at position proximal to the flare in the optical hypotube. Low profile "fingers" may be used to center the hypotube within the needle.

Figure 15:
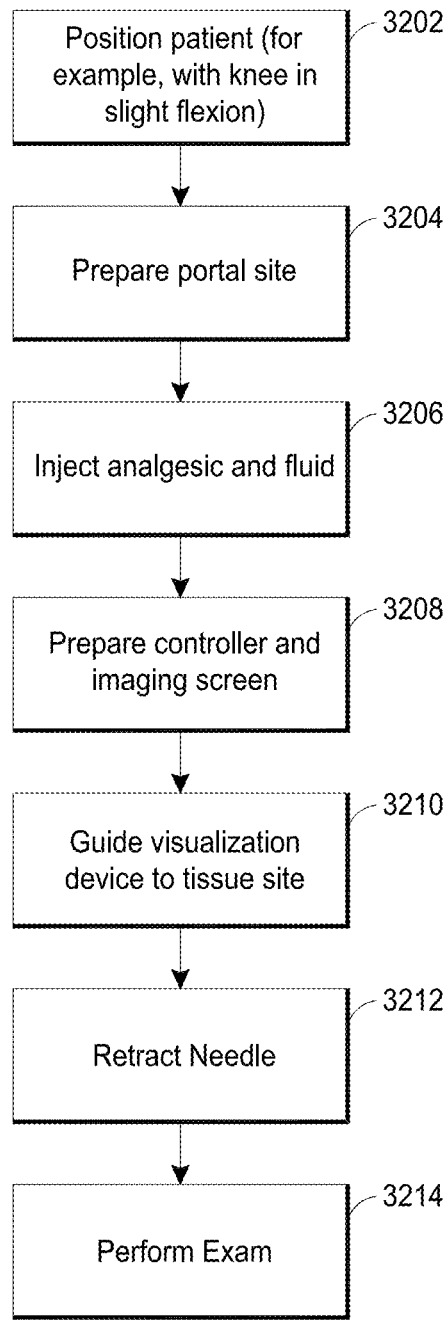
FIG. 15 depicts embodiments of a method for visualization an internal tissue site.

FIG. 15 is a flowchart showing an embodiment of a method for treating a tissue site in the knee using the apparatuses disclosed herein this section and throughout the specification. However, as will be understood by one of skill in the art, the method may be suitable for any type of joint and other tissue types. For example, the method may rely upon tissue visualization devices and systems such as shown in the previous figures, such as FIG. 1. In the first step, 3202, the patient may be positioned either supine or seated, with a joint in slight flexion. In the second step 3204, the portal site is prepared with a local aseptic solution. Next analgesic is delivered to the joint 3206 and the joint is filled with a minimum of 30cc of sterile fluid. In the fourth step 3208, the controller and viewing screen are turned on and the visualization device is connected to the controller and screen. Additionally, a stopcock and syringe may be attached to the visualization device. Next, the visualization device is inserted into the inferolateral or inferomedial portal, based on suspected pathology and guided to the tissue site 3210.

The visualization device may be inserted directly into the lateral or medial compartment, avoiding the "notch" and fat pad. Once inside the joint capsule, the sharpened tip of the outer tubular body or "needle" is retracted via the retraction button 3212. Lastly, a medical practitioner may perform an exam 3214 using the visualization device by applying varus and valgus tension on the tibia to allow for medial and lateral distention. Further, extending the knee allows for the posterior compartment to be more easily visualized. Additional sterile saline may be injected at any time as needed throughout the exam to clear the field of view.

In certain embodiments, while the visualization device is navigating toward the tissue site, the optical hypotube may remain retracted within the outer tubular body, allowing for a "tunnel" view of the tissue outside the outer tubular body. This approach advantageously reduces soft tissue interaction with the optical hypotube and provides an offset from the distal end, allowing for improved visualization in some cases. In certain embodiments, additional fluid may be added to the joint (such as a knee) to improve visualization by clearing debris and creating space for the optical components. Fluid may be added to the knee via a secondary needle to pre-condition the knee for visualization, prior to insertion of the visualization device. In some embodiments, fluid may be added to the knee through the visualization device while the outer tubular body is still in the forward position. Constant fluid may also be added via a syringe, such as by the physician or via an extension tube plus syringe depressed by an assistant. In some embodiments, short bursts of fluid (1-2 ml) may be applied to clear the area immediately in front of the visualization device.

Figure 16:
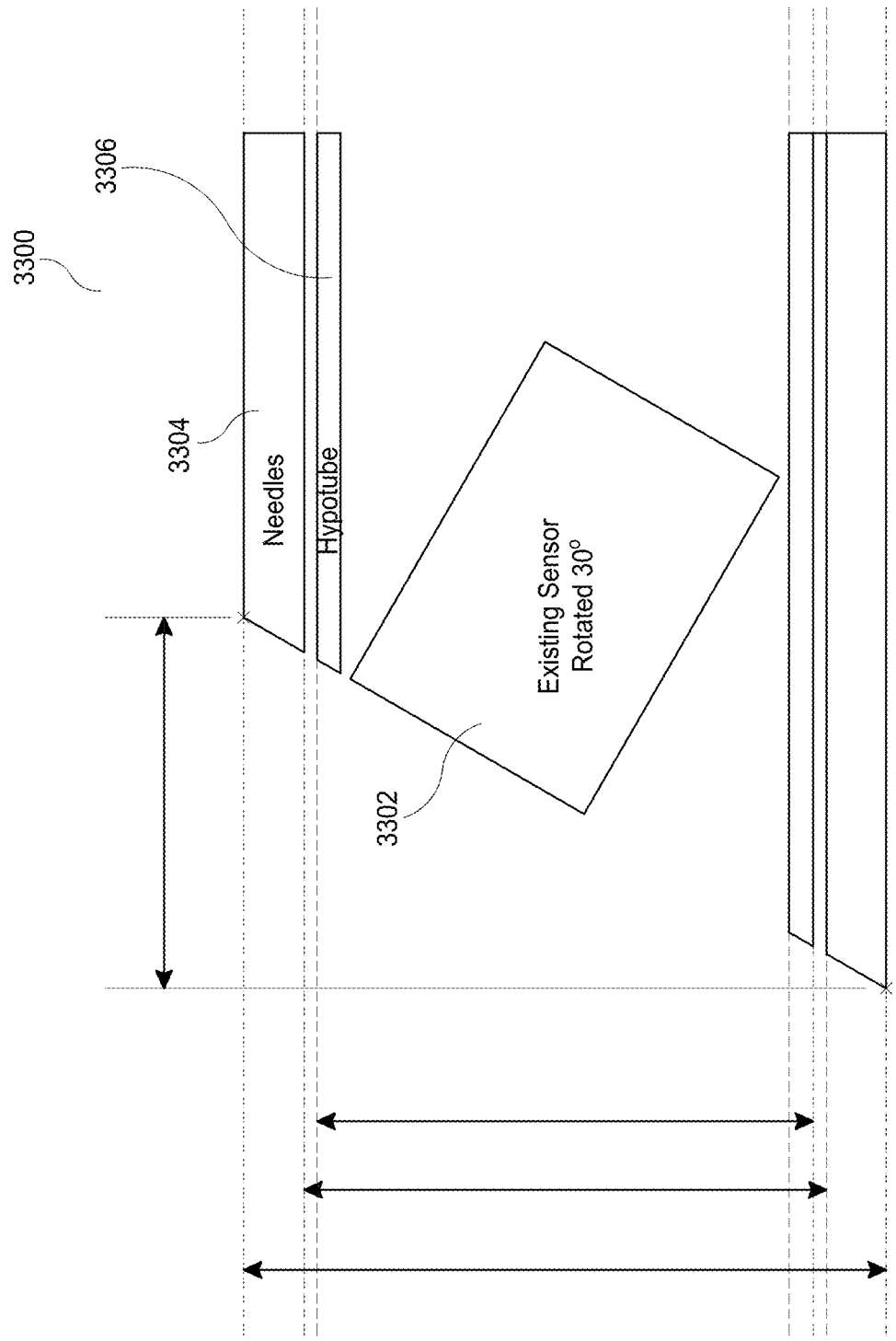
FIG. 16 depicts an embodiments of a visualization sensor at the distal end of a tissue visualization device.

FIG. 16 depicts an embodiment of a visualization sensor 3202 positioned at the distal end of an elongated body 3300 within the optical hypotube 3306 and outer tubular body or needle 3304, similar to the elongated bodies found in the visualization devices depicted in FIGS. 1-7. Here, the sensor 3302 is rotated approximately 30 degrees from the longitudinal axis of the elongated body. However, in some embodiments, the visualization sensor may be rotated at least about 5 degrees, 10 degree, 15 degree, 20 degrees, 30 degrees, 45 degrees, 60 degrees, 75 degrees, 90 degrees, or more than 90 degrees. In certain embodiments, such as described previously, the optical hypotube could also have a flared outer diameter at the distal tip, such as disclosed herein this section or elsewhere in the specification, but could also be straight as shown. As with the embodiments depicted previously in the specification in relation to the previous figures, illumination may be provided by various means such as via an optical fiber and/or discrete LEDs positioned at the distal end of the elongated body. The optical fiber and or LEDs may be oriented in the same axis as the visualization sensor, or in a different axis.

FIG. 17 depicts an embodiment of a visualization device, similar to the visualization devices of FIGS. 1-7. As described previous herein this specification, the image of tissue displayed on a screen, such as the screen 19 of FIG. 1, may be re-oriented to maintain the "up" position through communication with an orientation sensor. In certain embodiments, the screen may be re-oriented manually through the use of buttons. For example, on a square and/or circular screen, 4 buttons may be placed around the screen in at the top, bottom, left, and right. By pressing a button, the user may re-orient the screen to make the side of the screen where the button is pressed, now become the top of the screen or the "up" position. In this manner, a user may ensure that the screen is always facing in a desirable direction. In certain embodiments, as depicted in FIG. 17, such buttons 3402 may be positioned on the handpiece 3400 so that the user may press a button to rotate the image 45 degrees, 90 degrees, 135 degrees, 180 degrees, 225 degrees, 270 degrees, or 315 degrees to orient the screen in a desired position. Such buttons may be spaced 90 degrees apart and be located at the top, left, right and bottom of the handpiece as shown in the figure. An LED may be used to denote the active button and the current "up" position. In certain embodiments, there may be 1 button, 2 buttons, 3 buttons, 4 buttons, 6 buttons, 8 buttons or or more than 8 buttons to re-orient the screen. In certain embodiments, such as with a circular image, the screen may be configured to only rotate 45 degrees per button press.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. A visualization device, comprising:
   a handpiece;
   an outer tubular body having a proximal end affixed to the handpiece and a distal end;
   an elongate optical element extending through the outer tubular body and comprising an image sensor at the distal end, the elongate optical element comprising a first linear section extending from the handpiece, a bent section extending from the first linear section and a second linear section extending from the bent section, a distal end of the second linear section defining a distal end of the elongate optical element, the second linear section substantially parallel to the first linear section;
   wherein the bent section comprises a bend extending radially away from a longitudinal axis of the first linear section; and
   wherein when the outer tubular body is mounted to the handpiece, the bent section abuts against an inner surface of the outer tubular body to bias the distal end of the elongate optical element to an edge of the distal end of the outer tubular body.

2. The visualization device of claim 1, wherein the bent section is located at a position about 50-90% of the length of the elongate optical element from the handpiece.

3. The visualization device of claim 2, wherein the bent section is located at a position about 70% of the length of the elongate optical element from the handpiece.

4. The visualization device of claim 2, wherein the bent section is located at a position about 80% of the length of the elongate optical element from the handpiece.

5. The visualization device of claim 2, wherein the bent section is located at a position about 90% of the length of the elongate optical element from the handpiece.

6. The visualization device of claim 1, wherein the bent section comprises a degree of bending of about 35 degrees.

7. The visualization device of claim 1, wherein the bent section comprises a degree of bending of about 10 degrees.

8. The visualization device of claim 1, wherein the distal end of the elongate optical element is configured to provide illumination.

9. The visualization device of claim 1, wherein the first linear section comprises about 40% of the length of the elongate optical element.

* * * * *